US008114994B2

(12) United States Patent
Liotta et al.

(10) Patent No.: US 8,114,994 B2
(45) Date of Patent: Feb. 14, 2012

(54) 2' AND 3'-SUBSTITUTED CYCLOBUTYL NUCLEOSIDE ANALOGS FOR THE TREATMENT VIRAL INFECTIONS AND ABNORMAL CELLULAR PROLIFERATION

(75) Inventors: Dennis C. Liotta, Atlanta, GA (US); Shuli Mao, Atlanta, GA (US); Michael Hager, Kennesaw, GA (US); Raymond F Schinazi, Atlanta, GA (US)

(73) Assignee: Emory University, Atlanta, GA (US)

( * ) Notice: Subject to any disclaimer, the term of this patent is extended or adjusted under 35 U.S.C. 154(b) by 221 days.

(21) Appl. No.: 12/368,876

(22) Filed: Feb. 10, 2009

(65) Prior Publication Data
US 2009/0149416 A1    Jun. 11, 2009

Related U.S. Application Data

(63) Continuation of application No. 11/301,326, filed on Dec. 8, 2005, now Pat. No. 7,495,006.

(60) Provisional application No. 60/634,875, filed on Dec. 10, 2004.

(51) Int. Cl.
*A61K 31/505* (2006.01)
*A61K 31/513* (2006.01)
*A61K 31/52* (2006.01)
*C07D 473/18* (2006.01)
*C07D 473/34* (2006.01)
*C07D 239/47* (2006.01)
*C07D 239/54* (2006.01)

(52) U.S. Cl. ........ 544/265; 544/277; 544/317; 544/318; 514/81; 514/86; 514/263.37; 514/274

(58) Field of Classification Search .................. None
See application file for complete search history.

(56) References Cited

U.S. PATENT DOCUMENTS

| 4,855,466 | A | 8/1989 | Zahler et al. |
| 4,918,075 | A | 4/1990 | Zahler et al. |
| 5,126,345 | A | 6/1992 | Slusarchyk et al. |
| 5,130,462 | A | 7/1992 | Slusarchyk et al. |
| 5,166,397 | A | 11/1992 | Narita et al. |
| 5,185,459 | A | 2/1993 | Slusarchyk et al. |
| 5,324,730 | A | 6/1994 | Ichikawa et al. |
| 7,495,006 | B2 * | 2/2009 | Liotta et al. .............. 514/263.23 |
| 2004/0229839 | A1 | 11/2004 | Babu et al. |
| 2006/0223835 | A1 | 10/2006 | Liotta et al. |

FOREIGN PATENT DOCUMENTS

| EP | 0322854 | 7/1989 |
| EP | 0330992 A2 | 9/1989 |
| EP | 0366059 | 5/1990 |
| EP | 0458363 | 11/1991 |
| WO | WO 2006/063281 A2 | 6/2006 |
| WO | WO 2006/063281 A3 | 12/2006 |

OTHER PUBLICATIONS

Silverman, Richard B., "The Organic Chemistry of Drug Design and Drug Action" chapter 8, "Prodrugs and Drug Delivery Systems" Published 1992 by Academic Press, pp. 352-397.*
Takahashi et al., "Inhibition of vertebrate telomerases by the triphosphate derivatives of carbocyclic oxetanocin analogs" Nucleic Acids Research Supplement (2003) No. 3 pp. 285-286.*
Maruyama et al., "Synthesis and Antiviral Activity of Carbocyclic Oxetanocin Analogues (C-OXT-A, C-OXT-G) and Related Compounds. II" (1993) vol .41 No. 3 pp. 516-521.*
Anonymous, "Lubocavir" in *AIDSMAP Treatment and Care*, (Epublication Jan. 8, 2003) at http://www.aidsmap.com/en/docs/FE221C85-DB10-4E87-804B-BEE0480A0BC8.asp.
Bisacchi, G.S., et al., "Synthesis and antiviral activity of enantiomeric forms of cyclobutyl nucleoside ana-logues," *J. Med. Chem.*, 34(4):1415-1421 (Apr. 1991).
Dunkle, L.M., et al., "Lobucavir: a promising broad-spectrum antiviral agent," *11th Int. Conf. AIDS* (Van-couver, Canada, Jul. 7-12, 1996) program supplement, p. 20, Abstract No. Th.B.943; provided as Natl. Libr. Med. Gateway abstract, NLM Unique ID No. 9870004.
Hayashi, S., et al., "Cyclobut-A and cyclobut-G, carbocyclic oxetanocin analogs that inhibit the replication of human immunodeficiency virus in T cells and monocytes and macrophages in vitro," (1990) *Antimicrob. Agents Chemother.*, 34(2):287-294 (Feb. 1990).
Kamiya, N., "The mechanisms of action of antivirals against hepatitis B virus infection," *J. Antimicrob. Chemother.*, 51(5):1085-1089 (May 2003) (published electronically Apr. 14, 2003).
Lalezari, J., et al., "In vivo anti-CMV activity and safety of oral lobucavir in HIV-infected patients," *4th Conf. Retrovir. Oppor. Infect.* (Washington, D.C., Jan. 22-26, 1997), Session 31, p. 120, Abstract No. 301; also provided in more legible form as Natl. Libr. Med. Gateway abstract, NLM Unique ID No. 100928314.
Maruyama, T., et al., "Synthesis and antiviral activities of carbocyclic oxetanocin analogues," *Chem. Pharm. Bull.* (Tokyo), 38(10):2719-2725 (Oct. 1990).
The Merck Manual of Diagnosis and Therapy, 17th Edition; published 1999 by Merck Research Laboratories. Ed. By Beers and Berkow, pp. 1132-1135.
Nishizono, et al., "Nucleosides and Nucleotides; 159. Synthesis of Thietane Nucleosides Via the Pum-merer Reaction as a Key Step." *Tetrahedron Letters* (1996) vol. 37, No. 42, pp. 7569-7572.
Poizot-Martin et al., "Efficacy and Tolerance of HCV Treatment in HIV_HCV Coinfected Patients: The Potential Interaction of PI Treatment." HIV Clinical Trials (2003) vol. 4, No. 4, pp. 262-268.

* cited by examiner

*Primary Examiner* — Eric S Olson
(74) *Attorney, Agent, or Firm* — Emory Patent Group; James C. Mason; Susanne Hollinger

(57) ABSTRACT

Provided are cyclobutyl nucleosides and methods for their use in treatment of infections including Retroviridae (including HIV), Hepadnaviridae (including HBV), or Flaviviridae (including BVDV and HCV) infection, or conditions related to abnormal cellular proliferation, in a host, including animals, and especially humans.

35 Claims, 2 Drawing Sheets

2' AND 3'-SUBSTITUTED CYCLOBUTYL NUCLEOSIDE ANALOGS FOR THE TREATMENT VIRAL INFECTIONS AND ABNORMAL CELLULAR PROLIFERATION

CROSS REFERENCE TO RELATED APPLICATION

This application is a continuation of U.S. patent application Ser. No. 11/301,326, filed Dec. 8, 2005, now U.S. Pat. No. 7,495,006, which claims priority to U. S. Provisional Application No. 60/634,875, filed Dec. 10, 2004.

FIELD OF THE INVENTION

The present invention includes compounds and methods for the treatment of Retroviridae (including HIV), Hepadnaviridae (including HBV), or Flaviviridae (including BVDV and HCV) infections, and abnormal cellular proliferation. This invention is in the field of HIV, HBV, HCV infection and cancer treatment. The invention also provides novel nucleoside analogs with therapeutic properties.

DESCRIPTION OF RELATED ART

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). In 1985, it was reported that the synthetic nucleoside 3'-azido-3'-deoxythymidine (AZT) inhibits the replication of human immunodeficiency virus. Since then, a number of other synthetic nucleosides, have been discovered and developed for the treatment of HIV. After cellular phosphorylation to the 5'-triphosphate by cellular kinases, synthetic nucleosides are typically incorporated into a growing strand of viral DNA, causing chain termination due to the absence of the 3'-hydroxyl group. They can also inhibit the viral enzyme reverse transcriptase.

Although considerable progress has been made in the treatment of AIDS, the emergence of mutated variants of human immunodeficiency virus type 1 (HIV-1) resistant to antiviral drugs is a major problem. Drug resistance most typically occurs by mutation of a gene that encodes for an enzyme used in viral replication, and most typically in the case of HIV, reverse transcriptase, protease, or DNA polymerase. It has been demonstrated that the efficacy of a drug against HIV infection can be prolonged, augmented, or restored by administering the compound in combination or alternation with a second, and perhaps third, antiviral compound that induces a different mutation from that caused by the principle drug.

Hepatitis B Virus

Another virus that causes a serious human health problem is the hepatitis B virus (referred to below as "HBV"). HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is very similar to that of acquired immune deficiency syndrome, which accounts for why HBV infection is common among patients infected with HIV or AIDS. However, HBV is more contagious than HIV.

Bisacchi, et al. ((1991) J. Med. Chem. 34:1415-1421) describes the synthesis of enantiomers of several cyclobutyl nucleosides, however these compounds were only described as active against herpes virus (see also Maruyama, et al. (1990) Chem Pharm Bull (Tokyo) 38(10):2719-25). Also see discussion in Kamiya, N. (2003) J Antimicr. Chemo. 51:1085-1089.

Several cyclobutyl nucleoside analogs have been tested for HBV activity. Bristol-Myers Squibb has various patents (see for example, U.S. Pat. Nos. 5,324,730; 5,185,459; 5,166,397; 5,130,462; and 5,126,345) directed to cyclobutyl nucleosides of the formula:

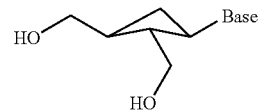

In particular, lobucavir, ((R)-9-[2,3-Bis(hydroxymethyl) cyclobutyl]guanine), also known as cygalovir or by the codename BMS 180194, is an oral anti-viral drug that was under development by Bristol-Myers Squibb in the mid-1990's; however development was discontinued based on its toxicity profile. Lobucavir is a cyclobutyl analog of guanine with broad spectrum antiviral activity against most herpes viruses and Hepatitis B. In the test-tube it was also found to be active against a broad range of viruses including HIV, CMV, herpes simplex, varicella zoster virus and Epstein-Barr virus. Preliminary human data show a dose-related anti-CMV effect, and good anti-HIV activity, with as much as 1.5 log reductions in HIV viral load after 28 days treatment. however, an international Phase III study of lobucavir as therapy for hepatitis B was suspended in February 1999 owing to concerns about the safety of the drug (Hayashi, et al. (1990) Antimicrob Agents Chemother. 34(2):287-94; Dunkle L M et al. Eleventh International Conference on AIDS, Vancouver, abstract Th. B. 943, 1996; Lalezari J et al. Fourth Conference on Retroviruses and Opportunistic Infections, Washington, abstract 301, 1997).

Flaviridiae

The Flaviviridae is a group of positive single-stranded RNA viruses with a genome size from 9-15 kb. They are enveloped viruses of approximately 40-50 nm. An overview of the Flaviviridae taxonomy is available from the International Committee for Taxonomy of Viruses. The Flaviviridae consists of three genera.

1. Flaviviruses. This genus includes the Dengue virus group (Dengue virus, Dengue virus type 1, Dengue virus type 2, Dengue virus type 3, Dengue virus type 4), the Japanese encephalitis virus group (Alfuy Virus, Japanese encephalitis virus, Kookaburra virus, Koutango virus, Kunjin virus, Murray Valley encephalitis virus, St. Louis encephalitis virus, Stratford virus, Usutu virus, West Nile Virus), the Modoc virus group, the Rio Bravo virus group (Apoi virus, Rio Brovo virus, Saboya virus), the Ntaya virus group, the Tick-Borne encephalitis group (tick born encephalitis virus), the Tyuleniy virus group, Uganda S virus group and the Yellow Fever virus group. Apart from these major groups, there are some additional Flaviviruses that are unclassified.

2. Hepaciviruses. This genus contains only one species, the Hepatitis C virus (HCV), which is composed of many clades, types and subtypes.

3. Pestiviruses. This genus includes Bovine Viral Diarrhea Virus-2 (BVDV-2), Pestivirus type 1 (including BVDV), Pestivirus type 2 (including Hog Cholera Virus) and Pestivirus type 3 (including Border Disease Virus). One of the most important Flaviviridae infections in humans is caused by the hepatitis C virus (HCV). This is the second major cause of viral hepatitis, with an estimated 170 million carriers worldwide (World Health Organization; Hepatitis C: global prevalence, Weekly Epidemiological Record, 1997, 72, 341), 3.9 million of whom reside in the United States (Centers for Disease Control; unpublished data, http://www.cdc.gov/ncidod/diseases/hepatitis/heptab3.htm).

Abnormal Cellular Proliferation

Cellular differentiation, growth, function and death are regulated by a complex network of mechanisms at the molecular level in a multicellular organism. In the healthy animal or human, these mechanisms allow the cell to carry out its designed function and then die at a programmed rate.

Abnormal cellular proliferation, notably hyperproliferation, can occur as a result of a wide variety of factors, including genetic mutation, infection, exposure to toxins, autoimmune disorders, and benign or malignant tumor induction. There are a number of skin disorders associated with cellular hyperproliferation. Psoriasis, for example, is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, Int. J. Dermatol. 18:111, 1979). Approximately 2% of the population in the United States have psoriasis, occurring in about 3% of Caucasian Americans, in about 1% of African Americans, and rarely in native Americans. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross, R. Nature, 1993, 362:801-809). Both cell migration and cell proliferation play a role in the formation of atherosclerotic lesions. Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, E. D., Jr., The New England Journal of Medicine, 1990, 322: 1277-1289), and to be caused by autoantibodies produced against collagen and IgE.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

A tumor, also called a neoplasm, is a new growth of tissue in which the multiplication of cells is uncontrolled and progressive. A benign tumor is one that lacks the properties of invasion and metastasis and is usually surrounded by a fibrous capsule. A malignant tumor (i.e., cancer) is one that is capable of both invasion and metastasis. Malignant tumors also show a greater degree of anaplasia (i.e., loss of differentiation of cells and of their orientation to one another and to their axial framework) than benign tumors.

A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

All of the various cell types of the body can be transformed into benign or malignant tumor cells. The most frequent tumor site is lung, followed by colorectal, breast, prostate, bladder, pancreas, and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three types of therapies: surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia.

Chemotherapy involves the disruption of cell replication or cell metabolism. It is used most often in the treatment of leukemia, as well as breast, lung, and testicular cancer.

In light of the fact that HIV, acquired immune deficiency syndrome (AIDS), AIDS-related complex, and hepatitis B and C viruses have reached epidemic levels worldwide, and have tragic effects on the infected patient, there remains a strong need to provide new effective pharmaceutical agents to treat these diseases that have low toxicity to the host. Further, there is a need to provide new antiproliferative agents.

Therefore, it is an object of the present invention to provide a compound, method and composition for the treatment of a host infected with a virus belonging to the Retroviridae (including HIV), Hepadnaviridae (including HBV), and/or Flaviviridae (including BVDV and HCV) family.

It is an object of the present invention to provide a compound, method and composition for the treatment of human patients infected with HIV.

It is an object of the present invention to provide a compound, method and composition for the treatment of human patients infected with hepatitis B or C.

It is a further object of the present invention to provide new antiproliferative agents.

It is another object of the present invention to provide a compound, method and composition for the treatment of a host, including animals and especially humans, with abnormal cellular proliferation.

It is a further object to provide a compound, method and composition for the treatment of a host, including animals and especially humans, with a tumor, including non-malignant and malignant tumors.

It is another object of the present invention to provide new drugs for the treatment of HIV that is resistant to other antiviral compounds.

It is an object of the present invention to provide a compound, method and composition for the treatment of human patients infected with a mutant strain of HIV.

It is an object of the present invention to provide a compound, method and composition for the treatment of human patients infected with a multiple drug resistant strain of HIV.

It is yet another object of the invention to provide new compounds, methods and compositions for treatment of patients infected with HIV with another antiviral compound while advantageously combating drug resistance.

SUMMARY OF THE INVENTION

The present invention provides cyclobutyl nucleosides of formula (I)-(IV) or their pharmaceutically acceptable salts, esters, salts of esters, prodrugs, or salts of prodrugs, for the treatment of a host infected with a virus belonging to the Retroviridae (including HIV), Hepadnaviridae (including HBV), and/or Flaviviridae (including BVDV and HCV) family. Alternatively, the cyclobutyl nucleosides of formula (I)-(IV) or its pharmaceutically acceptable salt, ester, salt of ester, prodrug, or salt of prodrug, can be used for the treatment of abnormal cellular proliferation. Specifically, the invention also includes compounds, compositions, and methods for treating or preventing the following:

(a) an Retroviridae infection, including an HIV infection;
(b) a Hepadnaviridae infection including hepatitis B virus (HBV) infection;
(c) a Flaviviridae infection, including all members of the Hepacivirus genus (HCV), Pestivirus genus (BVDV, CSFV, BDV), or Flavivirus genus (Dengue virus, Japanese encephalitis virus group (including West Nile Virus), and Yellow Fever virus); and/or (d) abnormal cellular proliferation, including psoriasis, eczema, atherosclerosis, asthma, arthritis, osteoprorosis, leukemia, and malignant tumors.

In one embodiment, the anti-virally or anti-proliferative effective nucleoside is a cyclobutyl nucleoside of the general formula (I)-(IV):

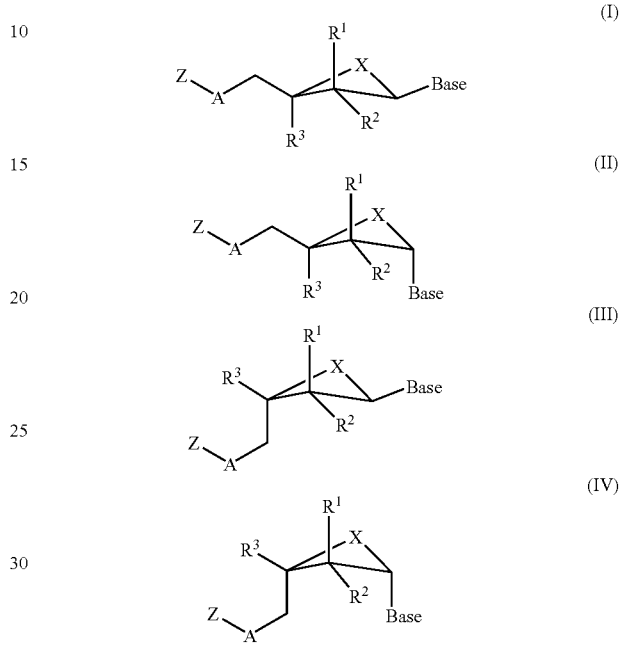

or its pharmaceutically acceptable salt, ester, salt of an ester, prodrug, salt of a prodrug, enantiomer, diastereomer, or tautomer thereof, wherein;

Base is a purine or pyrimidine base;

Z is independently H; phosphate (including monophosphate, diphosphate, triphosphate, or a stabilized phosphate prodrug); P(O)Z'Z'', CH$_2$P(O)Z'Z'', acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein Z is independently H or phosphate; Z' and Z'' each independently is OH, OAlkyl, OAryl, alkyl, aryl, SH, SAlkyl, SAryl, NH$_2$, mono or di-alkylamino, mono- or di-arylamino, or a residue of an amino acid;

A is O, S, or CH$_2$; or alternatively

A can be a covalent bond when Z is P(O)Z'Z'' or CH$_2$P(O)Z'Z'';

$R_1$, $R_2$, and $R_3$ are independently hydrogen, lower alkyl ($C_1$, $C_2$, $C_3$, $C_4$, $C_5$, and $C_6$ alkyl), halogenated lower alkyl, CF$_3$, 2-Br-ethyl, lower alkenyl ($C_2$, $C_3$, $C_4$, $C_5$, and $C_6$ alkenyl), halogenated lower alkenyl, Br-vinyl, lower alkynyl ($C_2$, $C_3$, $C_4$, $C_5$, and $C_6$ alkenyl), halogenated lower alkynyl, halo (fluoro, chloro, bromo, iodo), cyano, azido, NO$_2$, NH$_2$, —NH(lower alkyl), NH(acyl), N(lower alkyl)$_2$, —N(acyl)$_2$, hydroxy, OZ, O(lower acyl), O(lower alkyl), O(alkenyl), C(O)O(alkyl), C(O)O(lower alkyl); or alternatively, $R_1$ and $R_2$ together are $=CH_2$ or $=CHY$; or alternatively $R_1$ and $R_2$ can come together to form a three-membered carbocyclic or heterocyclic ring, such as an epoxide ring; such that if $R_1$ is H, then $R_2$ is not $CH_2OH$, and if $R_2$ is H, then $R_1$ is not $CH_2OH$;

X is $CH_2$, CHY, or S; and

Y is H, methyl, halogenated methyl, $CF_3$, halogen (F, Cl, Br, or I), $N_3$, cyano, or $NO_2$.

In one embodiment of the invention, Z is not H. In another embodiment of the invention, $R_1$ and $R_2$ are not both H.

In one particular embodiment, the base is a pyrimidine. In a particular sub-embodiment, the pyrimidine is a 5-fluorocytidine.

In one particular embodiment, the base is a purine. In a particular sub-embodiment, the purine is guanine or adenine.

In another particular embodiment of the invention, the anti-virally or anti-proliferative effective nucleoside is:

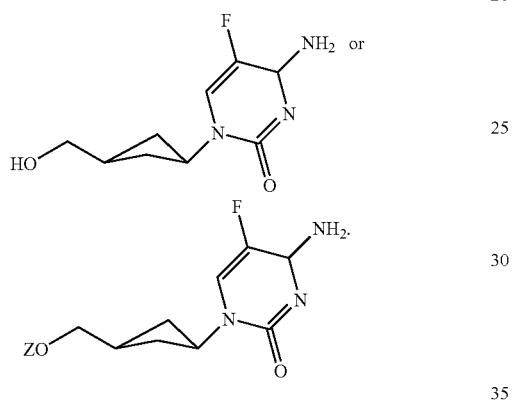

In one particular embodiment, the anti-virally or anti-proliferative effective nucleoside is selected from the group consisting of:

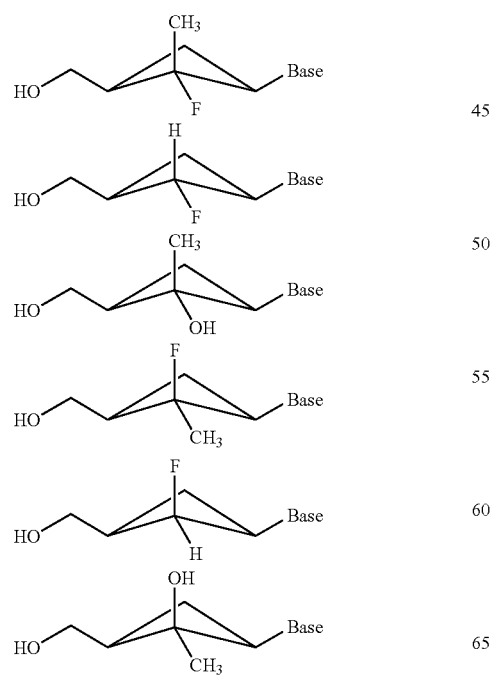

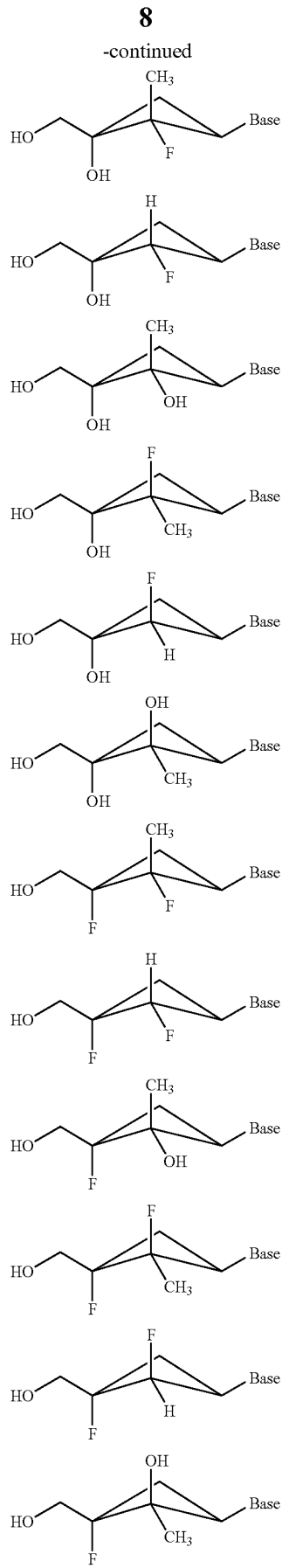

-continued

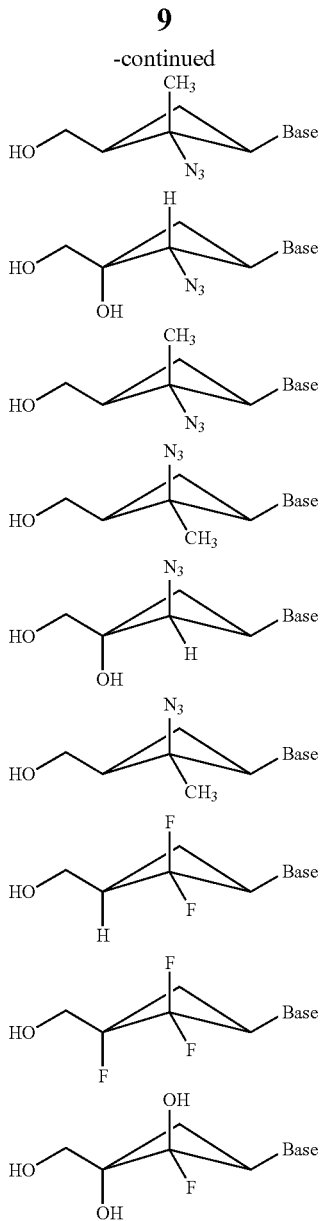

or its pharmaceutically acceptable salt, ester, salt of an ester, prodrug, salt of a prodrug, enantiomer, diastereomer, or tautomer thereof, wherein each OH can be substituted with OZ, wherein Z is as defined above.

In one particular embodiment, the base is a pyrimidine. In a particular sub-embodiment, the pyrimidine is a 5-fluorocytidine.

In one particular embodiment, the base is a purine. In a particular sub-embodiment, the purine is guanine or adenine.

In another embodiment, the anti-virally or anti-proliferative effective nucleoside is selected from the group consisting of:

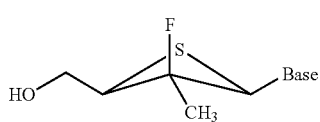

-continued

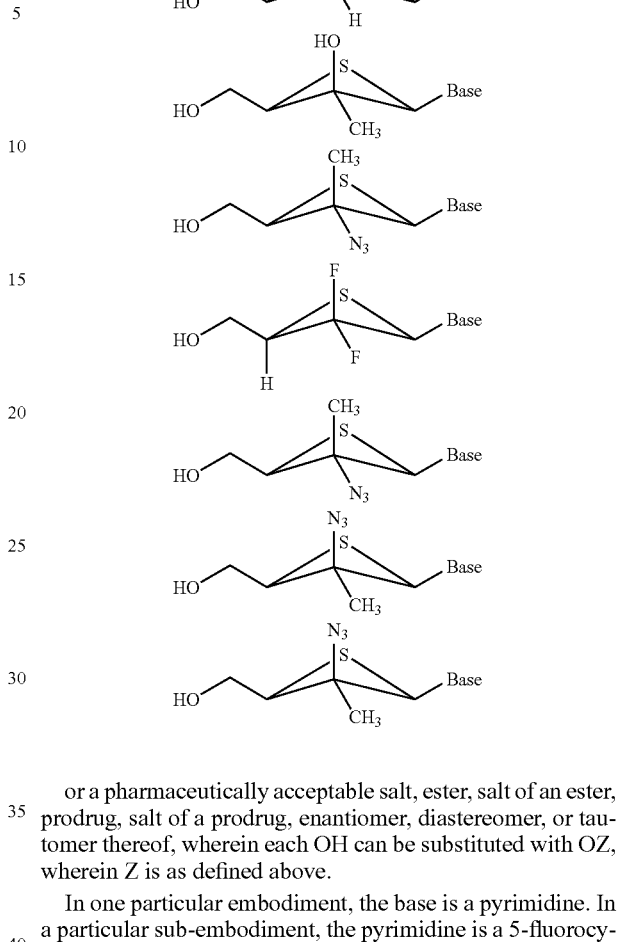

or a pharmaceutically acceptable salt, ester, salt of an ester, prodrug, salt of a prodrug, enantiomer, diastereomer, or tautomer thereof, wherein each OH can be substituted with OZ, wherein Z is as defined above.

In one particular embodiment, the base is a pyrimidine. In a particular sub-embodiment, the pyrimidine is a 5-fluorocytidine.

In one particular embodiment, the base is a purine. In a particular sub-embodiment, the purine is guanine or adenine.

In another embodiment, the anti-virally or anti-proliferative effective nucleoside is selected from the group consisting of:

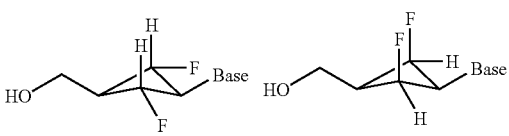

or a pharmaceutically acceptable salt, ester, salt of an ester, prodrug, salt of a prodrug, enantiomer, diastereomer, or tautomer thereof, wherein each OH can be substituted with OZ, wherein Z is as defined above.

In one particular embodiment, the base is a pyrimidine. In a particular sub-embodiment, the pyrimidine is a 5-fluorocytidine.

In one particular embodiment, the base is a purine. In a particular sub-embodiment, the purine is guanine or adenine.

In another embodiment, the anti-virally or anti-proliferative effective nucleoside is selected from the group consisting of:

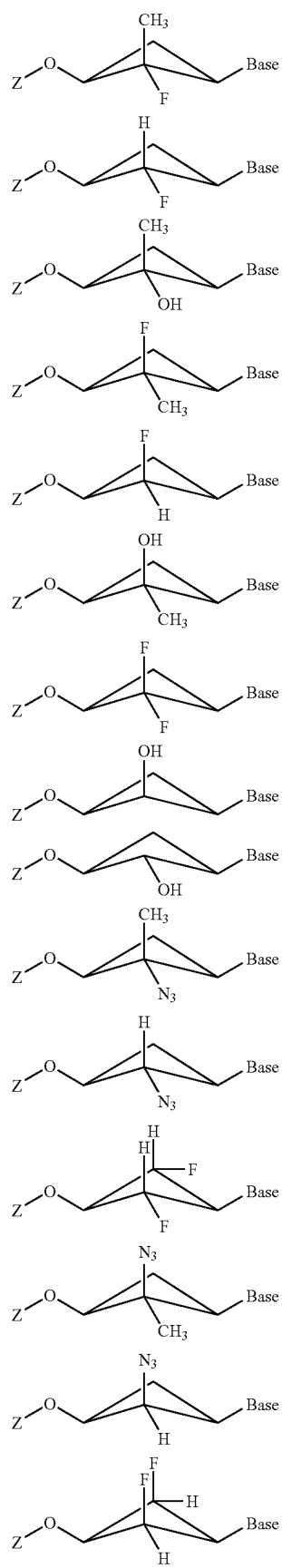

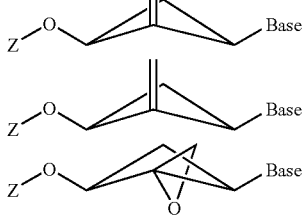

or a pharmaceutically acceptable salt, ester, salt of an ester, prodrug, salt of a prodrug, enantiomer, diastereomer, or tautomer thereof, wherein Z is as defined above.

In one particular embodiment, the base is a pyrimidine. In a particular sub-embodiment, the pyrimidine is a 5-fluorocytidine.

In one particular embodiment, the base is a purine. In a particular sub-embodiment, the purine is guanine or adenine.

In one embodiment, the nucleoside has an EC50 (effective concentration to achieve 50% viral inhibition) when tested in an appropriate cell-based assay, of less than 15 micromolar, and more particularly, less than 10 or 5 micromolar. In a preferred embodiment, the nucleoside is enantiomerically enriched.

The present invention also includes at least the following features:

(a) use of a cyclobutyl nucleoside of formula (I)-(IV), as described herein, or its pharmaceutically acceptable salt or prodrug thereof in a medical therapy, i.e. as an antiviral or antitumor/anticancer agent, for example for the treatment or prophylaxis of a Retroviridae (including HIV), Hepadnaviridae (including HBV), and/or Flaviviridae (including BVDV and HCV) infections, or of a disease characterized by abnormal cellular proliferation, such as cancer, leukemia or tumor;

(b) use of a cyclobutyl nucleoside of formula (I)-(IV), as described herein, or its pharmaceutically acceptable salt or prodrug thereof in the manufacture of a medicament for treatment of a Retroviridae (including HIV), Hepadnaviridae (including HBV), and/or Flaviviridae (including BVDV and HCV) infection, or of a disease characterized by abnormal cellular proliferation, such as cancer, leukemia or tumor;

(c) a pharmaceutical composition that include an antivirally effective amount of a cyclobutyl nucleoside of formula (I)-(IV), as described herein, or its pharmaceutically acceptable salt or prodrug thereof together with a pharmaceutically acceptable carrier or diluent according to the present invention;

(d) a pharmaceutical composition with a cyclobutyl nucleoside of formula (I)-(IV), as described herein, or its pharmaceutically acceptable salt or prodrug thereof in combination with one or more other antivirally effective agents; and (e) process for the preparation of a cyclobutyl nucleoside of formula (I)-(IV), as described herein, and their pharmaceutically acceptable salts and prodrugs thereof.

The cyclobutyl nucleoside of formula (I)-(IV) are biologically active molecules which are useful in the treatment of hepatitis B, hepatitis C or HIV. The compounds are also useful for the treatment of abnormal cellular proliferation, including tumors and cancer. One can easily determine the spectrum of activity by evaluating the compound in the assays described herein or with another confirmatory assay.

In another embodiment, for the treatment of hepatitis, hepatitis B or C, or HIV, the active compound or its derivative or salt can be administered in combination or alternation with another antiviral agent, such as an anti-HIV agent or anti-hepatitis agent, including those of the formula above. In general, in combination therapy, an effective dosage of two or more agents are administered together, whereas during alternation therapy, an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include Emtricitabine (FTC); Lamivudine (3TC), Carbovir, Acyclovir, Interferon, Famciclovir, Penciclovir, Zidovudine (AZT), Didanosine (ddI), Zalcitabine (ddC), Stavudine (d4T), Tenofovir DF (Viread), Abacavir (ABC), L-(−)-FMAU, L-DDA phosphate prodrugs, and β-D-dioxolane nucleosides such as β-D-dioxolanyl-guanine (DG), β-D-dioxolanyl-2,6-diaminopurine (DAPD), and β-D-dioxolanyl-6-chloropurine (ACP); non-nucleoside RT inhibitors such as Nevirapine (Viramune), MKC-442, Efavirenz (Sustiva), Delavirdine (Rescriptor); protease inhibitors such as Amprenavir, Atazanavir, Fosamprenavir, Indinavir, Kaletra, Nelfinavir, Ritonavir, Saquinavir, AZT, DMP-450 and combination treatments such as Epzicom (ABC+3TC), Trizivir (ABC+3TC+AZT), and Truvada (FTC+Viread).

The compounds can also be used to treat equine infectious anemia virus (EIAV), feline immunodeficiency virus, and simian immunodeficiency virus. (Wang, S., Montelaro, R., Schinazi, R. F., Jagerski, B., and Mellors, J. W.: "Activity of nucleoside and non-nucleoside reverse transcriptase inhibitors (NNRTI) against equine infectious anemia virus (EIAV)." First National Conference on Human Retro viruses and Related Infections, Washington, D. C., Dec. 12-16, 1993; Sellon D. C., "Equine Infectious Anemia," Vet. Clin. North Am. Equine Pract. United States, 9: 321-336, 1993; Philpott, M. S., Ebner, J. P., Hoover, E. A., "Evaluation of 9-(2 phosphonylmethoxyethyl) adenine therapy for feline immunodeficiency virus using a quantitative polymerase chain reaction," Vet. Immunol. Immunopathol. 35:155166, 1992.)

Further, the carbocyclic nucleosides of the present invention can be effective against mutant strains of HIV, such as HIV-1 strains with mutations at the 184 codon of the reverse transcriptase region of the virus. Therefore, a method for treating HIV is provided that includes administering a carbocyclic nucleoside of the present invention, or its pharmaceutically acceptable salt or prodrug to a human in need of therapy in combination or alternation with a drug that induces a mutation in HIV-1 at the 184 codon or at a location other than the 184 codon of the reverse transcriptase region. This invention can be practiced by referring to published mutation patterns for known anti-HIV drugs, or by determining the mutation pattern for a new drug.

A method for using the carbocyclic nucleoside of the present invention as "salvage therapy" to patients which exhibit drug resistance to other anti-HIV agents is also provided. The carbocyclic nucleosides of the present invention can be used generally as salvage therapy for any patient which exhibits resistance to a drug that induces a mutation at the 184 codon or at a location other than the 184 codon.

Therefore, the invention disclosed herein also includes the following embodiments:

(i) A method for treating an HIV infection in a human comprising administering an effective amount of a carbocyclic nucleoside of the present invention or its pharmaceutically acceptable prodrug or salt to the human, optionally in a pharmaceutically acceptable carrier, in combination or alternation with a drug that induces a mutation in HIV-1 at a location other than the 184 codon of the reverse transcriptase region.

(ii) A method for treating an HIV infection in a human comprising administering an effective amount of a carbocyclic nucleoside of the present invention or its pharmaceutically acceptable salt to the human, optionally in a pharmaceutically acceptable carrier, in combination or alternation with a drug that induces a mutation in HIV-1 at codon 184 of the reverse transcriptase region.

The disclosed combination, alternation, or salvage regiments are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

DETAILED DESCRIPTION OF THE INVENTION

Figure 1:
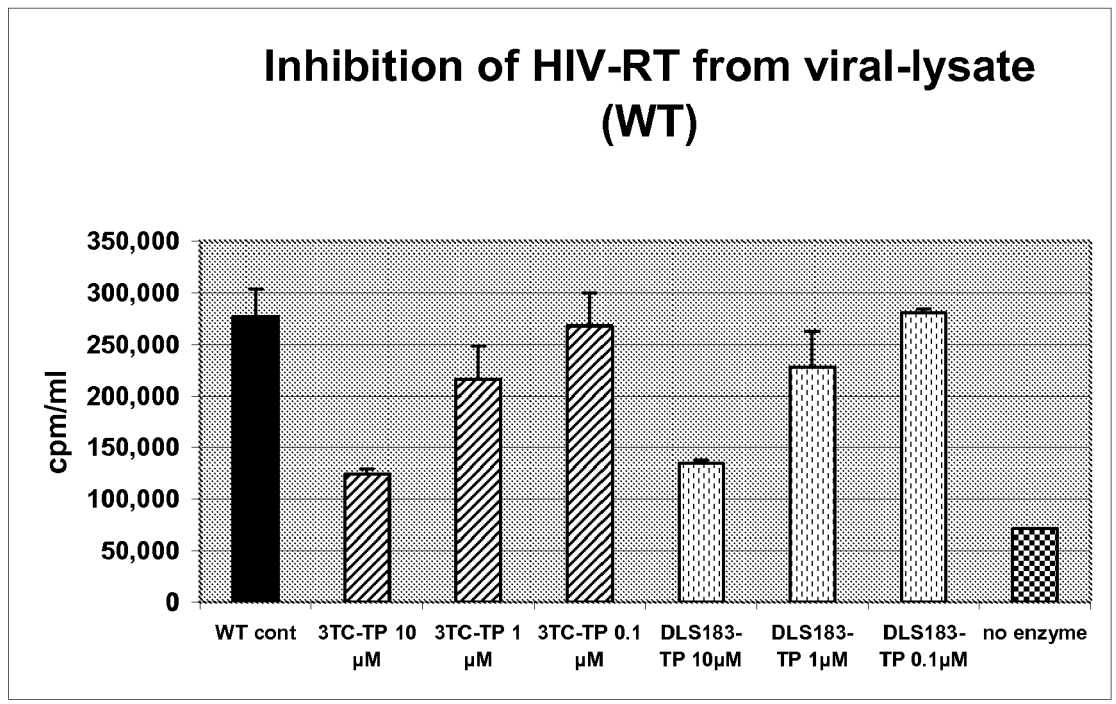
FIG. 1 is bar graphs depicting the inhibition of wild type HIV reverse transcriptase (RT) from viral lysate using a cyclobutyl nucleoside of the present invention, as compared to 3TC.

The present invention provides cyclobutyl nucleosides of formula (I)-(IV) or their pharmaceutically acceptable salts, esters, salts of esters, prodrugs, or salts of prodrugs, for the treatment of a host infected with a virus belonging to the Retroviridae (including HIV), Hepadnaviridae (including HBV), and/or Flaviviridae (including BVDV and HCV) family. Alternatively, the cyclobutyl nucleosides of formula (I)-(IV) or its pharmaceutically acceptable salt, ester, salt of ester, prodrug, or salt of prodrug, can be used for the treatment of abnormal cellular proliferation. Such nucleosides can be administered as its pharmaceutically acceptable derivative, including a compound which has been alkylated or acylated at the 3'-position or on the purine or pyrimidine, or a pharmaceutically acceptable salt thereof, optionally in a pharmaceutically acceptable carrier. In particular, the compounds of this invention either possess antiviral (i.e., anti-HIV-1, anti-HIV-2, or anti-hepatitis (B or C) activity, or antiproliferative activity, or are metabolized to a compound that exhibits such activity.

In summary, the present invention includes the following features:

(a) cyclobutyl nucleosides, as described herein, and pharmaceutically acceptable derivatives and salts thereof;

(b) cyclobutyl nucleosides, as described herein, and pharmaceutically acceptable derivatives and salts thereof for use in medical therapy, for example for the treatment or prophylaxis of a Retroviridae (including HIV), Hepadnaviridae (including HBV), and/or Flaviviridae (including BVDV and HCV) infection or for the treatment of abnormal cellular proliferation;

(c) use of these cyclobutyl nucleosides, as described herein, and pharmaceutically acceptable derivatives and salts thereof in the manufacture of a medicament for treatment of a Retroviridae (including HIV), Hepadnaviridae (including HBV), and/or Flaviviridae (including BVDV and HCV) infection or for the treatment of abnormal cellular proliferation;

(d) pharmaceutical formulations comprising the cyclobutyl nucleosides, as described herein, or a pharmaceutically acceptable derivative or salt thereof together with a pharmaceutically acceptable carrier or diluent; and (e) processes for the preparation of cyclobutyl nucleosides, as described herein, as described in more detail below.

In one embodiment, a method for the treatment or prophylaxis of a viral infection, including Retroviridae (including HIV), Hepadnaviridae (including HBV), and/or Flaviviridae (including BVDV and HCV) infection, and/or abnormal cellular proliferation that includes the administration of an antivirally or anti-proliferative effective amount of a nucleoside of the present invention, or its pharmaceutically acceptable salt or prodrug thereof is provided.

In another embodiment, a method for the treatment or prophylaxis of a Flaviviridae infection, such as an HCV infection, that includes the administration of an antivirally effective amount of a nucleoside of the present invention, or its pharmaceutically acceptable salt or prodrug thereof in the manufacture of a medicament for treatment is provided.

In another embodiment, a method for the treatment or prophylaxis of a Retroviridae infection, such as an HIV infection, that includes the administration of an antivirally effective amount of a nucleoside of the present invention, or its pharmaceutically acceptable salt or prodrug thereof in the manufacture of a medicament for treatment is provided.

In another embodiment, a method for the treatment or prophylaxis of a Hepadnaviridae infection, such as an HBV infection, that includes the administration of an antivirally effective amount of a nucleoside of the present invention, or its pharmaceutically acceptable salt or prodrug thereof in the manufacture of a medicament for treatment is provided.

In another embodiment, a method for the treatment or prophylaxis of a disease characterized by abnormal cellular proliferation that includes the administration of an anti-proliferative effective amount of a nucleoside of the present invention.

In another embodiment, the invention is the use of one of the compounds described herein in the manufacture of a medicament for the treatment of a viral infection or abnormal cellular proliferation, as provided herein.

In another embodiment, the invention is the use of one of the compounds described herein in the treatment of a host exhibiting a viral infection or abnormal cellular proliferation, as provided herein.

In another embodiment, a pharmaceutical composition that includes an antivirally or anti-proliferative effective amount of a nucleoside of the present invention, or its pharmaceutically acceptable salt or prodrug thereof together with a pharmaceutically acceptable carrier or diluent according to the present invention is provided.

In another embodiment, a pharmaceutical composition with a nucleoside of the present invention, or its pharmaceutically acceptable salt or prodrug thereof in combination with one or more other antivirally or anti-proliferative effective agents is provided.

In another embodiment, a process for the preparation of the nucleosides of the present invention, and its pharmaceutically acceptable salt and prodrug thereof is provided.

In an additional embodiment, a method of treating a mammal having a virus-associated disorder which comprises administering to the mammal a pharmaceutically effective amount of a nucleoside of the present invention, or their pharmaceutically acceptable salts or prodrugs thereof, is provided.

In an additional embodiment, a method of treating a mammal having disorder associated with abnormal cellular proliferation, which comprises administering to the mammal a pharmaceutically effective amount of a nucleoside of the present invention, or their pharmaceutically acceptable salts or prodrugs thereof, is provided.

In particular, the invention includes the described compounds in methods for treating or preventing, or uses for the treatment or prophylaxis of, or uses in the manufacture of a medicament for following:

(e) an Retroviridae infection, including an HIV infection;

(f) a Hepadnaviridae infection including hepatitis B virus (HBV) infection; and (g) a Flaviviridae infection, including all members of the Hepacivirus genus (HCV), Pestivirus genus (BVDV, CSFV, BDV), or Flavivirus genus (Dengue virus, Japanese encephalitis virus group (including West Nile Virus), and Yellow Fever virus);

(h) abnormal cellular proliferation, including psoriasis, eczema, atherosclerosis, asthma, arthritis, osteoprorosis, leukemia, and malignant tumors.

Compounds of the Invention

In one embodiment, the anti-virally or anti-proliferative effective nucleoside is a cyclobutyl nucleoside of the general formula (I)-(IV):

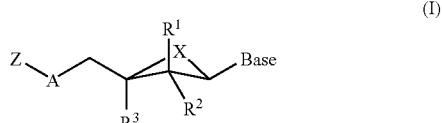

(I)

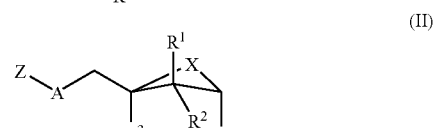

(II)

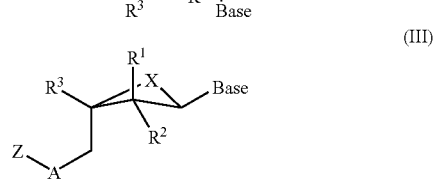

(III)

-continued

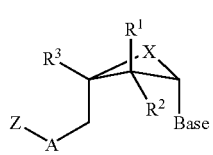
(IV)

or a pharmaceutically acceptable salt, ester, salt of an ester, prodrug, salt of a prodrug, enantiomer, diastereomer, or tautomer thereof, wherein;

Base is a purine or pyrimidine base;

Z is independently H; phosphate (including monophosphate, diphosphate, triphosphate, or a stabilized phosphate prodrug); $P(O)Z'Z''$, $CH_2P(O)Z'Z''$, acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein Z is independently H or phosphate; Z' and Z'' each independently is OH, OAlkyl, OAryl, alkyl, aryl, SH, SAlkyl, SAryl, $NH_2$, mono or di-alkylamino, mono- or di-arylamino, or a residue of an amino acid;

A is O, S, or $CH_2$; or alternatively

A can be a covalent bond when Z is $P(O)Z'Z''$ or $CH_2P(O)Z'Z''$;

$R_1$, $R_2$, and $R_3$ are independently hydrogen, lower alkyl ($C_1$, $C_2$, $C_3$, $C_4$, $C_5$, and $C_6$ alkyl), halogenated lower alkyl, $CF_3$, 2-Br-ethyl, lower alkenyl ($C_2$, $C_3$, $C_4$, $C_5$, and $C_6$ alkenyl), halogenated lower alkenyl, Br-vinyl, lower alkynyl ($C_2$, $C_3$, $C_4$, $C_5$, and $C_6$ alkenyl), halogenated lower alkynyl, halo (fluoro, chloro, bromo, iodo), cyano, azido, $NO_2$, $NH_2$, —NH(lower alkyl), NH(acyl), N(lower alkyl)$_2$, —N(acyl)$_2$, hydroxy, OZ, O(lower acyl), O(lower alkyl), O(alkenyl), C(O)O(alkyl), C(O)O(lower alkyl); or alternatively, $R_1$ and $R_2$ together are $=CH_2$ or $=CHY$; or alternatively $R_1$ and $R_2$ can come together to form a three-membered carbocyclic or heterocyclic ring, such as an epoxide ring; such that if $R_1$ is H, then $R_2$ is not $CH_2OH$, and if $R_2$ is H, then $R_1$ is not $CH_2OH$;

X is $CH_2$, CHY, or S; and

Y is H, methyl, halogenated methyl, $CF_3$, halogen (F, Cl, Br, or I), $N_3$, cyano, or $NO_2$.

In one embodiment of the invention, Z is not H. In another embodiment of the invention, $R_1$ and $R_2$ are not both H.

In one particular embodiment, the base is a pyrimidine. In a particular sub-embodiment, the pyrimidine is a 5-fluorocytidine.

In one particular embodiment, the base is a purine. In a particular sub-embodiment, the purine is guanine or adenine.

In another embodiment, the anti-virally or anti-proliferative effective nucleoside is a cyclobutyl nucleoside of the general formula (Ia)-(IVa):

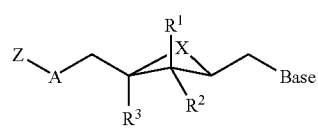
(Ia)

-continued

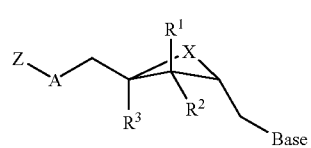
(IIa)

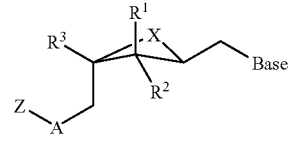
(IIIa)

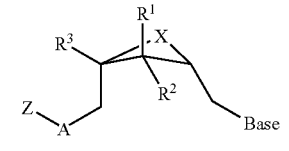
(IVa)

or a pharmaceutically acceptable salt, ester, salt of an ester, prodrug, salt of a prodrug, enantiomer, diastereomer, or tautomer thereof, wherein Z, Z', Z'', A, $R_1$, $R_2$, $R_3$, X, Base and Y are as defined above.

In another particular embodiment of the invention, the anti-virally or anti-proliferative effective nucleoside is:

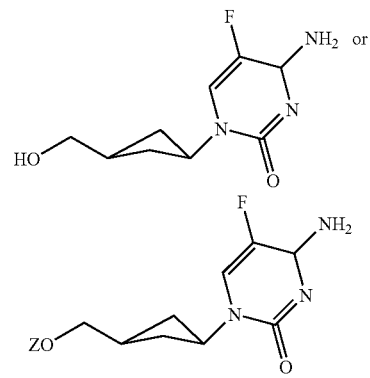

In one particular embodiment, the anti-virally or anti-proliferative effective nucleoside is selected from the group consisting of:

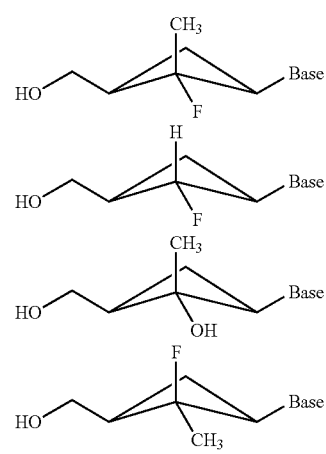

-continued

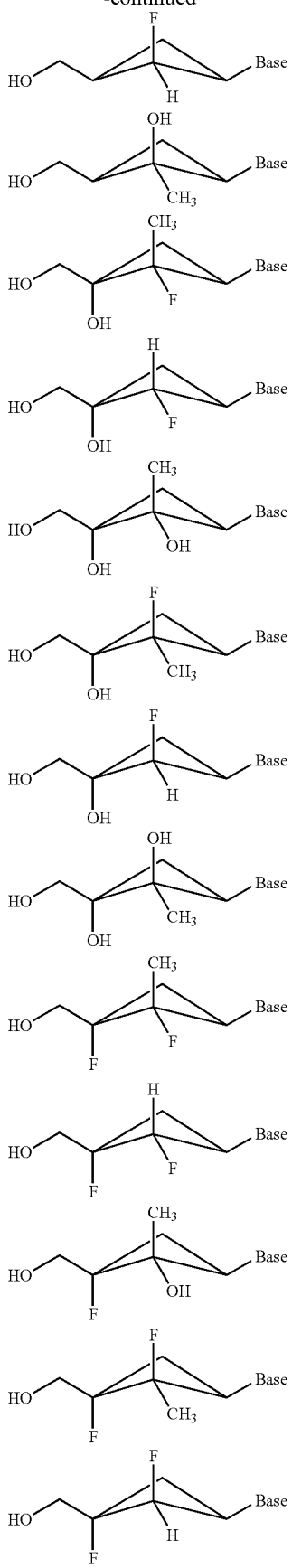

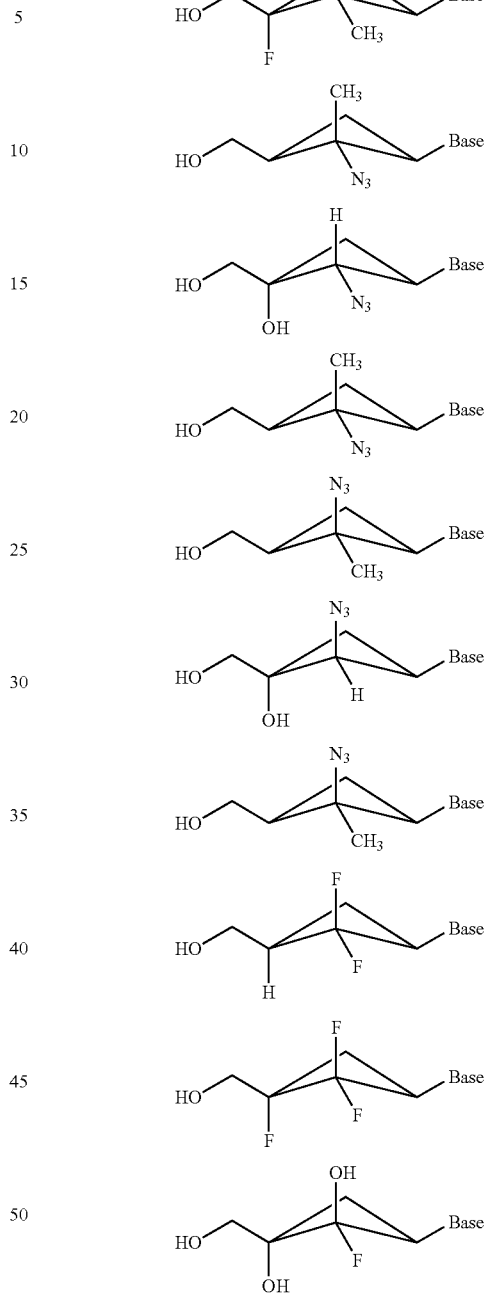

or a pharmaceutically acceptable salt, ester, salt of an ester, prodrug, salt of a prodrug, enantiomer, diastereomer, or tautomer thereof, wherein each OH can be substituted with OZ, wherein Z is as defined above.

In one particular embodiment, the base is a pyrimidine. In a particular sub-embodiment, the pyrimidine is a 5-fluorocytidine.

In one particular embodiment, the base is a purine. In a particular sub-embodiment, the purine is guanine or adenine.

In another embodiment, the anti-virally or anti-proliferative effective nucleoside is selected from the group consisting of:

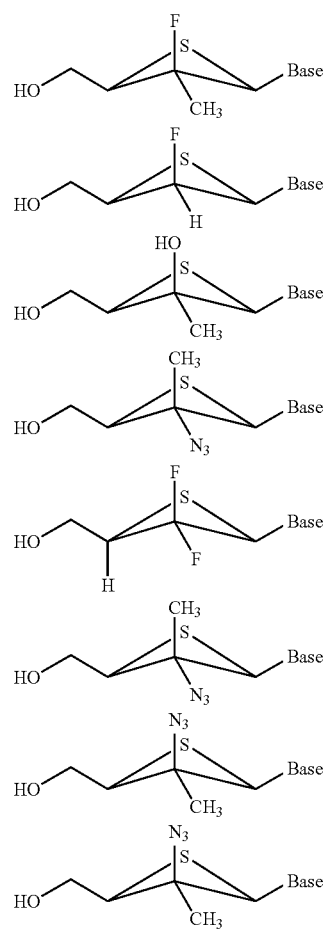

or a pharmaceutically acceptable salt, ester, salt of an ester, prodrug, salt of a prodrug, enantiomer, diastereomer, or tautomer thereof, wherein each OH can be substituted with OZ, wherein Z is as defined above.

In one particular embodiment, the base is a pyrimidine. In a particular sub-embodiment, the pyrimidine is a 5-fluorocytidine.

In one particular embodiment, the base is a purine. In a particular sub-embodiment, the purine is guanine or adenine.

In another embodiment, the anti-virally or anti-proliferative effective nucleoside is selected from the group consisting of:

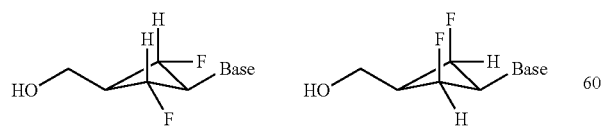

or a pharmaceutically acceptable salt, ester, salt of an ester, prodrug, salt of a prodrug, enantiomer, diastereomer, or tautomer thereof, wherein each OH can be substituted with OZ, wherein Z is as defined above.

In one particular embodiment, the base is a pyrimidine. In a particular sub-embodiment, the pyrimidine is a 5-fluorocytidine.

In one particular embodiment, the base is a purine. In a particular sub-embodiment, the purine is guanine or adenine.

In another embodiment, the anti-virally or anti-proliferative effective nucleoside is selected from the group consisting of:

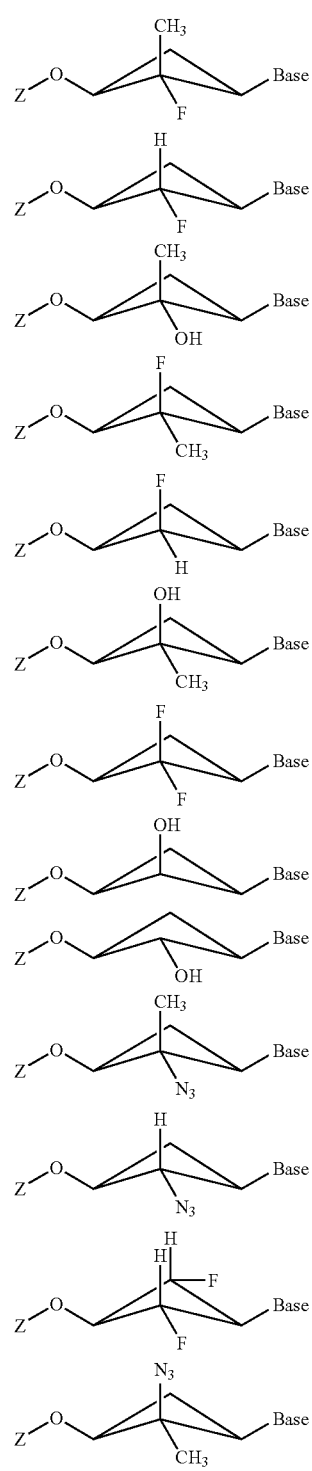

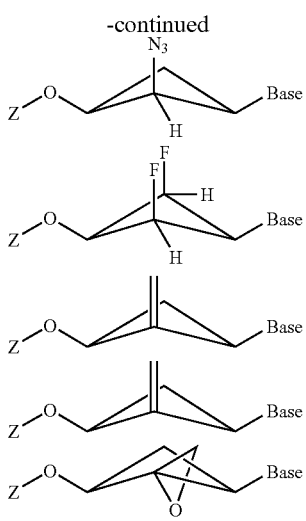

or a pharmaceutically acceptable salt, ester, salt of an ester, prodrug, salt of a prodrug, enantiomer, diastereomer, or tautomer thereof, wherein Z is as defined above.

In one particular embodiment, the base is a pyrimidine. In a particular sub-embodiment, the pyrimidine is a 5-fluorocytidine.

In one particular embodiment, the base is a purine. In a particular sub-embodiment, the purine is guanine or adenine.

In another embodiment, the nucleoside is any of the nucleosides disclosed herein, such as:

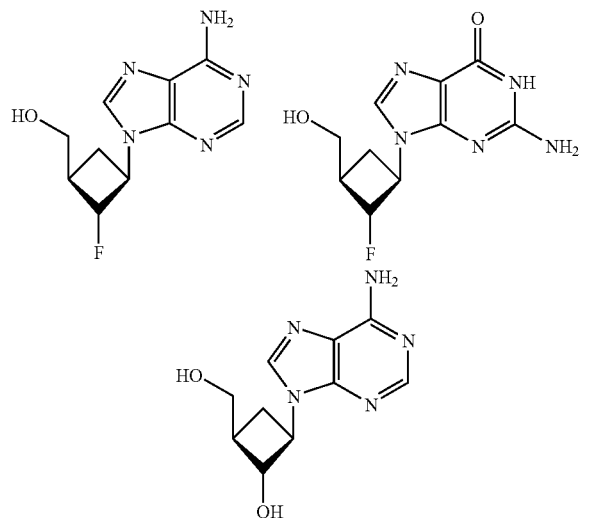

or a pharmaceutically acceptable salt, ester, salt of an ester, prodrug, salt of a prodrug, enantiomer, diastereomer, or tautomer thereof.

Stereoisomerism and Polymorphism

Compounds of the present invention having a chiral center may exist in and be isolated in optically active and racemic forms. Some compounds may exhibit polymorphism. The present invention encompasses racemic, optically-active, polymorphic, or stereoisomeric form, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution.

As shown below, a nucleoside contains at least two critical chiral carbon atoms (*). In general, the substituents on the chiral carbons [the specified purine or pyrimidine base (referred to as the 1'-substituent) and $CH_2OH$ (referred to as the 3'-substituent)] of the nucleoside can be either cis or β (on the same side) or trans or α (on opposite sides) with respect to the sugar ring system. Both the cis and trans racemates consist of a pair of optical isomers. Hence, each compound has four individual stereoisomers. The two cis enantiomers together are referred to as a racemic mixture of β-enantiomers, and the two trans enantiomers are referred to as a racemic mixture of α-enantiomers.

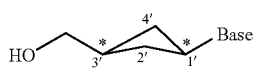

Nonlimiting Examples of Disorders that are Characterized by Abnormal Cellular Proliferation Examples of proliferative disorders other than neoplasms that can be treated with the cyclobutyl derivatives of the present invention are listed below, as well as any others listed or described in the Background of the Invention or otherwise in the specification.

TABLE 1

| Organ System | Disease/Pathology |
|---|---|
| Dermatological | Psoriasis (all forms), acne vulgaris, acne rosacea, common warts, anogenital (venereal) warts, eczema; lupus associated skin lesions; dermatitides such as seborrheic dermatitis and solar dermatitis; keratoses such as seborrheic keratosis, senile keratosis, actinic keratosis, photo-induced keratosis, skin ageing, including photo-induced skin aging, keratosis follicularis, keloids and Prophylaxis against keloid formation; leukoplakia, lichen, planus, keratitis, contact dermatitis, eczema, urticaria, pruritus, hidradenitis, acne inversa |

TABLE 1-continued

| Organ System | Disease/Pathology |
|---|---|
| Cardiovascular | Hypertension, vasculo-occlusive diseases including Atherosclerosis, thrombosis and restenosis after angioplasty; acute coronary syndromes such as unstable angina, myocardial infarction, ischemic and non-ischemic cardiomyopathies, post-MI cardiomyopathy and myocardial fibrosis, substance-induced cardiomyopathy. |
| Endocrine | Insulin resistant states including obesity, diabetes mellitus (types 1 & 2), diabetic retinopathy, macular degeneration associated with diabetes, gestational diabetes, impaired glucose tolerance, polycystic ovarian syndrome; osteoporosis, osteopenia, accelerated aging of tissues and organs including Werner's syndrome. |
| Urogenital | Endometriosis, benign prostatic hyperplasia, leiomyoma, Polycystic kidney disease, diabetic nephropathy. |
| Pulmonary | Asthma, chronic obstructive pulmonary disease (COPD), reactive Airway disease, pulmonary fibrosis, pulmonary hypertension. |
| Connective tissue/joints | Immunological Rheumatoid arthritis, Raynaud's phenomenon/disease, Sjogren's Syndrome systemic sclerosis, systemic lupus erythematosus, vasculitides, ankylosing spondylitis, osteoarthritis, reactive arthritis, psoriatic arthritis, fibromyalgia. |
| Other | Fibrocystic breast disease, fibroadenoma, chronic fatigue syndrome. |

Nonlimiting examples of neoplastic diseases or malignancies treatable with the a cyclobutyl derivatives of the present invention are listed below.

| Organ System | Malignancy/Cancer type |
|---|---|
| Skin | Basal cell carcinoma, melanoma, squamous cell carcinoma; cutaneous T cell lymphoma; Kaposi's sarcoma. |
| Hematological | Acute leukemia, chronic leukemia and myelodysplastic syndromes. |
| Urogenital | Prostatic, renal and bladder carcinomas, anogenital carcinomas including cervical, ovarian, uterine, vulvar, vaginal, and those associated with human papilloma virus infection. |
| Neurological | Gliomas including glioblastomas, astrocytoma, ependymoma, medulloblastoma, oligodendroma; meningioma, pituitary adenoma, neuroblastoma, craniopharyngioma. |
| Gastrointestinal | Colon, colorectal, gastric, esophageal, mucocutaneous carcinomas. |
| Breast | Breast cancer including estrogen receptor and progesterone Receptor positive or negative subtypes, soft tissue tumors. |
| Metastasis | Metastases resulting from the neoplasms. |
| Other | Angiomata, angiogenesis associated with the neoplasms. |

Definitions

The term "alkyl," as used herein, unless otherwise specified, refers to a saturated straight, branched, or cyclic, primary, secondary, or tertiary hydrocarbon, including but not limited to those of C1 to C16, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, azido, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "lower alkyl," as used herein, and unless otherwise specified, refers to a C1 to C6 saturated straight, branched, or if appropriate, a cyclic (for example, cyclopropyl) alkyl group, including both substituted and unsubstituted forms.

The term "alkylene" or "alkenyl" refers to a saturated hydrocarbyldiyl radical of straight or branched configuration, including but not limited to those that have from one to ten carbon atoms. Included within the scope of this term are methylene, 1,2-ethane-diyl, 1,1-ethane-diyl, 1,3-propane-diyl, 1,2 propane-diyl, 1,3-butane-diyl, 1,4-butane-diyl and the like. The alkylene group or other divalent moiety disclosed herein can be optionally substituted with one or more moieties selected from the group consisting of alkyl, halo, haloalkyl, hydroxyl, carboxyl, acyl, acyloxy, amino, amido, carboxyl derivatives, alkylamino, azido, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "aryl," as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of bromo, chloro, fluoro, iodo, hydroxyl, azido, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991.

The term "aralkyl," as used herein, and unless otherwise specified, refers to an aryl group as defined above linked to the molecule through an alkyl group as defined above. The term "alkaryl" or "alkylaryl" as used herein, and unless otherwise specified, refers to an alkyl group as defined above linked to the molecule through an aryl group as defined above. In each of these groups, the alkyl group can be optionally substituted as describe above and the aryl group can be optionally substituted with one or more moieties selected from the group consisting of alkyl, halo, haloalkyl, hydroxyl, carboxyl, acyl, acyloxy, amino, amido, azido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., Protective Groups in Organic Synthesis, John Wiley and Sons, Second Edition, 1991, hereby incorporated by reference. Specifically included within the scope of the term aryl are phenyl; naphthyl; phenylmethyl; phenylethyl; 3,4,5-trihydroxyphenyl; 3,4,5-trimethoxyphenyl; 3,4,5-triethoxy-phenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4tbutylphenyl; 4-t-butylphenylmethyl and the like.

The term "alkylamino" or "arylamino" refers to an amino group that has one or two alkyl or aryl substituents, respectively.

The term "halogen," as used herein, includes fluorine, chlorine, bromine and iodine.

The term purine or pyrimidine base includes, but is not limited to, adenine, N6-alkylpurines, N6-acylpurines (wherein acyl is C(O)(alkyl, aryl, alkylaryl, or arylalkyl), N6-benzylpurine, N6-halopurine, N6-vinylpurine, N6-acetylenic purine, N6-acyl purine, N6 hydroxyalkyl purine, N6-thioalkyl purine, N2-alkylpurines, N2-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5 fluorouracil, C5-alkylpyrimidines, C5-benzylpyrimidines, C5-halopyrimidines, C5 vinylpyrimidine, C5-acetylenic pyrimidine, C5-acyl pyrimidine, C5-hydroxyalkyl purine, C5-amidopyrimidine, C5-cyanopyrimidine, C5-nitropyrimidine, C5 aminopyrimidine, N2-alkylpurines, N2-alkyl-6-thiopurines, 5-azacytidinyl, 5-azauracilyl, triazolopyridinyl, imidazolopyridinyl, pyrrolopyrimidinyl, and pyrazolo-pyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl and t-butyldiphenylsilyl, trityl, alkyl groups, and acyl groups such as acetyl and propionyl, methanesulfonyl, and p-toluenesulfonyl. Alternatively, the purine or pyrimidine base can optionally substituted such that it forms a viable prodrug, which can be cleaved in vivo. Examples of appropriate substituents include acyl moiety, an amine or cyclopropyl (e.g., 2-amino, 2,6-diamino or cyclopropyl guanosine).

The term "enantiomerically enriched" is used throughout the specification to describe a nucleoside which includes at least about 95%, preferably at least 96%, more preferably at least 97%, even more preferably, at least 98%, and even more preferably at least about 99% or more of a single enantiomer of that nucleoside. When a nucleoside of a particular configuration (D or L) is referred to in this specification, it is presumed that the nucleoside is an enantiomerically enriched nucleoside, unless otherwise stated. As used herein, the term "resistant virus" refers to a virus that exhibits a three, and more typically, five or greater fold increase in EC50 compared to naive virus in a constant cell line, including, but not limited to peripheral blood mononuclear cells (PBMCs), or MT2 or MT4 cells.

As used herein, the term "substantially pure" or "substantially in the form of one optical isomer" refers to a nucleoside composition that includes at least 95% to 98%, or more, preferably 99% to 100%, of a single enantiomer of that nucleoside. In a preferred embodiment, the cyclobutyl nucleoside is administered in substantially pure form for any of the disclosed indications.

The abbreviations of amino acids used herein are described in Table 2.

The term "host," as used herein, refers to a unicellular or multicellular organism in which the virus can replicate, including cell lines and animals, and preferably a human. Alternatively, the host can be carrying a part of the viral genome, whose replication or function can be altered by the compounds of the present invention. The term host specifically refers to infected cells, cells transfected with all or part of the viral genome and animals, in particular, primates (including chimpanzees) and humans. Relative to abnormal cellular proliferation, the term "host" refers to unicellular or multicellular organism in which abnormal cellular proliferation can be mimicked. The term host specifically refers to cells that abnormally proliferate, either from natural or unnatural causes (for example, from genetic mutation or genetic engineering, respectively), and animals, in particular, primates (including chimpanzees) and humans. In most animal applications of the present invention, the host is a human patient. Veterinary applications, in certain indications, however, are clearly anticipated by the present invention (such as bovine viral diarrhea virus in cattle, hog cholera virus in pigs, and border disease virus in sheep).

Pharmaceutically Acceptable Salts and Prodrugs

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, Antiviral Research, 27 (1995) 1-17. Any of these can be used in combination with the disclosed nucleosides to achieve a desired effect.

The active nucleoside can also be provided as a 3'-phosphoether lipid or a 3'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." AIDS Res. Hum. Retro Viruses. 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." J. Med. Chem. 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine." Antimicrob. Agents Chemother. 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." J. Biol. Chem. 265:61127.

Nonlimiting examples of U.S. patents that disclose suitable lipophilic substituents that can be covalently incorporated into the nucleoside, preferably at the 3'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Nonlimiting examples of nucleotide prodrugs are described in the following references: Ho, D. H. W. (1973) "Distribution of Kinase and deaminase of 1β-D-arabinofuranosylcytosine in tissues of man and muse." Cancer Res. 33, 2816-2820; Holy, A. (1993) Isopolar phosphorous-modified nucleotide analogues," In: De Clercq (Ed.), Advances in Antiviral Drug Design, Vol. I, JAI Press, pp. 179-231; Hong, C. I., Nechaev, A., and West, C. R. (1979a) "Synthesis and antitumor activity of 1-β3-D-arabino-furanosylcytosine conjugates of cortisol and cortisone." Bicohem. Biophys. Rs. Commun. 88, 1223-1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(β-D-arabinofuranosyl) cytosine conjugates of corticosteriods and selected lipophilic alcohols." J. Med. Chem. 28, 171-177; Hosteller, K. Y., Stuhmiller, L. M., Lenting, H. B. M. van den Bosch, H. and Richman J. Biol. Chem. 265, 6112-6117; Hosteller, K. Y., Carson, D. A. and Richman, D. D. (1991); "Phosphatidylazidothymidine: mechanism of antiretroviral action in CEM cells." J. Biol. Chem. 266, 11714-11717; Hosteller, K. Y., Korba, B. Sridhar, C., Gardener, M. (1994a) "Antiviral activity of phosphatidyldideoxycytidine in hepatitis B-infected cells and enhanced hepatic uptake in mice." Antiviral Res. 24, 59-67; Hosteller, K. Y., Richman, D. D., Sridhar. C. N. Felgner, P. L. Felgner, J., Ricci, J., Gardener, M. F. Selleseth, D. W. and Ellis, M. N. (1994b) "Phosphatidylazidothymidine and phosphatidyldC: Assessment of uptake in mouse lymphoid tissues and antiviral activities in human immunodeficiency virus-infected cells and in rauscher leukemia virus-infected mice." Antimicrobial Agents Chemother. 38, 2792-2797; Hunston, R. N., Jones, A. A. McGuigan, C., Walker, R. T., Balzarini, J., and DeClercq, E. (1984) "Synthesis and biological properties of some cyclic phosphotriesters derived from 2'-deoxy-5-fluorouridine." J. Med. Chem. 27, 440-444; Ji, Y. H., Moog, C., Schmitt, G., Bischoff, P. and Luu, B. (1990); "Monophosphoric acid esters of 7-β-hydroxycholesterol and of pyrimidine nucleoside as potential antitumor agents: synthesis and preliminary evaluation of antitumor activity." J. Med. Chem. 33 2264-2270; Jones, A. S., McGuigan, C., Walker, R. T., Balzarini, J. and DeClercq, E. (1984) "Synthesis, properties, and biological activity of some nucleoside cyclic phosphoramidates." J. Chem. Soc. Perkin Trans. I, 1471-1474; Juodka, B. A. and Smrt, J. (1974) "Synthesis of diribonucleoside phosph (P□N) amino acid derivatives." Coll. Czech. Chem. Comm. 39, 363-968; Kataoka, S., Imai, J., Yamaji, N., Kato, M., Saito, M., Kawada, T. and Imai, S. (1989) "Alkylated cAMP derivatives; selective synthesis and biological activities." Nucleic Acids Res. Sym. Ser. 21, 1-2; Kataoka, S., Uchida, "(cAMP) benzyl and methyl triesters." Heterocycles 32, 1351-1356; Kinchington, D., Harvey, J. J., O'Connor, T.

J., Jones, B. C. N. M., Devine, K. G., Taylor-Robinson D., Jeffries, D. J. and McGuigan, C. (1992) "Comparison of antiviral effects of zidovudine phosphoramidate an dphosphorodiamidate derivates against HIV and ULV in vitro." Antiviral Chem. Chemother. 3, 107-112; Kodama, K., Morozumi, M., Saithoh, K. I., Kuninaka, H., Yosino, H. and Saneyoshi, M. (1989) "Antitumor activity and pharmacology of 1-β-D-arabinofuranosylcytosine-5'-stearylphosphate; an orally active derivative of 1-β-D-arabinofuranosylcytosine." Jpn. J. Cancer Res. 80, 679-685; Korty, M. and Engels, J. (1979) "The effects of adenosine- and guanosine 3',5' phosphoric and acid benzyl esters on guinea-pig ventricular myocardium." Naunyn-Schmiedeberg's Arch. Pharmacol. 310, 103-111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." J. Med. Chem., 33, 2368-2375; LeBec, C., and Huynh-Dinh, T. (1991) "Synthesis of lipophilic phosphate triester derivatives of 5-fluorouridine an arabinocytidine as anticancer prodrugs." Tetrahedron Lett. 32, 6553-6556; Lichtenstein, J., Barner, H. D. and Cohen, S. S. (1960) "The metabolism of exogenously supplied nucleotides by *Escherichia coli*." J. Biol. Chem. 235, 457-465; Luethy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". Mitt. Geg. Lebensmittelunters. Hyg. 72, 131-133 (Chem. Abstr. 95, 127093); McGigan, C. Tollerfield, S. M. and Riley, P.a. (1989) "Synthesis and biological evaluation of some phosphate triester derivatives of the anti-viral drug Ara." Nucleic Acids Res. 17, 6065-6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." Antiviral Chem. Chemother. 1 107-113; McGuigan, C., O'Connor, T. J., Nicholls, S. R. Nickson, C. and Kinchington, D. (1990b) "Synthesis and anti-HIV activity of some novel substituted dialkyl phosphate derivatives of AZT and ddCyd." Antiviral Chem. Chemother. 1, 355-360; McGuigan, C., Nicholls, S. R., O'Connor, T. J., and Kinchington, D. (1990c) "Synthesis of some novel dialkyl phosphate derivative of 3'-modified nucleosides as potential anti-AIDS drugs." Antiviral Chem. Chemother. 1, 25-33; McGuigan, C., Devin, K. G., O'Connor, T. J., and Kinchington, D. (1991) "Synthesis and anti-HIV activity of some haloalkyl phosphoramidate derivatives of 3'-azido-3'-deoxythylmidine (AZT); potent activity of the trichloroethyl methoxyalaninyl compound." Antiviral Res. 15, 255-263; McGuigan, C., Pathirana, R. N., Balzarini, J. and DeClercq, E. (1993b) "Intracellular delivery of bioactive AZT nucleotides by aryl phosphate derivatives of AZT." J. Med. Chem. 36, 1048-1052.

Alkyl hydrogen phosphate derivatives of the anti-HIV agent AZT may be less toxic than the parent nucleoside analogue. Antiviral Chem. Chemother. 5, 271-277; Meyer, R. B., Jr., Shuman, D. A. and Robins, R. K. (1973) "Synthesis of purine nucleoside 3',5'-cyclic phosphoramidates." Tetrahedron Lett. 269-272; Nagyvary, J. Gohil, R. N., Kirchner, C. R. and Stevens, J. D. (1973) "Studies on neutral esters of cyclic AMP," Biochem. Biophys. Res. Commun. 55, 1072-1077; Namane, A. Gouyette, C., Fillion, M. P., Fillion, G. and Huynh-Dinh, T. (1992) "Improved brain delivery of AZT using a glycosyl phosphotriester prodrug." J. Med. Chem. 35, 3039-3044; Nargeot, J. Nerbonne, J. M. Engels, J. and Leser, H. A. (1983) Natl. Acad. Sci. U.S.A. 80, 2395-2399; Nelson, K. A., Bentrude, W. G. Stser, W. N. and Hutchinson, J. P. (1987) "The question of chair-twist equilibria for the phosphate rings of nucleoside cyclic 3', 5' monophosphates. $^1$HNMR and x-ray crystallographic study of the diastereomers of thymidine phenyl cyclic 3',5'-monophosphate." J. Am. Chem. Soc. 109, 4058-4064; Nerbonne, J. M., Richard, S., Nargeot, J. and Lester, H. A. (1984) "New photoactivatable cyclic nucleotides produce intracellular jumps in cyclic AMP and cyclic GMP concentrations." Nature 301, 74-76; Neumann, J. M., Herv, M., Debouzy, J. C., Guerra, F. I., Gouyette, C., Dupraz, B. and Huyny-Dinh, T. (1989) "Synthesis and transmembrane transport studies by NMR of a glucosyl phospholipid of thymidine." J. Am. Chem. Soc. 111, 4270-4277; Ohno, R., Tatsumi, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, I., Yamada, K. and Kimura, J. (1991) "Treatment of myelodysplastic syndromes with orally administered 1-β-D-arabinouranosylcytosine-5' stearylphosphate." Oncology 48, 451-455. Palomino, E., Kessle, D. and Horwitz, J. P. (1989) "A dihydropyridine carrier system for sustained delivery of 2', 3' dideoxynucleosides to the brain." J. Med. Chem. 32, 22-625; Perkins, R. M., Barney, S. Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) "Activity of BRL47923 and its oral prodrug, SB203657A against a rauscher murine leukemia virus infection in mice." Antiviral Res. 20 (Suppl. I). 84; Piantadosi, C., Marasco, C. J., Jr., Norris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) "Synthesis and evaluation of novel ether lipid nucleoside conjugates for anti-HIV-1 activity." J. Med. Chem. 34, 1408-1414; Pompon, A., Lefebvre, I., Imbach, J. L., Kahn, S. and Farquhar, D. (1994). "Decomposition pathways of the mono- and bis(pivaloyloxymethyl) esters of azidothymidine-5'-monophosphate in cell extract and in tissue culture medium; an application of the 'on-line ISRP-cleaning HPLC technique." Antiviral Chem. Chemother. 5, 91-98; Postemark, T. (1974) "Cyclic AMP and cyclic GMP." Annu. Rev. Pharmacol. 14, 23-33; Prisbe, E. J., Martin, J. C. M., McGhee, D. P. C., Barker, M. F., Smee, D. F. Duke, A. E., Matthews, T. R. and Verheyden, J. P. J. (1986) "Synthesis and antiherpes virus activity of phosphate an phosphonate derivatives of 9-[(1,3-dihydroxy-2-propoxy)methyl] guanine." J. Med. Chem. 29, 671-675; Pucch, F., Gosselin, G., Lefebvre, I., Pompon, a., Aubertin, A. M. Dim, and Imbach, J. L. (1993) "Intracellular delivery of nucleoside monophosphate through a reductase-mediated activation process." Antivral Res. 22, 155-174; Pugaeva, V. P., Klochkeva, S. I., Mashbits, F. D. and Eizengart, R. S. (1969). "Toxicological assessment and health standard ratings for ethylene sulfide in the industrial atmosphere." Gig. Trf. Prof. Zabol. 14, 47-48 (Chem. Abstr. 72, 212); Robins, R. K. (1984) "The potential of nucleotide analogs as inhibitors of Retro viruses and tumors." Pharm. Res. 11-18; Rosowsky, A., Kim. S. H., Ross and J. Wick, M. M. (1982) "Lipophilic 5'-(alkylphosphate) esters of 1-O-D-arabinofuranosylcytosine and its N4-acyl and 2.2'-anhydro-3'0-acyl derivatives as potential prodrugs." J. Med. Chem. 25, 171-178; Ross, W. (1961) "Increased sensitivity of the walker turnout towards aromatic nitrogen mustards carrying basic side chains following glucose pretreatment." Biochem. Pharm. 8, 235-240; Ryu, E. K., Ross, R. J. Matsushita, T., MacCoss, M., Hong, C. I. and West, C. R. (1982). "Phospholipid-nucleoside conjugates. 3. Synthesis and preliminary biological evaluation of 1-β-D-arabinofuranosylcytosine 5' diphosphate [−], 2-diacylglycerols." J. Med. Chem. 25, 1322-1329; Saffhill, R. and Hume, W. J. (1986) "The degradation of 5-iododeoxyuridine and 5-bromoethoxyuridine by serum from different sources and its consequences for the use of these compounds for incorporation into DNA." Chem. Biol. Interact. 57, 347-355; Saneyoshi, M., Morozumi, M., Kodama, K., Machida, J., Kuninaka, A. and Yoshino, H. (1980) "Synthetic nucleosides and nucleotides. XVI. Synthesis and biological evaluations of a series of 1-O-D-arabinofuranosylcytosine 5'-alky or arylphosphates." Chem. Pharm. Bull. 28, 2915-2923; Sastry, J. K., Nehete, P. N., Khan, S., Nowak, B. J., Plunkett, W., Arlinghaus, R. B. and Farquhar, D. (1992) "Membrane-permeable dideoxyuridine 5'-monophosphate analogue inhibits human immunodeficiency virus infection." Mol. Pharmacol. 41, 441-445; Shaw, J. P., Jones, R. J. Arimilli, M. N., Louie, M. S., Lee, W. A. and Cundy, K. C. (1994) "Oral bioavailability of PMEA from PMEA prodrugs in male Sprague-Dawley rats." 9th Annual AAPS Meeting. San Diego, Calif. (Abstract). Shuto, S., Ueda, S., Imamura, S., Fukukawa, K. Matsuda, A. and Ueda, T. (1987) "A facile one-step synthesis of 5' phosphatidylnucleosides by an enzymatic two-phase reaction." Tetrahedron Lett. 28, 199-202; Shuto, S. Itoh, H., Ueda, S., Imamura, S., Kukukawa, K., Tsujino, M., Matsuda, A. and Ueda, T. (1988) Pharm. Bull. 36, 209-217. An example of a useful phosphate prodrug group is the S-acyl-2-thioethyl group, also referred to as "SATE".

Combination or Alternation HIV and/or HBV Agents

It has been recognized that drug-resistant variants of viruses, such as HIV, HBV and HCV, can emerge after prolonged treatment with an antiviral agent. Drug resistance most typically occurs by mutation of a gene that encodes for an enzyme used in viral replication, for example, in the case of HIV, reverse transcriptase, protease, or DNA polymerase, and in the case of HBV, DNA polymerase. It has been demonstrated that the efficacy of a drug against HIV or HBV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor. A list compiling resistance data collected in vitro and in vivo for a number of antiviral compounds is found in Schinazi, et al, Mutations in retroviral genes associated with drug resistance, International Antiviral News, 1997.

Preferred compounds for combination or alternation therapy for the treatment of HBV include DNA polymerase inhibitors. In one embodiment of the invention, the additional anti-HBV agent is selected from the group consisting of 3TC, FTC, L-FMAU, interferon, β-D-dioxolanyl-guanine (DXG), β-D-dioxolanyl-2,6-diaminopurine (DAPD), and β-D-dioxolanyl-6-chloropurine (ACP), famciclovir, penciclovir, BMS-200475, bis pom PMEA (adefovir, dipivoxil); lobucavir, ganciclovir, ribavirin, and mixtures thereof.

Preferred protease inhibitors include crixivan (Merck), nelfinavir (Agouron), ritonavir (Abbott), saquinavir (Roche), DMP-266 (Sustiva) and DMP-450 (DuPont Merck).

Preferred examples of antiviral agents that can be used in combination or alternation with the compounds disclosed herein for HIV therapy include Emtricitabine (FTC); Lamivudine (3TC), Carbovir, Acyclovir, Interferon, Famciclovir, Penciclovir, Zidovudine (AZT), Didanosine (ddI), Zalcitabine (ddC), Stavudine (d4T), Tenofovir DF (Viread), Abacavir (ABC), L-(−)-FMAU, L-DDA phosphate prodrugs, and β-D-dioxolane nucleosides such as β-D-dioxolanyl-guanine (DG), β-D-dioxolanyl-2,6-diaminopurine (DAPD), and β-D-dioxolanyl-6-chloropurine (ACP); non-nucleoside RT inhibitors such as Nevirapine (Viramune), MKC-442, Efavirenz (Sustiva), Delavirdine (Rescriptor); protease inhibitors such as Amprenavir, Atazanavir, Fosamprenavir, Indinavir, Kaletra, Nelfinavir, Ritonavir, Saquinavir, AZT, DMP-450 and combination treatments such as Epzicom (ABC+3TC), Trizivir (ABC+3TC+AZT), and Truvada (FTC+Viread).

A more comprehensive list of compounds that can be administered in combination or alternation with any of the disclosed nucleosides include (1S,4R)-4-[2-amino-6-cyclopropyl-amino)-9H-purin-9-yl]-2-cyclopentene-1-methanol succinate ("1592", a carbovir analog; GlaxoWellcome); 3TC: (−)-β-L-2',3'-dideoxy-3'-thiacytidine (GlaxoWellcome); a-APA R18893: a-nitro-anilino-phenylacetamide; A-77003; C2 symmetry-based protease inhibitor (Abbott); A-75925: C2 symmetry-based protease inhibitor (Abbott); AAP-BHAP: bisheteroarylpiperazine analog (Upjohn); ABT-538: C2 symmetry-based protease inhibitor (Abbott); AzddU:3'-azido-2',3'-dideoxyuridine; AZT: 3'-azido-3'-deoxythymidine (GlaxoWellcome); AZT-p-ddI: 3'-azido-3'-deoxythymidilyl-(5',5')-2',3'-dideoxyinosinic acid (Ivax); BHAP: bisheteroarylpiperazine; BILA 1906: N-{1S-[[[3-[2S-{(1,1-dimethylethyl)amino]-carbonyl}-4R-]3-pyridinylmethyl) thio]-1-piperidinyl]-2R-hydroxy-1S-(phenylmethyl)-propyl]amino]carbonyl]-2-methylpropyl}-2-quinolinecarboxamide (Bio Mega/Boehringer-Ingelheim); BILA 2185: N-(1,1-dimethylethyl)-1-[2S-[[2-2,6-dimethylphenoxy)-1-oxoethyl]amino]-2R-hydroxy-4-phenylbutyl]-4R-pyridinylthio)-2-piperidine-carboxamide (BioMega/Boehringer-Ingelheim); BM+51.0836: thiazolo-isoindolinone derivative; BMS 186,318: aminodiol derivative HIV-1 protease inhibitor (Bristol-Myers-Squibb); d4API: 9-[2,5-dihydro-5-(phosphonomethoxy)-2-furanel]adenine (Gilead); d4C: 2',3'-didehydro-2',3'-dideoxycytidine; d4T: 2',3'-didehydro-3'-deoxythymidine (Bristol-Myers-Squibb); ddC; 2',3'-dideoxycytidine (Roche); ddI: 2',3'-dideoxyinosine (Bristol-Myers-Squibb); DMP-266: a 1,4-dihydro-2H-3,1-benzoxazin-2-one; DMP-450: {[4R-(4-a,5-a,6-b,7-b)]-hexahydro-5,6-bis(hydroxy)-1,3-bis(3-amino)phenyl]-methyl)-4,7-bis(phenylmethyl)-2H-1,3-diazepin-2-one}-bismesylate (Avid); DXG:(−)-β-D-dioxolane-guanosine (Gilead); EBU-dM:5-ethyl-1-ethoxymethyl-6-(3,5-dimethyl-benzyl)uracil; E-EBU: 5-ethyl-1-ethoxymethyl-6-benzyluracil; DS: dextran sulfate; E-EPSeU:1-(ethoxymethyl)-(6-phenylselenyl)-5-ethyluracil; E-EPU: 1-(ethoxymethyl)-(6-phenyl-thio)-5-ethyluracil; FTC:β-2',3'-dideoxy-5-fluoro-3'-thiacytidine (Gilead); HBY097:S-4-isopropoxycarbonyl-6-methoxy-3-(methylthio-methyl)-3,4-dihydro-quinoxalin-2(1H)-thione; HEPT: 1-[(2-hydroxyethoxy)methyl]-6-(phenylthio)thymine; HIV-1: human immunodeficiency virus type 1; JM2763: 1,1'-(1,3-propanediyl)-bis-1,4,8,11-tetraazacyclotetradecane (Johnson Matthey); JM3100:1,1'-[1,4-phenylenebis-(methylene)]-bis-1,4,8,11-tetraaza-cyclotetradecane (Johnson Matthey); KNI-272: (2S,3S)-3-amino-2-hydroxy-4-phenyl-butyric acid-containing tripeptide; L-697,593; 5-ethyl-6-methyl-3-(2-phthalimido-ethyl)pyridin-2(1H)-one; L-735,524: hydroxy-amino-pentane amide HIV-1 protease inhibitor (Merck); L-697,661: 3-{[(-4,7-dichloro-1,3-benzoxazol-2-yl)methyl]amino}-5-ethyl-6-methylpyridin-2(1H)-one; L-FDDC: (−)-β-L-5-fluoro-2',3'-dideoxy-cytidine; L-FDOC: (−)-β-L-5-fluoro-dioxolane cytosine; MKC442: 6-benzyl-1-ethoxymethyl-5-isopropyluracil (1-EBU; Triangle/Mitsubishi); Nevirapine:11-cyclopropyl-5,11-dihydro-4-methyl-6H-dipyridol[3,2-b:2',3'-e]diazepin-6-one (Boehringer-Ingelheim); NSC648400:1-benzyloxymethyl-5-ethyl-6-(alpha-pyridylthio)uracil (E-BPTU); P9941: [2-pyridylacetyl-IlePheAla-y(CHOH)]2 (Dupont Merck); PFA: phosphonoformate (foscamet; Astra); PMEA: 9-(2-phosphonylmethoxyethyl)adenine (Gilead); PMPA: (R)-9-(2-phosphonyl-methoxypropyl)adenine (Gilead); Ro 31-8959: hydroxyethylamine derivative HIV-1 protease inhibitor (Roche); RPI-312: peptidyl protease inhibitor, 1-[(3s)-3-(n-alpha-benzyloxycarbonyl)-1-asparginyl)-amino-2-hydroxy-4-phenyl-butyryl]-n-tert-butyl-1-proline amide; 2720: 6-chloro-3,3-dimethyl-4-(isopropenyl-oxycarbonyl)-3,4-dihydro-quinoxalin-2(1H)thione; SC-52151: hydroxyethylurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)-imidazo[4,5,1-jk][1,4]-benzo-diazepin-2(1H)-thione (Janssen); TIBO 82913: (+)-(5S)-4,5,6,7,-tetrahydro-9-chloro-5-methyl-6-(3-methyl-2-butenyl)-imidazo-[4,5,1jk]-[1,4]benzo-diazepin-2(1H)-thione (Janssen); TSAO-m3 T: [2',5'-bis-O-(tert-butyl-dimethylsilyl)-3'-spiro-5'-(4'-amino-1',2'-oxathiole-2',2'-dioxide)]-b-D-pentofuranosyl-N-3-methyl-thymine; U90152:1-[3-[(1-methylethyl)-amino]-2-pyridinyl]-4-[[5-[(methyl-sulphonyl)-amino]-1H-indol-2-yl]carbonyl]-piperazine; UC: thiocarboxanilide derivatives (Uniroyal); UC-781: N-[4-chloro-3-(3-methyl-2-butenyloxy)phenyl]-2-methyl-3-furan-carbothio-amide; UC-82: N-[4-chloro-3-(3-methyl-2-butenyloxy)phenyl]-2-methyl-3-thiophene-carbothioamide; VB 11,328: hydroxyethyl-sulphonamide protease inhibitor (Vertex); VX-478:hydroxyethylsulphonamide protease inhibitor (Vertex); XM 323: cyclic urea protease inhibitor (Dupont Merck).

Therapies for the Treatment of Flaviviridae Infection

Drug-resistant variants of flaviviruses, pestiviruses or HCV are known to emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistriution or other parameter of the drug can be altered by such combination or alternation therapy. In general, combination therapy is typically preferred over alternation therapy because it induces multiple simultaneous stresses on the virus.

Any of the viral treatments described in the Background of the Invention can be used in combination or alternation with the compounds described in this specification. Nonlimiting examples include:

(1) an interferon and/or ribavirin (see, for example, Battaglia, A. M. et al., Ann. Pharmacother. 34:487-494, 2000); Berenguer, M. et al. Antivir. Ther. 3(Suppl. 3):125-136, 1998);

(2) Substrate-based NS3 protease inhibitors (see, for example, Attwood et al., Antiviral peptide derivatives, PCT WO 98/22496, 1998; Attwood et al., Antiviral Chemistry and Chemotherapy 1999, 10, 259-273; Attwood et al., Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (see, for example, Llinas-Brunet et al, Hepatitis C inhibitor peptide analogues, PCT WO 99/07734).

(3) Non-substrate-based inhibitors such as 2,4,6-trihydroxy-3-nitro-benzamide derivatives (see, for example, Sudo K. et al., Biochemical and Biophysical Research Communications, 1997, 238, 643-647; Sudo K. et al. Antiviral Chemistry and Chemotherapy, 1998, 9, 186), including RD3-4082 and RD3-4078, the former substituted on the amide with a 14 carbon chain and the latter processing a para-phenoxyphenyl group;

(4) Thiazolidine derivatives, for example, that show relevant inhibition in a reverse-phase HPLC assay with an NS3/4A fusion protein and NS5A/5B substrate (see, for example, Sudo K. et al., Antiviral Research, 1996, 32, 9-18), especially compound RD-1-6250, possessing a fused cinnamoyl moiety substituted with a long alkyl chain, RD4 6205 and RD4 6193;

(5) Thiazolidines and benzanilides, for example, as identified in Kakiuchi N. et al. J. EBS Letters 421, 217-220; Takeshita N. et al. Analytical Biochemistry, 1997, 247, 242-246;

(6) A phenanthrenequinone possessing activity against protease in a SDS-PAGE and autoradiography assay, for example, isolated from the fermentation culture broth of *Streptomyces* sp., Sch 68631 (see, for example, Chu M. et al., Tetrahedron Letters, 1996, 37, 7229-7232), and Sch 351633, isolated from the fungus *Penicillium griseofulvum*, which demonstrates activity in a scintillation proximity assay (see, for example, Chu M. et al., Bioorganic and Medicinal Chemistry Letters 9, 1949-1952);

(7) Selective NS3 inhibitors, for example, based on the macromolecule elgin c, isolated from leech (see, for example, Qasim M. A. et al., Biochemistry, 1997, 36, 1598-1607);

(8) Helicase inhibitors (see, for example, Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(9) Polymerase inhibitors such as i) nucleotide analogues, for example, gliotoxin (see, for example, Ferrari R. et al. Journal of Virology, 1999, 73, 1649-1654);

ii) the natural product cerulenin (see, for example, Lohmann V. et al., Virology, 1998, 249, 108-118); and iii) non-nucleoside polymerase inhibitors, including, for example, compound R803 (see, for example, WO 04/018463 A2 and WO 03/040112 A1, both to Rigel Pharmaceuticals, Inc.); substituted diamine pyrimidines (see, for example, WO 03/063794 A2 to Rigel Pharmaceuticals, Inc.); benzimidazole derivatives (see, for example, Bioorg. Med. Chem. Lett., 2004, 14:119-124 and Bioorg. Med. Chem. Lett., 2004, 14:967-971, both to Boehringer Ingelheim Corporation); N,N-disubstituted phenylalanines (see, for example, J. Biol. Chem., 2003, 278:9495-98 and J. Med. Chem., 2003, 13:1283-85, both to Shire Biochem, Inc.); substituted thiophene-2-carboxylic acids (see, for example, Bioorg. Med. Chem. Lett., 2004, 14:793-796 and Bioorg. Med. Chem. Lett., 2004, 14:797-800, both to Shire Biochem, Inc.); α,γ-diketoacids (see, for example, J. Med. Chem., 2004, 14-17 and WO 00/006529 A1, both to Merck & Co., Inc.); and meconic acid derivatives (see, for example, Bioorg. Med.

Chem. Lett., 2004, 3257-3261, WO 02/006246 A1 and WO03/062211 A1, all to IRBM Merck & Co., Inc.);

(10) Antisense phosphorothioate oligodeoxynucleotides (S-ODN) complementary, for example, to sequence stretches in the 5' non-coding region (NCR) of the virus (see, for example, Alt M. et al., Hepatology, 1995, 22, 707-717), or to nucleotides 326-348 comprising the 3' end of the NCR and nucleotides 371-388 located in the core coding region of the HCV RNA (see, for example, Alt M. et al., Archives of Virology, 1997, 142, 589-599; Galderisi U. et al., Journal of Cellular Physiology, 1999, 181, 251-257).

(11) Inhibitors of IRES-dependent translation (see, for example, Ikeda N et al., Agent for the prevention and treatment of hepatitis C, Japanese Patent Pub. JP-08268890; Kai Y. et al. Prevention and treatment of viral diseases, Japanese Patent Pub. JP-10101591).

(12) Nuclease-resistant ribozymes (see, for example, Maccjak, D. J. et al., Hepatology 1999, 30, abstract 995).

(13) Nucleoside analogs have also been developed for the treatment of Flaviviridae infections. Examples include the following.

Idenix Pharmaceuticals, Ltd. discloses branched nucleosides, and their use in the treatment of HCV and flaviviruses and pestiviruses in US Patent Publication No. 2003/0050229 A1 and US Patent Publication No. 2003/0060400 A1, which correspond to International Publication Nos. WO 01/90121 and WO 01/92282. A method for the treatment of hepatitis C infection (and flaviviruses and pestiviruses) in humans and other host animals is disclosed in the Idenix publications that includes administering an effective amount of a biologically active 1', 2', 3' or 4'-branched β-D or β-L nucleosides or a pharmaceutically acceptable salt or prodrug thereof, administered either alone or in combination, optionally in a pharmaceutically acceptable carrier. See also U.S. Patent Publication Nos. 2004/0006002 and 2004/0006007 as well as WO 03/026589 and WO 03/026675. Idenix Pharmaceuticals, Ltd. also discloses in US Patent Publication No. 2004/0077587 pharmaceutically acceptable branched nucleoside prodrugs, and their use in the treatment of HCV and flaviviruses and pestiviruses in prodrugs. See also PCT Publication Nos. WO 04/002422, WO 04/002999, and WO 04/003000.

Biota Inc. discloses various phosphate derivatives of nucleosides, including 1', 2', 3' or 4'-branched β-D or β-L nucleosides, for the treatment of hepatitis C infection in International Patent Publication WO 03/072757.

Emory University and the University of Georgia Research Foundation, Inc. (UGARF) discloses the use of 2'-fluoronucleosides for the treatment of HCV in U.S. Pat. No. 6,348, 587. See also US Patent Publication No. 2002/0198171 and International Patent Publication WO 99/43691.

BioChem Pharma Inc. (now Shire Biochem, Inc.) discloses the use of various 1,3-dioxolane nucleosides for the treatment of a Flaviviridae infection in U.S. Pat. No. 6,566,365. See also U.S. Pat. Nos. 6,340,690 and 6,605,614; U.S. patent Publication Nos. 2002/0099072 and 2003/0225037, as well as International Publication No. WO 01/32153 and WO 00/50424.

BioChem Pharma Inc. (now Shire Biochem, Inc.) also discloses various other 2'-halo, 2'-hydroxy and 2'-alkoxy nucleosides for the treatment of a Flaviviridae infection in US Patent Publication No. 2002/0019363 as well as International Publication No. WO 01/60315 (PCT/CA01/00197; filed February 19, 2001).

ICN Pharmaceuticals, Inc. discloses various nucleoside analogs that are useful in modulating immune response in U.S. Pat. Nos. 6,495,677 and 6,573,248. See also WO 98/16184, WO 01/68663, and WO 02/03997.

U.S. Pat. No. 6,660,721; US patent Publication Nos. 2003/083307 A1, 2003/008841 A1, and 2004/0110718; as well as International Patent Publication Nos. WO 02/18404; WO 02/100415, WO 02/094289, and WO 04/043159; filed by F. Hoffmann-La Roche AG, discloses various nucleoside analogs for the treatment of HCV RNA replication.

Pharmasset Limited discloses various nucleosides and antimetabolites for the treatment of a variety of viruses, including Flaviviridae, and in particular HCV, in US Patent Publication Nos. 2003/0087873, 2004/0067877, 2004/0082574, 2004/0067877, 2004/002479, 2003/0225029, and 2002/00555483, as well as International Patent Publication Nos. WO 02/32920, WO 01/79246, WO 02/48165, WO 03/068162, WO 03/068164 and WO 2004/013298.

Merck & Co., Inc. and Isis Pharmaceuticals disclose in US Patent Publication No. 2002/0147160, 2004/0072788, 2004/0067901, and 2004/0110717; as well as the corresponding International Patent Publication Nos. WO 02/057425 (PCT/US02/01531; filed Jan. 18, 2002) and WO 02/057287 (PCT/US02/03086; filed Jan. 18, 2002) various nucleosides, and in particular several pyrrolopyrimidine nucleosides, for the treatment of viruses whose replication is dependent upon RNA-dependent RNA polymerase, including Flaviviridae, and in particular HCV. See also WO 2004/000858, WO 2004/003138, WO 2004/007512, and WO 2004/009020.

US Patent Publication No. 2003/028013 A1 as well as International Patent Publication Nos. WO 03/051899, WO 03/061576, WO 03/062255 WO 03/062256, WO 03/062257, and WO 03/061385, filed by Ribapharm, also are directed to the use of certain nucleoside analogs to treat hepatitis C virus.

Genelabs Technologies disclose in US Patent Publication No. 2004/0063658 as well as International Patent Publication Nos. WO 03/093290 and WO 04/028481 various base modified derivatives of nucleosides, including 1', 2', 3' or 4'-branched β-D or β-L nucleosides, for the treatment of hepatitis C infection.

(14) Other miscellaneous compounds including 1-aminoalkylcyclohexanes (for example, U.S. Pat. No. 6,034,134 to Gold et al.), alkyl lipids (for example, U.S. Pat. No. 5,922,757 to Chojkier et al.), vitamin E and other antioxidants (for example, U.S. Pat. No. 5,922,757 to Chojkier et al.), squalene, amantadine, bile acids (for example, U.S. Pat. No. 5,846,964 to Ozeki et al.), N-(phosphonoacetyl)-L-aspartic acid (for example, U.S. Pat. No. 5,830,905 to Diana et al.), benzenedicarboxamides (for example, U.S. Pat. No. 5,633, 388 to Diana et al.), polyadenylic acid derivatives (for example, U.S. Pat. No. 5,496,546 to Wang et al.), 2',3'-dideoxyinosine (for example, U.S. Pat. No. 5,026,687 to Yarchoan et al.), and benzimidazoles (for example, U.S. Pat. No. 5,891,874 to Colacino et al.).

(15) Other compounds currently in clinical development for treatment of hepatitis c virus include, for example: Interleukin-10 by Schering-Plough, IP-501 by Interneuron, Merimebodib VX-497 by Vertex, AMANTADINE (Symmetrel) by Endo Labs Solvay, HEPTAZYME by RPI, IDN-6556 by Idun Pharma., XTL-002 by XTL., HCV/MF59 by Chiron, CIVACIR by NABI, LEVOVIRIN by ICN, VIRAMIDINE by ICN, ZADAXIN (thymosin alfa-1) by Sci Clone, CEPLENE (histamine dihydrochloride) by Maxim, VX 950/LY 570310 by Vertex/Eli Lilly, ISIS14803 by Isis Pharmaceutical/Elan, IDN-6556 by Idun Pharmaceuticals, Inc. and JTK 003 by AKROS Pharma.

Therapies for the Treatment of Abnormal Cellular Proliferation

Examples of agents that have been identified as active against abnormal cellular proliferation, and thus can be used in combination or alternation with one or more nucleosides of general formula (I)-(IV) include:

Alkylating Agents

Nitrogen Mustards: Mechlorethamine (Hodgkin's disease, non-Hodgkin's lymphomas), Cyclophosphamide, Ifosfamide (acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas), Melphalan (L-sarcolysin) (multiple myeloma, breast, ovary), Chlorambucil (chronic lymphoctic leukemia, primary macroglobulinemia, Hodgkin's disease, non-Hodgkin's lymphomas).

Ethylenimines and Methylmelamines: Hexamethylmelamine (ovary), Thiotepa (bladder, breast, ovary).

Alkyl Sulfonates: Busulfan (chronic granuloytic leukemia).

Nitrosoureas: Carmustine (BCNU) (Hodgkin's disease, non-Hodgkin's lymphomas, primary brain tumors, multiple myeloma, malignant melanoma), Lomustine (CCNU) (Hodgkin's disease, non-Hodgkin's lymphomas, primary brain tumors, small-cell lung), Semustine (methyl-CCNU) (primary brain tumors, stomach, colon), Streptozocin (STR) (malignant pancreatic insulinoma, malignant carcinoin).

Triazenes: Dacarbazine (DTIC; dimethyltriazenoimidazole-carboxamide) (malignant melanoma, Hodgkin's disease, soft-tissue sarcomas).

Antimetabolites

Folic Acid Analogs: Methotrexate (amethopterin) (acute lymphocytic leukemia, choriocarcinoma, mycosis fungoides, breast, head and neck, lung, osteogenic sarcoma).

Pyrimidine Analogs: Fluorouracil (5-fluorouracil; 5-FU) Floxuridine (fluorodeoxyuridine; FUdR) (breast, colon, stomach, pancreas, ovary, head and neck, urinary bladder, premalignant skin lesions) (topical), Cytarabine (cytosine arabinoside) (acute granulocytic and acute lymphocytic leukemias).

Purine Analogs and Related Inhibitors: Mercaptopurine (6-mercaptopurine; 6-MP) (acute lymphocytic, acute granulocytic and chronic granulocytic leukemia), Thioguanine (6-thioguanine: TG) (acute granulocytic, acute lymphocytic and chronic granulocytic leukemia), Pentostatin (2'-deoxycyoformycin) (hairy cell leukemia, mycosis fungoides, chronic lymphocytic leukemia).

Vinca Alkaloids: Vinblastine (VLB) (Hodgkin's disease, non-Hodgkin's lymphomas, breast, testis), Vincristine (acute lymphocytic leukemia, neuroblastoma, Wilms' tumor, rhabdomyosarcoma, Hodgkin's disease, non-Hodgkin's lymphomas, small-cell lung).

Epipodophylotoxins: Etoposide (testis, small-cell lung and other lung, breast, Hodgkin's disease, non-Hodgkin's lymphomas, acute granulocytic leukemia, Kaposi's sarcoma), Teniposide (testis, small-cell lung and other lung, breast, Hodgkin's disease, non-Hodgkin's lymphomas, acute granulocytic leukemia, Kaposi's sarcoma).

Natural Products

Antibiotics: Dactinomycin (actinonmycin D) (choriocarcinoma, Wilms' tumor rhabdomyosarcoma, testis, Kaposi's sarcoma), Daunorubicin (daunomycin; rubidomycin) (acute granulocytic and acute lymphocytic leukemias), Doxorubicin (soft tissue, osteogenic, and other sarcomas; Hodgkin's disease, non-Hodgkin's lymphomas, acute leukemias, breast, genitourinary thyroid, lung, stomach, neuroblastoma), Bleomycin (testis, head and neck, skin and esophagus lung, and genitourinary tract, Hodgkin's disease, non-Hodgkin's lymphomas), Plicamycin (mithramycin) (testis, malignant hypercalcema), Mitomycin (mitomycin C) (stomach, cervix, colon, breast, pancreas, bladder, head and neck).

Enzymes: L-Asparaginase (acute lymphocytic leukemia).

Biological Response Modifiers: Interferon-alfa (hairy cell leukemia, Kaposi's sarcoma, melanoma, carcinoid, renal cell, ovary, bladder, non Hodgkin's lymphomas, mycosis fungoides, multiple myeloma, chronic granulocytic leukemia).

Miscellaneous Agents

Platinum Coordination Complexes: Cisplatin (cis-DDP) Carboplatin (testis, ovary, bladder, head and neck, lung, thyroid, cervix, endometrium, neuroblastoma, osteogenic sarcoma).

Anthracenedione: Mixtozantrone (acute granulocytic leukemia, breast).

Substituted Urea: Hydroxyurea (chronic granulocytic leukemia, polycythemia vera, essential thrombocytosis, malignant melanoma).

Methylhydrazine Derivative: Procarbazine (N-methylhydrazine, MIH) (Hodgkin's disease).

Adrenocortical Suppressant: Mitotane (o,p'-DDD) (adrenal cortex), Aminoglutethimide (breast).

Adrenorticosteriods: Prednisone (acute and chronic lymphocytic leukemias, non-Hodgkin's lymphomas, Hodgkin's disease, breast).

Progestins: Hydroxprogesterone caproate, Medroxyprogesterone acetate, Megestrol acetate (endometrium, breast).

Antioangiogenesis Agents

Angiostatin, Endostatin.

Hormones and Antagonists

Estrogens: Diethylstibestrol Ethinyl estradiol (breast, prostate)

Antiestrogen: Tamoxifen (breast).

Androgens: Testosterone propionate Fluxomyesterone (breast).

Antiandrogen: Flutamide (prostate).

Gonadotropin-Releasing Hormone Analog: Leuprolide (prostate).

Pharmaceutical Compositions

Pharmaceutical compositions based upon a cyclobutyl nucleoside of the present invention or pharmaceutically acceptable salt, ester, salt of ester, prodrug, or salt of prodrug, can be prepared in a therapeutically effective amount for treating a Retroviridae (including HIV), Hepadnaviridae (including HBV), and/or Flaviviridae (including BVDV and HCV) viral infection or abnormal cellular proliferation, optionally in combination with a pharmaceutically acceptable additive, carrier or excipient. The therapeutically effective amount may vary with the infection or condition to be treated, its severity, the treatment regimen to be employed, the pharmacokinetics of the agent used, as well as the patient treated.

In one aspect according to the present invention, the compound according to the present invention is formulated preferably in admixture with a pharmaceutically acceptable carrier. In general, it is preferable to administer the pharmaceutical composition in orally administrable form, but formulations may be administered via parenteral, intravenous, intramuscular, transdermal, buccal, subcutaneous, suppository or other route. Intravenous and intramuscular formulations are preferably administered in sterile saline. One of ordinary skill in the art may modify the formulation within the teachings of the specification to provide numerous formulations for a particular route of administration without rendering the compositions of the present invention unstable or compromising its therapeutic activity. In particular, a modification of a desired compound to render it more soluble in water or other vehicle, for example, may be easily accomplished by routine modification (salt formulation, esterification, etc.).

In certain pharmaceutical dosage forms, the prodrug form of the compound, especially including acylated (acetylated or other) and ether derivatives, phosphate esters and various salt forms of the present compounds, is preferred. One of ordinary skill in the art will recognize how to readily modify the present compound to a prodrug form to facilitate delivery of active compound to a targeted site within the host organism or patient. The artisan also will take advantage of favorable pharmacokinetic parameters of the prodrug form, where applicable, in delivering the desired compound to a targeted site within the host organism or patient to maximize the intended effect of the compound in the treatment of a Retroviridae (including HIV), Hepadnaviridae (including HBV), and/or Flaviviridae (including BVDV and HCV) infection or conditions related to abnormal cellular proliferation.

The amount of compound included within therapeutically active formulations, according to the present invention, is an effective amount for treating the infection or condition, in preferred embodiments, a Retroviridae (including HIV), Hepadnaviridae (including HBV), and/or Flaviviridae (including BVDV and HCV) infection or a condition related to abnormal cellular proliferation. In general, a therapeutically effective amount of the present compound in pharmaceutical dosage form usually ranges from about 0.1 mg/kg to about 100 mg/kg or more, depending upon the compound used, the condition or infection treated and the route of administration. For purposes of the present invention, a prophylactically or preventively effective amount of the compositions, according to the present invention, falls within the same concentration range as set forth above for therapeutically effective amount and is usually the same as a therapeutically effective amount.

Administration of the active compound may range from continuous (intravenous drip) to several oral administrations per day (for example, Q. I.D., B. I.D., etc.) and may include oral, topical, parenteral, intramuscular, intravenous, subcutaneous, transdermal (which may include a penetration enhancement agent), buccal and suppository administration, among other routes of administration. Enteric-coated oral tablets may also be used to enhance bioavailability and stability of the compounds from an oral route of administration. The most effective dosage form will depend upon the pharmacokinetics of the particular agent chosen, as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably mixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated for sustained release by standard techniques. The use of these dosage forms may significantly impact the bioavailability of the compounds in the patient.

For parenteral formulations, the carrier will usually comprise sterile water or aqueous sodium chloride solution, though other ingredients, including those that aid dispersion, also may be included. Where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

Solutions or suspensions used for parental, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

In particularly preferred embodiments according to the present invention, the compounds and compositions are used to treat, prevent or delay the onset of Retroviridae (including HIV), Hepadnaviridae (including HBV), and/or Flaviviridae (including BVDV and HCV) infections or conditions related to abnormal cellular proliferation. Preferably, to treat, prevent or delay the onset of the infection or condition, the compositions will be administered in oral dosage form in amounts ranging from about 250 micrograms up to about 1 gram or more at least once a day, preferably, or up to four times a day. The present compounds are preferably administered orally, but may be administered parenterally, topically or in suppository form.

The compounds according to the present invention, because of their low toxicity to host cells in certain instances, may be advantageously employed prophylactically to prevent Retroviridae (including HIV), Hepadnaviridae (including HBV), and/or Flaviviridae (including BVDV and HCV) infections or conditions related to abnormal cellular proliferation or to prevent the occurrence of clinical symptoms associated with the viral infection or condition. Thus, the present invention also encompasses methods for the prophylactic treatment of viral infection, and in particular Retroviridae (including HIV), Hepadnaviridae (including HBV), and/or Flaviviridae (including BVDV and HCV) infections or of a condition related to abnormal cellular proliferation. In this aspect, according to the present invention, the present compositions are used to prevent or delay the onset of a Retroviridae (including HIV), Hepadnaviridae (including HBV), and/or Flaviviridae (including BVDV and HCV) infection or a condition related to abnormal cellular proliferation. This prophylactic method comprises administration to a patient in need of such treatment, or who is at risk for the development of the virus or condition, an amount of a compound according to the present invention effective for alleviating, preventing or delaying the onset of the viral infection or condition. In the prophylactic treatment according to the present invention, it is preferred that the antiviral or antiproliferative compound utilized should be low in toxicity and preferably non-toxic to the patient. It is particularly preferred in this aspect of the present invention that the compound that is used should be maximally effective against the virus or condition and should exhibit a minimum of toxicity to the patient. In the case of Retroviridae (including HIV), Hepadnaviridae (including HBV), and/or Flaviviridae (including BVDV and HCV) infections or conditions related to abnormal cellular proliferation, compounds according to the present invention, which may be used to treat these disease states, may be administered within the same dosage range for therapeutic treatment (i.e., about 250 micrograms up to 1 gram or more from one to four times per day for an oral dosage form) as a prophylactic agent to prevent the proliferation of a Retroviridae (including HIV), Hepadnaviridae (including HBV), and/or Flaviviridae (including BVDV and HCV) infection or conditions related to abnormal cellular proliferation, or alternatively, to prolong the onset of a Retroviridae (including HIV), Hepadnaviridae (including HBV), and/or Flaviviridae (including BVDV and HCV) infection or conditions related to abnormal cellular proliferation, which manifests itself in clinical symptoms.

The compounds or their pharmaceutically acceptable derivative or salts thereof can also be mixed with other active materials that do not impair the desired action, or with materials that supplement the desired action, such as antibiotics, antifungals, anti-inflammatories, protease inhibitors, or other nucleoside or non-nucleoside antiviral agents, as discussed in more detail above. In addition, compounds according to the present invention can be administered in combination or alternation with one or more antiviral, anti-HBV, anti-HCV or anti-herpetic agent or interferon, anti-cancer or antibacterial agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

Controlled Release Formulations

The field of biodegradable polymers has developed rapidly since the synthesis and biodegradability of polylactic acid was reported by Kulkarni et al., in 1966 ("Polylactic acid for surgical implants," Arch. Surg., 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers). See also U.S. Pat. No. 5,626,863 to Hubbell, et al which describes photopolymerizable biodegradable hydrogels as tissue contacting materials and controlled release carriers (hydrogels of polymerized and crosslinked macromers comprising hydrophilic oligomers having biodegradable monomeric or oligomeric extensions, which are end capped monomers or oligomers capable of polymerization and crosslinking); and PCT WO 97/05185 filed by Focal, Inc. directed to multiblock biodegradable hydrogels for use as controlled release agents for drug delivery and tissue treatment agents.

Degradable materials of biological origin are well known, for example, crosslinked gelatin. Hyaluronic acid has been crosslinked and used as a degradable swelling polymer for biomedical applications (U.S. Pat. No. 4,957,744 to Della Valle et. al.; (1991) "Surface modification of polymeric biomaterials for reduced thrombogenicity," Polym. Mater. Sci. Eng., 62:731-735]).

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few manometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622, 219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses a method for forming an implant in situ by dissolving a nonreactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

A number of patents disclose drug delivery systems that can be used to administer the cyclobutyl nucleoside or nucleotide of the present invention or other defined prodrug thereof. U.S. Pat. No. 5,749,847 discloses a method for the delivery of nucleotides into organisms by electrophoration. U.S. Pat. No. 5,718,921 discloses microspheres comprising polymer and drug dispersed there within. U.S. Pat. No. 5,629, 009 discloses a delivery system for the controlled release of bioactive factors. U.S. Pat. No. 5,578,325 discloses nanoparticles and microparticles of non-linear hydrophilic hydrophobic multiblock copolymers. U.S. Pat. No. 5,545,409 discloses a delivery system for the controlled release of bioactive factors. U.S. Pat. No. 5,494,682 discloses ionically cross-linked polymeric microcapsules.

U.S. Pat. No. 5,728,402 to Andrx Pharmaceuticals, Inc. describes a controlled release formulation that includes an internal phase which comprises the active drug, its salt or prodrug, in admixture with a hydrogel forming agent, and an external phase which comprises a coating which resists dissolution in the stomach. U.S. Pat. Nos. 5,736,159 and 5,558, 879 to Andrx Pharmaceuticals, Inc. discloses a controlled release formulation for drugs with little water solubility in which a passageway is formed in situ. U.S. Pat. No. 5,567,441 to Andrx Pharmaceuticals, Inc. discloses a once-α-day controlled release formulation. U.S. Pat. No. 5,508,040 discloses a multiparticulate pulsatile drug delivery system. U.S. Pat. No. 5,472,708 discloses a pulsatile particle based drug delivery system. U.S. Pat. No. 5,458,888 describes a controlled release tablet formulation which can be made using a blend having an internal drug containing phase and an external phase which comprises a polyethylene glycol polymer which has a weight average molecular weight of from 3,000 to 10,000. U.S. Pat. No. 5,419,917 discloses methods for the modification of the rate of release of a drug form a hydrogel which is based on the use of an effective amount of a pharmaceutically acceptable ionizable compound that is capable of providing a substantially zero-order release rate of drug from the hydrogel. U.S. Pat. No. 5,458,888 discloses a controlled release tablet formulation.

U.S. Pat. No. 5,641,745 to Elan Corporation, plc discloses a controlled release pharmaceutical formulation which comprises the active drug in a biodegradable polymer to form microspheres or nanospheres. The biodegradable polymer is suitably poly-D,L-lactide or a blend of poly-D,L-lactide and poly-D,L-lactide-co-glycolide. U.S. Pat. No. 5,616,345 to Elan Corporation plc describes a controlled absorption formulation for once a day administration that includes the active compound in association with an organic acid, and a multi-layer membrane surrounding the core and containing a major proportion of a pharmaceutically acceptable film-forming, water insoluble synthetic polymer and a minor proportion of a pharmaceutically acceptable film-forming water soluble synthetic polymer. U.S. Pat. No. 5,641,515 discloses a controlled release formulation based on biodegradable nanoparticles. U.S. Pat. No. 5,637,320 discloses a controlled absorption formulation for once a day administration. U.S. Pat. Nos. 5,580,580 and 5,540,938 are directed to formulations and their use in the treatment of neurological diseases. U.S. Pat. No. 5,533,995 is directed to a passive transdermal device with controlled drug delivery. U.S. Pat. No. 5,505,962 describes a controlled release pharmaceutical formulation.

Synthetic Protocol

The compounds of the present invention can be synthesized by any means known in the art, including a variety of [2+2] and [3+1] approaches, to obtain cyclobutyl derivatives of the present invention.

The invention will be understood in further detail in view of the following nonlimiting examples.

EXAMPLES

General Methods $^1$H NMR or $^{13}$C NMR spectra were run at room temperature and were recorded either on 300 MHz or 75 MHz General Electric QE-300 Spectrometer or on 400 MHz or 100 MHz INOVA Spectrometer or 600 MHz or 150 MHz INOVA Spectrometer. $^{31}$P NMR spectra were recorded on 162 MHz INOVA Spectrometer. The spectra obtained were referenced to the residual solvent peak. They were recorded in deuterated chloroform, methyl alcohol deuterium oxide or methyl sulfoxide. Chemical shifts are given in ppm downfield from internal tetramethylsilane as reference. Deuterium exchange, decoupling experiments or 2D-COSY were performed in order to confirm proton assignments. Signal multiplicities are represented by s (singlet), d (doublet), dd (doublet of doublets), t (triplet), q (quadruplet), br (broad), m (multiplet). All J-values are in Hz. FAB mass spectra were recorded in the positive- (FAB>0) or negative- (FAB<0) ion mode on a JEOL DX 300 mass spectrometer. The matrix was 3-nitrobenzyl alcohol (NBA) or a mixture (50:50, v/v) of glycerol and thioglycerol (GT). Specific rotations were measured on a Perkin-Elmer 241 spectropolarimeter (path length 1 cm) and are given in units of $10^{-1}$ deg cm$^2$ g$^{-1}$. Elemental analyses were performed by Atlantic Microlab Inc. (Norcross, Ga.). Analyses indicated by the symbols of the elements or functions were within ±0.4% of theoretical values. Thin layer chromatography was performed on Whatman PK5F silica gel plates, visualization of products being accomplished by UV absorbency, optionally followed by charring with 10% ethanolic sulfuric acid and heating. Column chromatography was carried out on Silica Gel (Fisher, S733-1) at atmospheric pressure. Melting points were determined in open capillary tubes on an Electrothermal digit melting point apparatus and are uncorrected. The UV absorption spectra were recorded on an Uvikon 931 (KONTRON) spectrophotometer in ethanol.

Example 1 trans-3-(Benzyloxymethyl)cyclobutanol

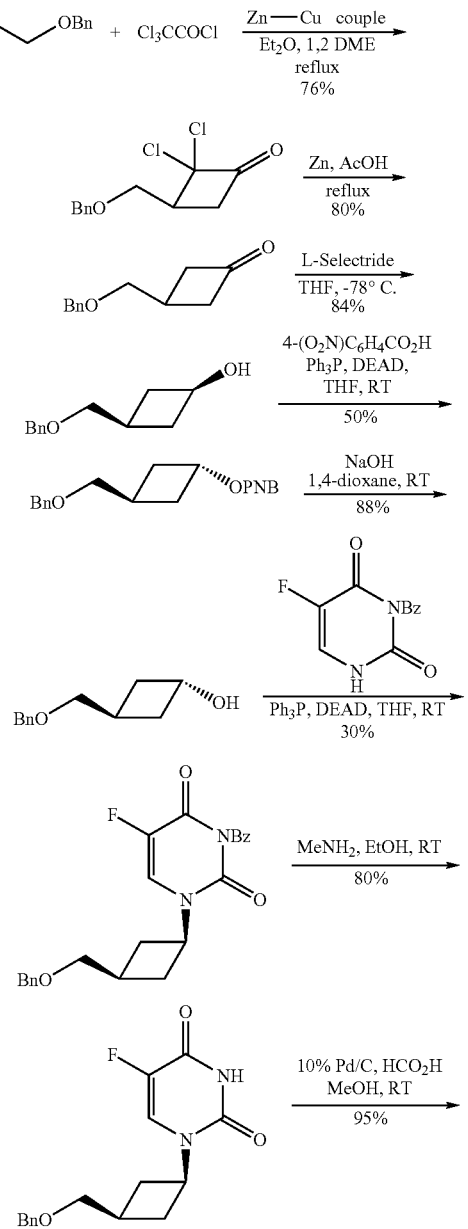

-continued

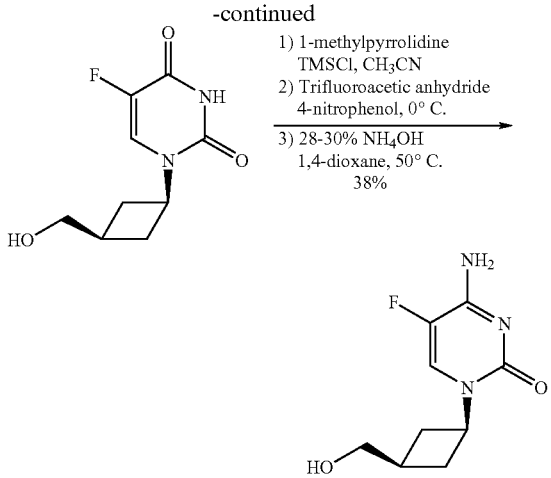

trans-3-(Benzyloxymethyl)cyclobutanol was prepared according to published procedure of Reese, C. B. et. al. *J. Chem. Soc., PT1* 1998, 2827.

A solution of DIAD (2.15 g, 10.6 mmol) in anhydrous THF (10 mL) was added dropwise to a mixture of trans-3-(benzyloxymethyl)cyclobutanol (0.85 g, 4.4 mmol), 3-benzoyl-5-fluorouracil (1.55 g, 6.6 mmol), and triphenylphosphine (2.9 g, 11.07 mmol) in THF (35 mL) at 0° C. The mixture was aged for 72 h at ambient temperature and then concentrated by rotary evaporator. The resulting gum was purified by chromatography over silica gel with a gradient from 10% to 25% EtOAc in hexanes. Fractions with product still contained DIAD and PPh$_3$ as impurities. Isolated 3-benzoyl-5-fluoro-1-[cis-3-(benzyloxymethyl)cyclobutyl]uracil (1.5 g) as impure mixture and used in next step without further purification.

A solution of 3-benzoyl-5-fluoro-1-[cis-3-(benzyloxymethyl)cyclobutyl]uracil (1.5 g) in ethanol (100 mL) was treated with 2 M methylamine in ethanol (5 mL) and aged for 2 h at ambient temperature. Solvent was removed under vacuum and the resulting residue was purified by chromatography over silica gel with a gradient from 50% to 60% ethyl acetate in hexanes to give 5-fluoro-1-[cis-3-(benzyloxymethyl)cyclobutyl]uracil (250 mg, 25% for two steps) as a white solid. $^1$H NMR (CDCl$_3$, 400 MHz): δ 2.19 (m, 2H), 2.36 (s, 1H), 2.50 (m, 2H), 3.47 (d, J=3.84 Hz, 2H), 4.56 (s, 2H), 4.94 (m, 1H), 7.33 (m, 5H), 7.64 (d, J=6.2 Hz, 1H), 9.57 (broad s, 1H); $^{13}$C NMR (CDCl$_3$, 125 MHz)): δ 27.91, 31.17, 46.53, 71.88, 73.60, 125.45, 125.88, 127.92, 128.12, 128.788, 138.26, 139.16, 142.32, 149.68, 157.26.

A solution of 5-fluoro-1-[cis-3-(benzyloxymethyl)cyclobutyl]uracil (250 mg, 0.79 mmol), 10% palladium on activated carbon (50 mg) and formic acid (2 mL) in ethanol (20 mL) was placed under 45 PSI of hydrogen on a Parr Apparatus for 2 h. The mixture was filtered through a pad of Celite and the charcoal was washed with ethanol (3×20 mL). Combined filtrates were concentrated under vacuum and purified by a short column of silica gel with 4% MeOH in CH$_2$Cl$_2$ to give 5-fluoro-1-[cis-3-(hydroxymethyl)cyclobutyl]uracil (159 mg, 94%) as a white solid.

A solution of 5-fluoro-1-[cis-3-(hydroxymethyl)cyclobutyl]uracil (139 mg, 0.65 mmol) and methylpyrrolidine (530 mg, 6.2 mmol) in anhydrous CH$_3$CN was treated dropwise with chlorotrimethylsilane (211 mg, 1.9 mmol). The mixture was aged for 1 h at ambient temperature, cooled to 0° C. and treated dropwise over 5 min. with trifluoroacetic anhydride (680 mg, 3.2 mmol). After 40 min. at 0° C. 4-nitrophenol was added to the mixture, and the mixture aged for an additional 2 h at 0° C. The mixture was poured into saturated sodium bicarbonate solution (20 mL) and extracted with CH$_2$Cl$_2$ (3×40 mL). Combined organic phases were dried over magnesium sulfate and then concentrated. The residue was dissolved in dioxane (10 mL) and 30% aqueous NH$_4$OH (2.5 mL) and heated at 50° C. for 40 h in a sealed vessel. The mixture was cooled to ambient temperature and concentrated under vacuum. The resulting residue was purified by chromatography on silica gel with 10% CH$_3$OH in CH$_2$Cl$_2$ with 1% NH$_4$OH (v/v) to give 5-fluoro-1-[cis-3-(hydroxymethyl)-cyclobutyl]cytosine (53 mg, 38%) as a white solid and recovered starting material (50 mg). $^1$H NMR (DMSO-d$_6$, 400 MHz): δ 1.89 (m, 2H), 2.09 (m, 1H), 2.24 (m, 2H), 3.39 (d, J=5.1 Hz, 2H), 4.56 (broad s, 1H, OH), 4.64 (m, 1H), 7.36 (broad s, 1H, NH$_2$), 7.58 (broad s, 1H, NH$_2$), 7.97 (d, J=7.2 Hz, 1H); MS (FAB): expected for C$_9$H$_{12}$FN$_3$O$_2$ (M+Li)+ 220.2. Found 220.19.

Example 2 trans-3-(Benzyloxymethyl)cyclobutanol triphosphate

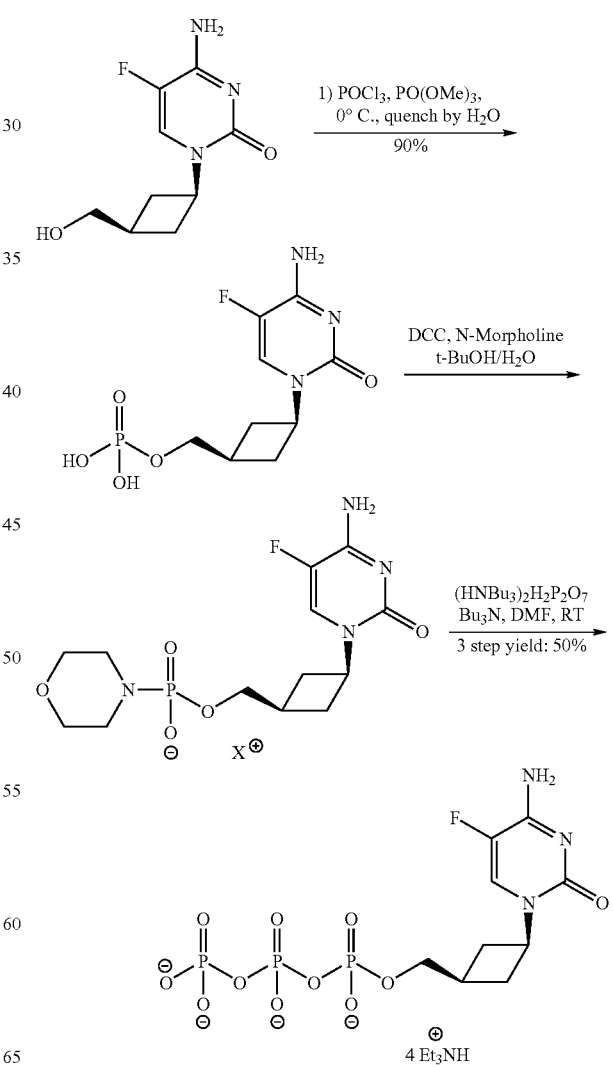

A solution of 5-fluoro-1-[cis-3-(hydroxymethyl)cyclobutyl]cytosine (23 mg, 0.11 mmol) in triethylphosphate was cooled to 0° C. and treated dropwise with phosphorus oxychloride. The mixture was aged for 20 h at 0° C. and then treated with water (0.1 mL). The mixture was aged for 6 h and then concentrated under high vacuum. The crude gum was purified by chromatography on SP207 resin with a gradient from 0-20% methanol in water. Fractions were analyzed by HPLC (reverse phase) and appropriate fractions were lyophilized to give 5-fluoro-1-[cis-3-(hydroxymethyl)cyclobutyl]cytosine mono-phosphate (30 mg) as a gum and was used in next step without further purification. A suspension of 5-fluoro-1-[cis-3-(hydroxymethyl)cyclobutyl]cytosine monophosphate (30 mg) in tert-butanol (1 mL) and water (1 mL) was heated under a gentle reflux while a solution of DCC (91 mg, 0.44 mmol) in tert-butanol was added dropwise over a 1 h period. After 8 h under reflux, the mixture was cooled to rt and the resulting precipitate was filtered and washed with water (3×20 mL). The filtrate was extracted with ether (3×40 mL) and then frozen and lyophilized to give the phosphormorpholidate intermediate (65 mg) as pale yellow solid. A solution of the phosphomorpholidate intermediate (65 mg), anhydrous tributylammonium pyrophosphate (176 mg, 0.386 mmol) in dry DMSO (2 mL) was aged for 4 d at ambient temperature. The yellow mixture was applied directly to a column of DEAE Sephadex (11 mm×220 mm) and eluted with water (50 mL) and then a gradient from 0.35M to 0.45M triethylammonium bicarbonate. Fractions were analyzed by HPLC (reverse phase) and appropriate fractions were pooled and lyophilized. The resulting gum was co-evaporated with ethanol (3×20 mL) under high vacuum to give the triethylammonium-tributylammonium salt of 5-fluoro-1-[cis-3-(hydroxymethyl)-cyclobutyl]-cytosine triphosphate (50 mg) as a sticky white solid. $^1$H NMR (D$_2$O, 400 MHz): δ 1.22 (t, 20H, Et$_3$N), 2.14 (m, 2H), 2.49 (m, 3H), 3.08 (d, 2H), 3.19 (q, 12H, Et$_3$N), 4.64 (m, 1H),), 8.12 (d, J=7.2 Hz, 1H). $^{31}$PNMR (D$_2$O, referenced to H$_3$PO$_4$) δ −22.9 (1P), −10.5 (2P).

Example 3

3-(Benzyloxymethyl)-2,2-dichlorocyclobutanone

Trichloroacetyl chloride (108 ml, 0.96 mol) was added slowly to a stirred suspension of freshly activated zinc-copper couple (56 g), allyl benzyl ether (50 ml, 0.32 mol), dry 1,2-dimethoxyethane (95 ml) and dry diethyl ether (550 ml) in a 2 L three-neck flask under argon. The reactants were heated under gentle reflux for 3d. The products were then filtered and the residue was washed with ether. The combined filtrate and washings were concentrated under reduced pressure. Light petroleum ether was added and the mixture was stirred vigorously. The supernatant was decanted and more light petroleum ether was added. After vigorous stirring the supernatant was again decanted and mixed with the original supernatant. The resulting solution was washed with saturated NaHCO$_3$ twice and brine once. The organic phase was dried over MgSO$_4$ and the solvent was evaporated to give a light yellow oil which was used directly in the next step. $^1$H NMR (CDCl$_3$, 300 MHz): δ 3.10-3.25 (m, 2H), 3.36-3.57 (m, 1H), 3.65-3.75 (m, 1H), 3.83-3.88 (m, 1H), 4.57 (s, 2H), 7.27-7.40 (m, 5H).

Example 4

3-(Benzyloxymethyl)cyclobutanone

Zinc dust (93.5 g, 1.44 mol) was added to a solution of 3-(benzyloxymethyl)-2,2-dichlorocyclobutanone (124 g, 0.48 mol) in glacial acetic acid (800 ml) at room temperature. The reactants were heated at 60° C. for 1 hr, after which time dry diethyl ether was added to the cooled products, which were then filtered. The residue was washed with diethyl ether and the combined filtrate and washings were concentrated under reduced pressure. The residue was dissolved in dichloromethane, which was washed with saturated NaHCO$_3$ twice and water once. The organic phase was dried over MgSO$_4$ and the solvent was evaporated to give an oily product, which was purified by column chromatography (Hexane: EtOAc=6:1).
$^1$H NMR (CDCl$_3$, 400 MHz): δ 2.70 (m, 1H), 2.84-2.92 (m, 2H), 3.08-3.18 (m, 2H), 3.59 (d, J=6.4, 2H), 4.56 (s, 2H), 7.28-7.38 (m, 5H). $^{13}$C NMR (CDCl$_3$, 100 MHz): δ 23.88, 50.26, 73.11, 73.42, 127.88, 127.99, 128.68, 138.26, 207.22.

Example 5

(3-(Benzyloxymethyl)cyclobut-1-enyloxy)-trimethyl-silane

In a 1 L flask charged with argon, dry THF 300 ml was added. This was cooled to −5° C., then n-BuLi (83 ml, 1.6M in hexane, 0.132 mol) was added. After mixing 5 min, diisopropylamine (18 ml, 0.132 mol) was added drop by drop. After stirring for 10 min, this solution was cooled to −78° C. Then a THF solution of 3-(benzyloxymethyl)-cyclobutanone (20 g, 0.11 mol) was added drop by drop at −78° C. After addition, replace the dry ice-acetone bath with ice-water bath. After stirring at 0° C. for 30 min, TMSCl (16 ml, 0.132 mol) was added dropwise, this was stirred at 0° C. for 1 hr and room temperature for 10 min. Then the solvents were removed and the residue was washed with dry pentane and filtered. The filtrate was concentrated to give crude product without further purification. $^1$H NMR (CDCl$_3$, 600 MHz): δ 0.23 (s, 9H), 2.20 (dd, J=12.6, 1.2, 1H), 2.65 (m, 1H), 2.74 (dd, J=13.2, 4.2, 1H), 3.41 (m, 1H), 3.48 (m, 1H), 4.54 (s, 2H), 4.67 (s, 1H), 7.26-7.35 (m, 5H). $^{13}$C NMR (CDCl$_3$, 150 MHz): δ 0.09, 32.70, 38.18, 73.26, 75.41, 93.69, 104.27, 127.70, 127.86, 128.55, 138.20.

Example 6

2-Fluoro-3-(benzyloxymethyl)cyclobutanone

In a 500 ml flask with crude (3-(benzyloxymethyl)cyclobut-1-enyloxy)-trimethyl-silane (14 g, 0.05 mol) inside, dry CH$_3$CN 250 ml was added under argon. After 10 min, SELECFLUOR™ (22 g, 0.06 mol) was added by portions. This was left stirring for 12 hr, after which time the reaction was quenched by adding saturated NH$_4$Cl. The product was extracted with CH$_2$Cl$_2$ three times. The combined organic phase was dried over MgSO$_4$ and the solvents were evaporated to give an oily product, which includes two diastereomers in 3 to 1 ratio. Crude 2-fluoro-3-(benzyloxymethyl)cyclobutanone: $^1$H NMR (CDCl$_3$, 400 MHz): δ 2.60-2.94, 3.05-3.20, 3.59-3.60, 3.70-3.73, 3.80-3.83, 4.50-4.60, 5.39 (d, J=7.2), 5.52 (d, J=6.4), 5.42-5.44 (td, J=8.8, 2.8), 5.55-5.57 (td, J=9.2, 2.4), 7.20-7.40. β-Fluoro-3-(benzyloxymethyl)cyclobutanone: $^1$H NMR (CDCl$_3$, 600 MHz): δ 2.74 (m, 1H), 2.89 (m, 1H), 3.00 (m, 1H), 3.60 (m, 1H), 3.80 (m, 1H), 4.55 (m, 1H), 5.45 (td, J=6.0, 1.6, 0.5H), 5.54 (td, J=6.0, 2.0, 0.5H), 7.28-7.36 (m, 5H). $^{13}$C NMR (CDCl$_3$, 150 MHz): δ31.45 (d, J=18.6), 42.03 (d, J=12.3), 67.38, 73.72, 94.42 (d, J=241.4), 127.84, 127.99, 128.66, 137.97, 200.80.

Example 7

2-Fluoro-3-(benzyloxymethyl)cyclobutanol

In a flask with crude 2-fluoro-3-(benzyloxymethyl)cyclobutanone (7.96 g, 38 mmol) inside, dry THF 100 ml was added under argon. Then cool this solution to −78° C., L-selectride (46 ml, 1.0 M in THF, 46 mmol) was added drop by drop and this was allowed to warm up to room temperature, after which the reaction was quenched with saturated NaHCO$_3$. Then cool the mixture to 0° C., add H$_2$O$_2$ drop by drop, followed by the addition of H$_2$O and EtOAc. The organic phase was separated, washed with H$_2$O twice and brine once, dried over MgSO$_4$ and solvent evaporation gave the crude product, which was purified by column chromatography (Hexane: EtOAc=3:1) to give two diastereomeric cyclobutanols in almost 3 to 1 ratio. α-Fluoro isomer: $^1$H NMR (CDCl$_3$, 400 MHz): δ 1.87 (m, 1H), 2.01 (m, 1H), 2.22 (broad s, 1H), 2.95 (m, 1H), 3.48 (m, 1H), 3.56 (m, 1H), 4.40 (m, 1H), 4.53 (m, 2H), 4.77-4.90 (td, J=54, 4.8), 7.28-7.38 (m, 5H). $^{13}$C NMR (CDCl$_3$, 100 MHz): δ 27.20 (d, J=10.6), 40.82 (d, J=20.5), 67.67 (d, J=18.9), 69.74 (d, J=2.2), 73.29, 89.04 (d, J=216.2), 127.77, 127.87, 128.62, 138.41. MS (FAB): expected for C$_{12}$H$_{15}$FO$_2$ (M+Li)$^+$ 217.2. Found 217.2. β-Fluoro isomer: $^1$H NMR (CDCl$_3$, 400 MHz): δ 1.86 (m, 1H), 2.36-2.54 (m, 2H), 3.00 (d, J=10, 1H), 3.55-3.59 (m, 1H), 3.64-3.68 (m, 1H), 4.19 (m, 1H), 4.56 (s, 2H), 5.07-5.21 (m, J=56, 1H), 7.27-7.38 (m, 5H).

Example 8

α-Fluoro-3-(benzyloxymethyl)cyclobutyl-mesylate

In a flask with α-fluoro-3-(benzyloxymethyl)cyclobutanol (1.9382 g, 9.2 mmol) inside, dry CH$_2$Cl$_2$ was added to give a clear solution under argon. Then Et$_3$N (6.4 ml, 46 mmol) was added to the above solution. After 10 min, cool this to 0° C., MsCl (0.86 ml, 11 mmol) was added drop by drop and this was left stirring with the temperature going up to RT gradually. After 3 hr, quench the reaction by adding H$_2$O to it. Then the organic phase was separated, washed with brine once and dried over MgSO$_4$. Solvent evaporation gave the crude product which was used in the next step without further purification. $^1$H NMR (CDCl$_3$, 600 MHz): δ 2.15 (m, 1H), 2.32 (m, 1H), 3.00 (m, 1H), 3.07 (s, 3H), 3.44-3.47 (m, 1H), 3.58-3.60 (m, 1H), 4.53 (m, 2H), 4.93-5.02 (td, J=54, 4.8, 1H), 5.16 (m, 1H), 7.27-7.40 (m, 5H).

Example 9

N$^3$-PMB-5-fluoro-1-[α-fluoro-3-(benzyloxymethyl)cyclobutyl]uracil

In a 100 ml three-neck flask with N$^3$—PMB protected 5-fluoro-Uracil (2.3476 g, 9.4 mmol), dry K$_2$CO$_3$ (1.2959 g, 9.4 mmol), 18-crown-6 (2.479 g, 9.4 mmol) and a-fluoro-3-(benzyloxymethyl)cyclobutyl-mesylate (2.2537 g, 7.8 mmol) inside, dry DMF 40 ml was added under argon. After addition, the mixture was heated to 120° C., after which time most of the DMF was removed and the residue was dissolved in EtOAc, which was washed with H$_2$O twice and brine once. The organic phase was dried over MgSO$_4$ and solvent evaporation gave the crude product, which includes two regioisomers in 4 to 1 ratio. The product was purified by column chromatography (Hexane: EtOAc=3:1). $^1$H NMR (CDCl$_3$, 600 MHz): δ 1.74 (m, 1H), 2.37 (m, 1H), 2.45 (m, 1H), 3.53 (m, 1H), 3.65 (m, 1H), 3.78 (s, 3H), 4.56 (m, 2H), 4.85 (m, 1H), 4.97 (t, J=6.6, 0.5H), 5.06 (m, 2.5H), 6.83 (d, J=8.4, 2H), 7.25-7.38 (m, 5H), 7.47 (d, J=8.4, 2H). $^{13}$C NMR (CDCl$_3$, 150 MHz): δ 20.19 (d, J=20.7), 36.89 (d, J=20.7), 44.794, 55.20 (d, J=22.6), 55.47, 68.01, 73.61, 89.36 (d, J=227), 113.97, 123.3 (d, J=33), 127.86, 128.19, 128.47, 128.81, 131.33, 137.96, 140.59 (d, J=235.2), 149.86, 157, 159.54.

Oxygen coupled byproduct: N3-PMB-5-fluoro-2-[trans-α-fluoro-cis-3-(benzyloxy-methyl)cyclobutyl]uracil
$^1$H NMR (CDCl$_3$, 400 MHz): δ1.48 (m, 1H), 2.32 (m, 1H), 2.4 (m, 1H), 3.54 (m, 1H), 3.63 (m, 1H), 3.74 (s, 3H), 4.58 (m, 2H), 4.85-4.99 (td, J=54.8, 6.4, 1H), 5.12 (m, 2H), 5.18 (m, 1H), 6.78 (m, 4H), 7.29-7.40 (m, 5H), 7.55 (d, J=1.6, 1H).

Example 10

5-Fluoro-1-[trans-α-fluoro-cis-3-(hydroxymethyl)cyclobutyl]uracil

In a 10 ml flask with AlCl$_3$ (5.61 g, 0.042 mol) inside, dry anisole 20 ml was added under argon to give a light yellow solution. In another flask with N$^3$—PMB-5-fluoro-1-[α-fluoro-3-(benzyloxymethyl)cyclobutyl]uracil (1.865 g, 4.2 mmol) inside, dry anisole 10 ml was added, after which time AlCl$_3$ solution was added to it slowly at room temperature by syringe pump. After addition finishes, cooled the mixture to 0° C., dry MeOH was added slowly to give a colorless solution at the end. Then the solvents were removed and the product was purified by column chromatography (CH$_2$Cl$_2$: MeOH=20:1). $^1$H NMR (CD$_3$OD, 400 MHz): δ 1.69 (m, 1H), 2.34 (m, 2H), 3.70 (m, 2H), 4.75 (m, 1H), 4.96-5.10 (td, J=55.2, 6.4, 1H), 7.88 (d, 1H). MS (ESI$^-$): expected for C$_9$H$_{10}$F$_2$N$_2$O$_3$ [M−H]$^-$231.18. Found 231.2.

Example 11

5-Fluoro-1-[trans-α-fluoro-cis-3-(hydroxymethyl)cyclobutyl]cytosine

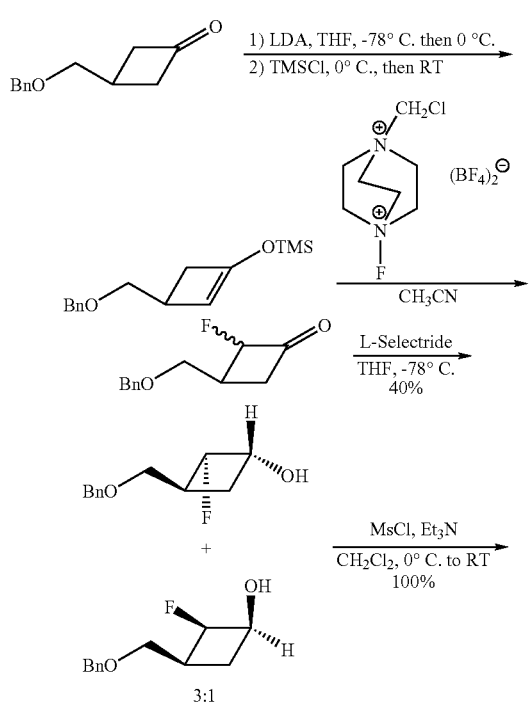

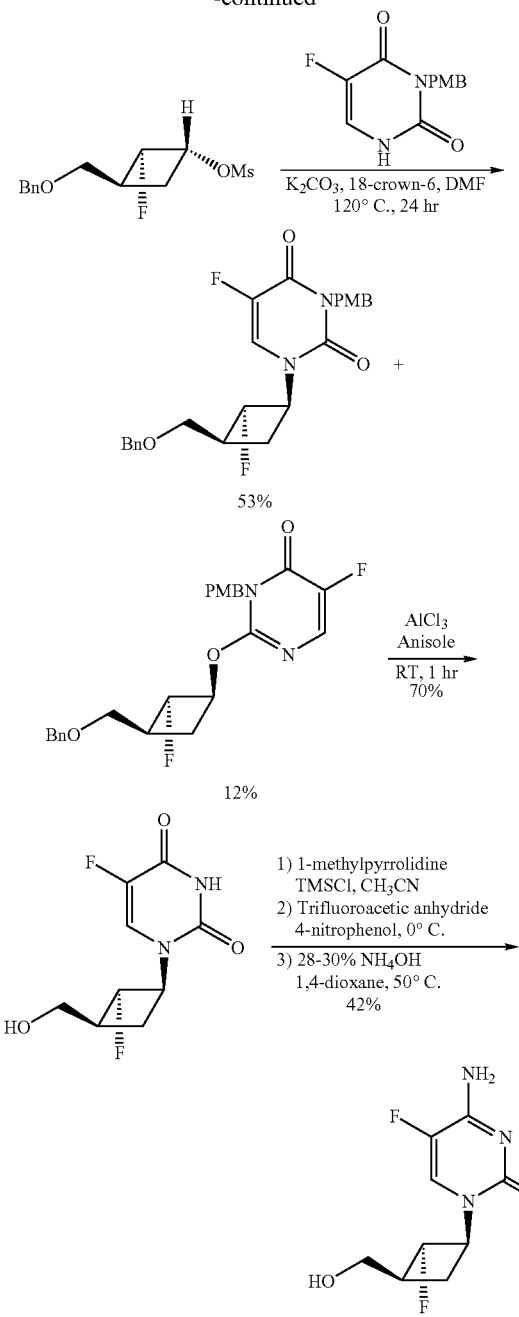

added. The mixture was heated in a sealed flask at 50-60° C. for 24 hr. The resulting solution was concentrated and the residue was co-evaporated with absolute ethanol. The crude product was purified by column chromatography (CH$_2$Cl$_2$: MeOH=10:1). $^1$H NMR (CD$_3$OD, 600 MHz): δ 1.65 (m, 1H), 2.35 (m, 2H), 3.70 (m, 2H), 4.78 (m, 1H), 4.98-5.07 (td, J=54.6, 7.2, 1H), 7.85 (d, J=6.0, 1H). $^{13}$C NMR (CD$_3$OD, 150 MHz): δ 21.13 (d, J=22.8), 40.05 (d, J=18.6), 57.64 (d, J=22.8), 62.42, 91.09 (d, J=222.75), 128.46 (d, J=30.9), 137.83, 157.34, 165.90. MS (ESI$^+$): expected for C$_9$H$_{11}$F$_2$N$_3$O$_2$ [M+H]$^+$ 232.20. Found 232.0.

Oxygen coupled byproduct: 5-Fluoro-2-[trans-α-fluoro-cis-3-(benzyloxymethyl)-cyclobutyl]cytosine $^1$H NMR (CDCl$_3$, 600 MHz): δ 1.48 (m, 1H), 1.65 (broad s, 1H), 2.31 (m, 1H), 2.43 (m, 1H), 3.56 (m, 1H), 3.59 (m, 1H), 4.54 (m, 2H), 4.82-4.91 (td, J=54.6, 6.6, J=1H), 5.12 (m, 2H), 7.28-7.36 (m, 5H), 7.90 (d, J=3.0, 1H). MS (FAB): expected for C$_{16}$H$_{17}$F$_2$N$_3$O$_2$ (M+Li)$^+$328.32. Found 328.28.

Oxygen coupled byproduct: 5-Fluoro-2-[cis-α-fluoro-trans-3-(benzyloxymethyl)-cyclobutyl] cytosine $^1$H NMR (CDCl$_3$, 600 MHz): δ 2.04 (m, 1H), 2.28 (m, 1H), 3.04 (m, 1H), 3.51 (m, 1H), 3.59 (m, 1H), 4.54 (m, 2H), 4.99-5.07 (td, J=51, 4.8, 1H), 5.26-5.29 (m, 3H), 7.26-7.37 (m, 5H), 7.90 (d, J=3.0, 1H). $^{13}$C NMR (CDCl$_3$, 150 MHz): δ 24.57 (d, J=10.4), 41.16 (d, J=20.6), 69.50, 71.93 (d, J=18.6), 73.23, 87.73 (d, J=226), 127.74, 127.85, 128.61, 138.43, 140.77 (d, J=20.7), 142.81 (d, J=247), 154.76 (d, J=12.5), 160.07.

Example 12

5-Fluoro-1-[trans-α-fluoro-cis-3-(hydroxymethyl)cyclobutyl]uracil Triphosphate

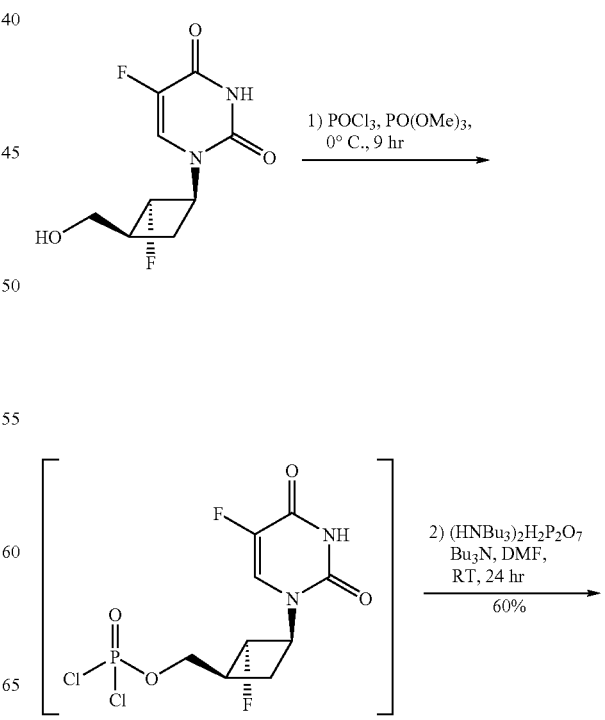

In a flask with 5-fluoro-1-[α-fluoro-3-(hydroxymethyl)cyclobutyl]uracil (0.2649 g, 1.14 mmol) inside, dry CH$_3$CN 10 ml was added under argon, followed by the addition of 1-methylpyrrolidine (1.14 ml, 10.9 mmol) and chlorotrimethylsilane (0.43 ml, 3.4 mmol) at room temperature. After 1 hr, the reactants were cooled to 0° C. and trifluoroacetic anhydride (0.78 ml, 5.7 mmol) was added dropwise over 5 min. After 30 min at 0° C., a CH$_3$CN solution of 4-nitrophenol (0.4765 g, 3.4 mmol) was added drop by drop at 0° C. This was allowed to stir for 3 hr more, after which time the mixture was poured into saturated NaHCO$_3$ and the resulting mixture was extracted with CH$_2$Cl$_2$ four times. The combined organic extracts were dried over MgSO$_4$ and evaporated under reduced pressure. The residue was dissolved in dioxane 10 ml and concentrated ammonia hydroxide (28-30%) 2.5 ml was -continued

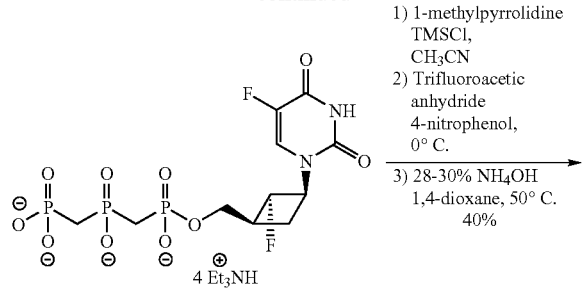

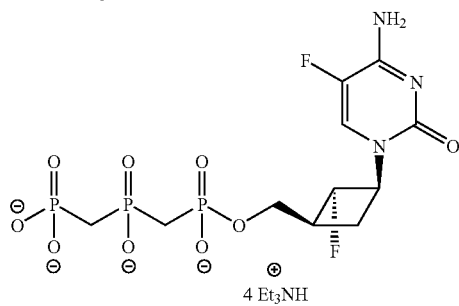

In a 25 ml flask with 5-fluoro-1-[α-fluoro-3-(hydroxymethyl)cyclobutyl]uracil (29 mg, 0.125 mmol) inside, PO(OMe)$_3$ 0.6 ml was added under argon to give a colorless solution. Then cool this to 0° C. and add POCl$_3$ (0.024 ml, 0.26 mmol) drop by drop. This was left stirring at 0° C. for 24 hr. In another 5 ml flask with (HNBu$_3$)$_2$H$_2$P$_2$O$_7$ (0.237 g, 0.5 mmol) inside, dry DMF 1 ml was added under argon to give a colorless solution, after which Bu$_3$N (0.29 ml, 1.2 mmol) was added slowly. After stirring for 10 min, this was added very slowly to the previous flask. After reacting for 2 hr, quench the reaction by adding 0.1 M TEAB 5 ml drop by drop, then directly apply them on the DEAE-sephadex dianion exchange column (11 mm×220 mm, gradually eluent from 0.1 M TEAB to 0.7 M TEAB). After analyzing the fractions by HPLC with C-18 reverse phase column (250×4.6 mm), collect all the products and lyophilized to give the triethylammonium salt of 5-fluoro-1-[α-fluoro-3-(hydroxymethyl)cyclobutyl]uracil triphosphate as a light yellow sticky solid. $^1$H NMR (D$_2$O, 400 MHz): δ 1.27 (t, J=7.2), 1.78 (m, 1H), 2.41 (m, 1H), 2.59 (m, 1H), 3.05 (m, 36 H), 3.19 (m, 24H), 3.88-4.17 (m, 2H), 5.01-5.14 (td, J=53.6, 1H), 7.97 (d, J=6.4, 1H). $^{31}$P NMR (D$_2$O, 162 MHz): δ −9.17 (γ), −11.13 (α), −23.02 (β).

Example 13

1-[trans-α-Fluoro-cis-3-(benzyloxymethyl)cyclobutyl]uracil

In a 25 ml three-neck flask with tetrabutylammonium uracil salt (0.8825 g, 3 mmol) inside, dry DMF 7 ml was added to give a light yellow solution. After stirring for 5 min, a DMF solution of a-Fluoro-3-(benzyloxymethyl)cyclobutyl-mesylate (0.6 g, 2.5 mmol) was added with the color changing from light yellow to orange yellow. Then began to heat to 120° C. After 24 hr, stop heating and let it stir for overnight. Then add AcOH 0.2 ml, after stirring for 10 min, remove most of DMF and then add EtOAc, which was washed with H$_2$O three times and brine once. The organic phase was dried over MgSO$_4$ and solvent evaporation gave the crude product, which was purified by column chromatography (Hexane: EtOAc=3:1 to Hexane: EtOAc=1:1). $^1$H NMR (CDCl$_3$, 400 MHz): δ 1.75 (m, 1H), 2.26-2.49 (m, 2H), 3.51-3.54 (m, 1H), 3.63-3.66 (m, 1H), 4.54 (m, 2H), 4.79 (m, 1H), 5.00-5.13 (td, J=54.8, 6.4, 1H), 5.68 (d, J=8.0, 1H), 7.22-7.24 (d, J=8.0, 1H), 7.25-7.36 (m, 5H), 10.09 (s, 1H). $^{13}$C NMR (CDCl$_3$, 100 MHz): δ 20.33 (d, J=20.7), 36.97 (d, J=19.7), 54.58 (d, J=23.4), 68.34, 73.52, 89.48 (d, J=226.3), 102.96, 127.87, 128.11, 128.72, 138.03, 141.15, 150.90, 163.53. MS (FAB): expected for C$_{16}$H$_{17}$FN$_2$O$_3$ (M+Li)$^+$311.32. Found 311.2.

Example 14

1-[trans-α-Fluoro-cis-3-(benzyloxymethyl)cyclobutyl]cytosine

In a 25 ml flask with 1-[α-fluoro-3-(hydroxymethyl)cyclobutyl]uracil (0.1775 g, 0.58 mmol) inside, dry CH$_3$CN 3 ml was added under argon, followed by the addition of 1-methylpyrrolidine (0.58 ml, 5.6 mmol) and chlorotrimethylsilane (0.22 ml, 1.75 mmol) at room temperature. After 1 hr, the reactants were cooled to 0° C. and trifluoroacetic anhydride (0.41 ml, 3 mmol) was added dropwise over 5 min. After 30 min at 0° C., a CH$_3$CN solution of 4-nitrophenol (0.24 g, 1.75 mmol) was added drop by drop at 0° C. This was allowed to stir for 3 hr more, after which time the mixture was poured into saturated NaHCO$_3$ and the resulting mixture was extracted with CH$_2$Cl$_2$ four times. The combined organic extracts were dried over MgSO$_4$ and evaporated under reduced pressure. The residue was dissolved in dioxane 10 ml and concentrated ammonia hydroxide (28-30%) 2.5 ml was added. The mixture was heated in a sealed flask at 50-60° C. for 24 hr. The resulting solution was concentrated and the residue was co-evaporated with absolute ethanol. The crude product was purified by column chromatography (CH$_2$Cl$_2$: MeOH=20:1). $^1$H NMR (CD$_3$OD, 400 MHz): δ 1.70 (m, 1H), 2.36 (m, 1H), 2.47 (m, 1H), 3.59-3.68 (m, 2H), 4.56 (s, 2H), 4.77 (m, 1H), 5.02-5.16 (td, J=55.2, 6.8, 1H), 5.86 (d, J=7.6, 1H), 7.26-7.36 (m, 5H), 7.60 (d, J=7.6, 1H). MS (FAB): expected for C$_{16}$H$_{18}$FN$_3$O$_2$ (M+Li)$^+$310.33. Found 310.2.

Example 15

1-[trans-α-Fluoro-cis-3-(hydroxymethyl)cyclobutyl] cytosine

BCl$_3$ (0.2 ml, 0.21 mmol) was added dropwise to a stirred solution of 1-[α-fluoro-3-(benzyloxymethyl)cyclobutyl]cytosine (20.7 mg, 0.07 mmol) in CH$_2$Cl$_2$ at −78° C. After 6 hr, add ammonium in MeOH (7N) drop by drop to quench the reaction and then evaporate the solvents. The crude material was purified by column chromatography (CH$_2$Cl$_2$: MeOH=10:1 to 5:1). $^1$H NMR (CD$_3$OD, 400 MHz): δ 1.69 (m, 1H), 2.28-2.44 (m, 2H), 3.62-3.74 (m, 2H), 4.77 (m, 1H), 4.99-5.13 (td, J=54.8, 6.8, 1H), 5.94 (d, J=6.8, 1H), 7.68 (d, J=7.6, 1H). $^{13}$C NMR (CD$_3$OD, 100 MHz): δ21.05 (d, J=21.3), 40.15 (d, J=19), 57.66 (d, J=22.8), 62.33, 90.89 (d, J=223.8), 96.23, 144.71, 158.0, 166.87. MS (FAB): expected for C$_9$H$_{12}$FN$_3$O$_2$ (M+Li)$^+$220.21. Found 220.1.

Example 16

1-[trans-α-Fluoro-cis-3-(benzyloxymethyl)cyclobutyl]adenine

In a 25 ml three-neck flask with adenine (0.18 g, 1.33 mmol), dry K$_2$CO$_3$ (0.1846 g, 1.33 mmol), 18-crown-6 (0.1765 g, 0.67 mmol) and α-fluoro-3-(benzyloxymethyl)-cyclobutyl-mesylate (0.1923 g, 0.67 mmol) inside, dry DMF 7 ml was added under argon. After addition, the mixture was heated to 120° C., after which time most of the DMF was removed and the residue was dissolved in EtOAc, which was washed with H$_2$O twice and brine once. The organic phase was dried over MgSO$_4$ and solvent evaporation gave the crude product, which was purified by column chromatography (CH$_2$Cl$_2$: MeOH=10:1). $^1$H NMR (CDCl$_3$, 600 MHz): δ 2.21 (m, 1H), 2.50-2.61 (m, 2H), 3.64-3.67 (m, 1H), 3.71-3.74 (m, 1H), 4.59 (m, 1H), 4.85-4.92 (m, 1H), 5.36-5.45 (td, J=54.6, 7.2, 1H), 6.08 (s, 2H), 7.28-7.36 (m, 5H), 7.83 (s, 1H), 8.33 (s, 1H). $^{13}$C NMR (CDCl$_3$, 150 MHz): δ 21.25 (d, J=13.8), 37.65 (d, J=12.3), 53.27 (d, J=15.1), 69.00, 73.43, 90.73 (d, J=225), 120.09, 127.75, 127.97, 128.57, 128.68, 138.21, 139.09, 150.44, 153.26, 155.86. MS (FAB): expected for C$_{17}$H$_{18}$FN$_5$O (M+Li)$^+$ 334.36. Found 334.3.

Example 17

1-[trans-α-Fluoro-cis-3-(hydroxymethyl)cyclobutyl] adenine

In a 25 ml flask with 1-[α-fluoro-3-(benzyloxymethyl) cyclobutyl]adenine (81.3 mg, 0.25 mmol) inside, dry CH$_2$Cl$_2$ was added. Then cool this to −78° C., after stabilization, BCl$_3$ (0.75 ml, 1.0M in CH$_2$Cl$_2$, 0.75 mmol) was added drop by drop. After 6 hr, add ammonium in MeOH (7N) drop by drop to quench the reaction and then evaporate the solvents. The crude material was purified by column chromatography (CH$_2$Cl$_2$: MeOH=10:1 to 5:1). $^1$H NMR (CD$_3$OD, 400 MHz): δ 2.10 (m, 1H), 2.52 (m, 2H), 3.78 (m, 2H), 5.00 (m, 1H), 5.29-5.42 (td, J=54.8, 6.4, 1H), 8.25 (s, 1H), 8.29 (s, 1H).

Example 18

Tetrabutylammonium Uracil Salt

To uracil (0.6 g, 5.4 mmol) in 10 ml DMF was added a solution of 40% (wt) NH$_4$OH (3.472 g, 5.4 mmol) in H$_2$O. The mixture was stirred at AMBIENT TEMPERATURE. After 1.5 hr, remove the solvents at 50° C. Then add DMF again and remove it and repeat this for 2 more times. It finally gave a light yellow solid which was used without further purification. $^1$H NMR (DMSO-d$_6$, 400 MHz): δ 0.93 (t, J=7.2, 12H), 1.30 (m, 8H), 1.56 (m, 8H), 3.16 (m, 8H), 4.97 (d, J=6.4, 1H), 7.34 (d, J=6.0, 1H).

Example 19

N$^3$-PMB-5-fluoro-uracil

5-Fluoro-uracil (1.3 g, 10 mmol) was dissolved in 25 ml DMF under argon, followed by the addition of Et$_3$N (1.4 ml, 10 mmol). This was cooled to 0° C. and methyl chloroformate (0.8 ml, 10 mmol) was added drop by drop. After 3 hr at 0° C., more Et$_3$N (2 ml, 15 mmol) was added, followed by the addition of PMBCl (2 ml, 15 mmol) at 0° C. After 3 hr at 0° C. and 3 hr at AMBIENT TEMPERATURE, the reaction was quenched by pouring the reaction mixture to cold H$_2$O. Then extract the product with EtOAc three times and H$_2$O once. The organic phase was dried over MgSO$_4$ and solvent evaporation gave the crude intermediate. This was redissolved in a mixture of MeOH 5 ml and CH$_2$Cl$_2$ 5 ml and was allowed to react with 30% H$_2$O$_2$ (1.13 ml, 11 mmol) and 6N NaOH 0.02 ml at 0° C. for 1 hr. Then the reaction mixture was poured into ice-cooled 2N HCl and the product was isolated by CH$_2$Cl$_2$ extraction. The organic phase was washed with H$_2$O and dried over MgSO$_4$ and solvent evaporation gave the crude product, which was purified by column chromatograph (Hexane: EtOAc=1:1). $^1$H NMR (DMSO-d$_6$, 300 MHz): δ 3.72 (s, 3H), 4.88 (s, 2H), 6.86 (d, J=8.4, 2H), 7.24 (d, J=8.7, 2H), 7.86 (d, J=5.4, 1H), 11.15 (s, 1H).

Example 20

Anti-HIV Activity

The cyclobutyl nucleoside analogs (CBN) were evaluated for their anti-HIV activity and cytotoxicity in PBM, CEM and Vero cells, according to known procedures.

The toxicity assays showed that all of the CBN's exhibited no cytotoxicity up to 100 μM. None of the CBN's proved to be inhibitors of HIV-1 in cell based assays.

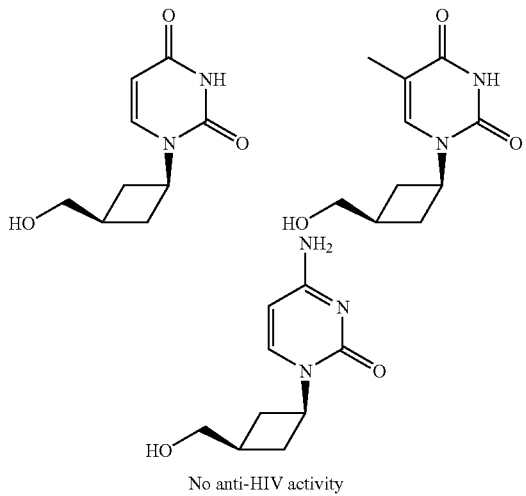

No anti-HIV activity

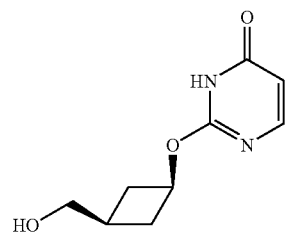

No anti-HIV activity

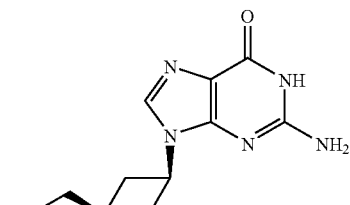

EC$_{50}$ = 0.8 μM

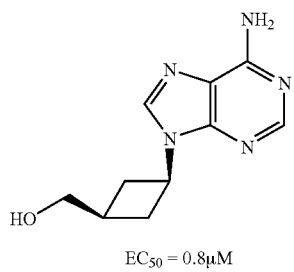

$EC_{50} = 0.8\mu M$

M. Frieden, M. Giraud. C. B. Reese and Q. Song, *J. Chem Soc., Perkin Trans.*, 1998, 2827.
V. Kaiwar, C. B. Reese, E. J. Gray and S. Neidle, *J. Chem. Soc., Perkin Trans.*, 1995, 2281

However, various CBN analogs exhibited significant inhibition of recombinant wild type, M184V and M184I HIV-RT. Therefore, the triphosphate derivative of the following cyclobutyl nucleoside:

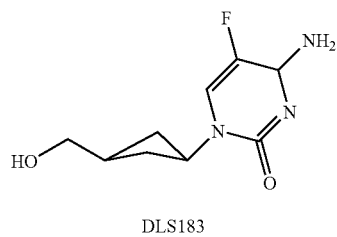

Figure 2:
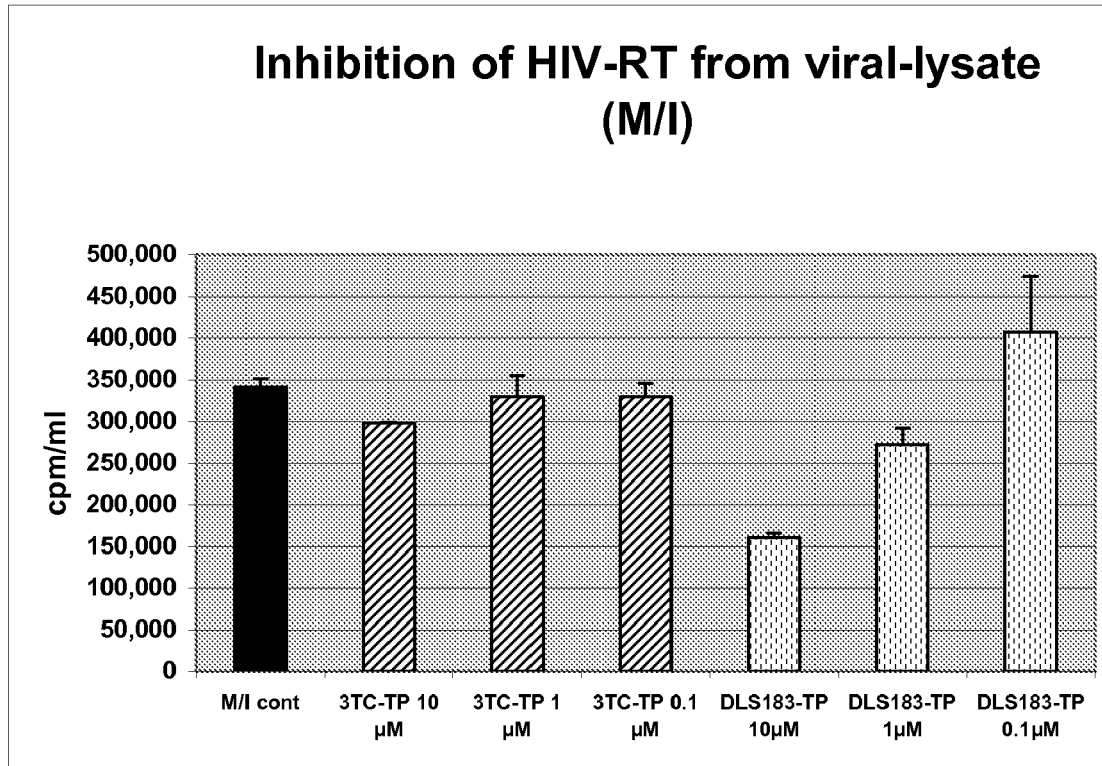
FIG. 2 is bar graphs depicting the inhibition of a M184I mutant strain of HIV reverse transcriptase (RT) from viral lysate using a cyclobutyl nucleoside of the present invention, as compared to 3TC.
Figure 3:
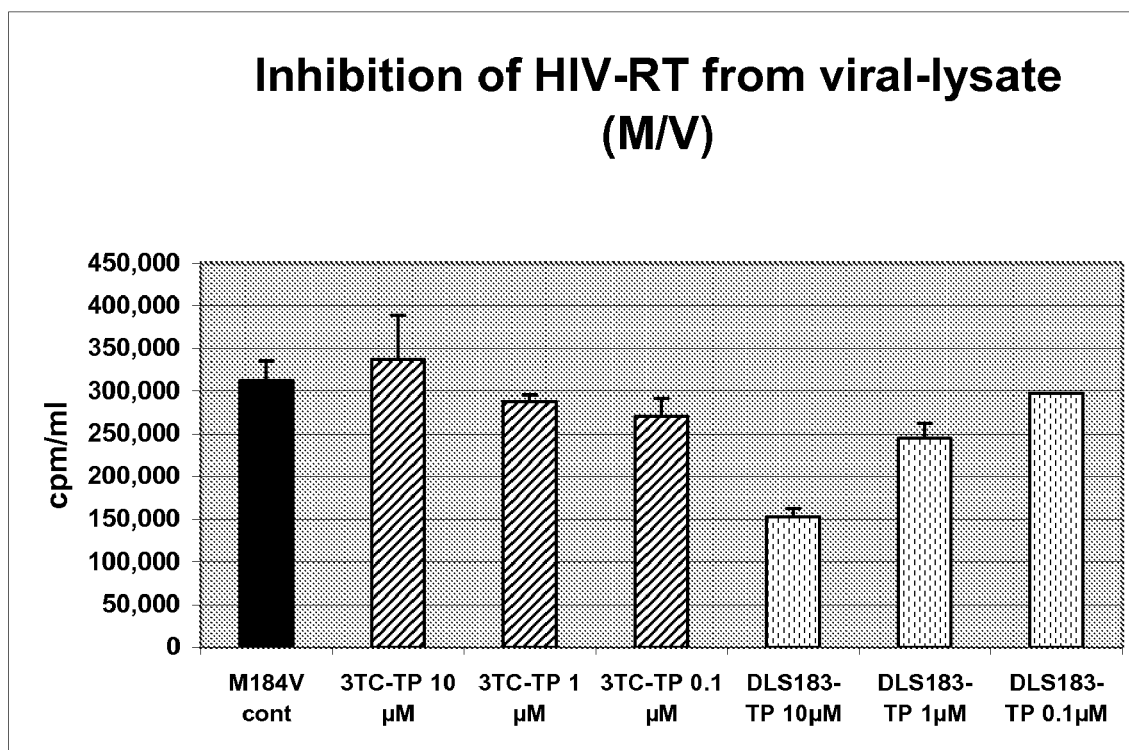
FIG. 3 is bar graphs depicting the inhibition of a M184V mutant strain of HIV reverse transcriptase (RT) from viral lysate using a cyclobutyl nucleoside of the present invention, as compared to 3TC.

DLS183 was evaluated against recombinant wild type HIV-RT, as well as the M184I and M184V mutants, according to the RT assay described in Eriksson B F, Chu C K, Schinazi R F; *Antimicrob. Agents Chemother.* 1989, 33, 1729-1734. The results are tabulated in Tables 2-5 and depicted in FIGS. 1-3.

TABLE 2

Inhibition of HIV-RT from viral-lysate (WT)

|  | cpm/ml | SD | % inhibition |
| --- | --- | --- | --- |
| WT cont | 276994.506 | 27124.182 |  |
| 3TC-TP 10 μM | 124341.312 | 5110.884 | 55 |
| 3TC-TP 1 μM | 215883.012 | 32964.78 | 22 |
| 3TC-TP 0.1 μM | 268420.2 | 31938.252 | 3.1 |
| DLS183-TP 10 μM | 134616.36 | 3065.154 | 51 |
| DLS183-TP 1 μM | 228126.312 | 34687.278 | 18 |
| DLS183-TP 0.1 μM | 280781.826 | 3857.472 | 0.01 |
| no enzyme | 71173.2 |  |  |

TABLE 3

|  | cpm/ml | SD | % Inhibition |
| --- | --- | --- | --- |
| M/I cont | 341761.452 | 9427.008 |  |
| 3TC-TP 10 μM | 298628.406 | 769.008 | 13 |
| 3TC-TP 1 μM | 329605.62 | 25588.608 | 0.03 |
| 3TC-TP 0.1 μM | 329435.346 | 16435.77 | 0.03 |
| DLS183-TP 10 μM | 160719.12 | 5023.86 | 53 |
| DLS183-TP 1 μM | 272130.486 | 19976.004 | 20 |
| DLS183-TP 0.1 μM | 407041.44 | 67797.246 | 0.01 |

TABLE 4

Inhibition of HIV-RT from viral-lysate (M/V)

|  | cpm/ml | SD | % Inhibition |
| --- | --- | --- | --- |
| M184V control | 312707.646 | 22531.224 |  |
| 3TC-TP 10 μM | 336946.272 | 51714.012 | 0.01 |
| 3TC-TP 1 μM | 288267.666 | 7702.512 | 7 |
| 3TC-TP 0.1 μM | 270239.712 | 21601.71 | 13 |
| DLS183-TP 10 μM | 152688.27 | 9583.962 | 51 |
| DLS183-TP 1 μM | 245062.692 | 16673.31 | 22 |
| DLS183-TP 0.1 μM | 297603.432 |  | 5 |

TABLE 5

Comparison of Inhibition of HIV RT in Cell-Free Assays

| HIV RT* | Inhibition of RT Activity ($IC_{50}$, μM)** | | | |
| --- | --- | --- | --- | --- |
|  | 3TC-TP | | CBN-TP | |
| Recombinant HIV RT (WT) | 2.99 | 0.7 | 4.74 | 0.34 |
| HIV RT (WT) | 6.53 | 1.46 | 6.85 | 1.79 |
| HIV RT (M/I) | >10 |  | 6.06 | 0.75 |
| HIV RT (M/V) | >10 |  | 6.91 | 1.50 |

*All the HIV-RT used, except the recombinant RT, were obtained from viral lysates from PBMC infected with respective HIV.
**Values represented are from triplicates from one experiment.

Example 21

4-Benzyloxy-but-2-enoic Acid Ethyl Ester

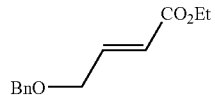

In a three-neck flask under argon, dry 1,2-DME 20 mL, followed by the addition of triethyl phosphonoacetate (1.4 mL, 6.99 mmol), were added dropwisely to give a colorless solution. NaH (0.19 g, 7.9 mmol) was added in portions. $H_2$ gas was immediately produced. After stirring for 30 min, to this light yellow solution, benzyloxyacetaldehyde (1 mL, 7.12 mmol) was added to give still a yellow solution. This was left stirring at room temperature. After 3 hr, the reaction was quenched with the addition of 5 mL 0.1 N HCl. The aqueous phase was extracted with $Et_2O$ three times and the combined organic phase was dried over $MgSO_4$ and solvent evaporation gave an oily crude product, which was purified by silica gel flash chromatography (Hexane: EtOAc=9:1, Rf=0.27) to give 0.78 g (50%) of the desired product. $^1H$ NMR ($CDCl_3$, 600 MHz): δ 1.28-1.31 (t, 3H, J=7.2), 4.18-4.23 (m, 4H), 4.57 (s, 2H), 6.12-6.16 (td, 1H, J=15.6, 1.8), 6.97-7.01 (td, 1H, J=15.6, 4.2), 7.29-7.37 (m, 5H). $^{13}C$ NMR ($CDCl_3$, 150 MHz): δ 14.40, 60.55, 68.77, 72.90, 121.55, 127.78, 127.97, 128.63, 137.88, 144.38, 166.46. MS (FAB): expected for $C_{13}H_{16}O_3$ (M+H)$^+$ 221.26. Found 221.11719. IR (neat) $v_{max}$ 3031, 2981, 2857, 1720, 1663, 1454, 1367, 1301, 1276, 1177, 1119, 1040, 967, 737, 698.

Example 22

3-Benzyloxymethyl-2-fluoro-pentanedioic Acid Diethyl Ester

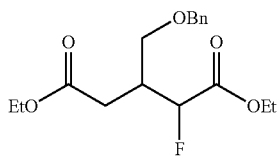

In a 10 mL flask with 4-benzyloxy-but-2-enoic acid ethyl ester (0.1 g, 0.45 mmol) inside, dry $CH_2Cl_2$ 3 mL was added under argon. This was cooled to 0° C., TMSOTf (0.08 mL, 0.45 mmol) was added drop by drop. After stirring for 10 min, ethyl α-fluoro silyl enol ether (0.08 g, 0.45 mmol) was added dropwisely at 0° C. This was left stirring at 0° C. for 1.5 hr, at room temperature for 5 hr and refluxing for 25 hr. After cooling to room temperature, $H_2O$ was added and the aqueous phase was extracted with $CH_2Cl_2$ three times and the combined organic phase was dried over $MgSO_4$ and the solvent was evaporated to give an oily product which was purified by silica gel flash chromatography (Hexane: EtOAc=6:1, Rf==0.42) to give 87.7 mg (59.3%) of the product. $^1$H NMR (CDCl$_3$, 400 MHz): δ 1.18-1.32 (m, 6H), 2.32-2.54 (m, 2H), 2.77-2.98 (m, 1H), 3.44-3.57 (m, 2H), 4.07-4.30 (m, 4H), 4.45-4.54 (m, 2H), 4.96-5.09 (dd, J=48, 3.2, 1H, minor isomer), 5.10-5.22 (dd, J=48, 3.2, 1H, major isomer), 7.24-7.36 (m, 5H). $^{13}$C NMR (CDCl$_3$, 100 MHz): δ 14.23, 30.96-31.02 (d, J=6.0), 32.63, 38.51-38.70 (d, J=19), 60.87, 61.73, 67.94-67.99 (d, J=5.0), 68.60-68.63 (d, J=3.0), 73.29-73.35 (d, J=6.0), 86.96-88.81 (d, J=185), 87.54-89.40 (d, J=186), 127.77, 127.87, 128.54, 137.99-138.04 (d, J=5.0), 168.92-169.42 (t, J=25.8), 171.80-171.85 (d, J=5.0). MS (FAB): expected for $C_{17}H_{23}FO_5$ (M+H)$^+$ 327.36. Found 327.16020. IR (neat) $v_{max}$ 2983, 2938, 2907, 2872, 1760, 1734, 1455, 1374, 1208, 1183, 1090, 1029, 739, 699.

Example 23

3-(Hydroxylmethyl)-cyclobutanone

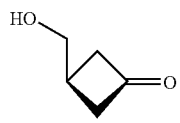

In a 25 mL flask with 3-oxocyclobutanecarboxylic acid (0.1 g, 0.88 mmol) inside, 3 mL dry THF was added. This was cooled to −78° C., after 30 min, borane-dimethyl sulfide (2 M in THF, 0.53 mL, 1.06 mmol) was added dropwisely. After 5 min, the dry ice-acetone bath was removed and the reaction mixture was allowed to warm up to room temperature. After stirring for overnight, the reaction mixture was quenched by adding 3 mL dry MeOH. The volatile were removed and the reaction mixture was subsequently purified by silica gel flash chromatography purification. (0.065 g, 74%) ($CH_2Cl_2$: MeOH=8:1, Rf=0.25). $^1$H NMR (CDCl$_3$, 400 MHz): δ 2.70 (m, 1H), 2.84-2.92 (m, 2H), 3.08-3.18 (m, 2H), 3.59 (d, J=6.4, 2H). $^{13}$C NMR (CDCl$_3$, 100 MHz): δ 30.43, 49.57, 65.50, 208.17.

Example 24

3-(tert-butyl-diphenyl-siloxymethyl)cyclobutanone

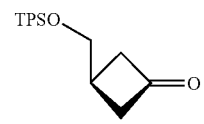

To a 25 mL flask containing 3-(hydroxylmethyl)-cyclobutanone (0.2 g, 2 mmol), dry DMF (5 mL), imidazole (0.31 g, 4.55 mmol), TPSCl (0.62 mL, 2.38 mmol) were added. After reacting for 5.5 hr, the reaction mixture was diluted with 20 mL $CH_2Cl_2$, and washed with 10 mL $H_2O$ twice, 10 mL saturated NaHCO$_3$ once and 10 mL brine once. The organic phase was dried over $MgSO_4$ and solvent evaporation gave the crude product, which was purified by silica gel flash chromatography (Hexane: EtOAc=9:1) to give 0.61 g (90%, Rf=0.36) of the product. $^1$H NMR (CDCl$_3$, 400 MHz): δ 1.06 (s, 9H), 2.55-2.65 (m, 1H), 2.90-3.10 (m, 4H), 3.79-3.81 (d, J=8.0, 2H), 7.34-7.47 (m, 6H), 7.64-7.66 (m, 4H). $^{13}$C NMR (CDCl$_3$, 100 MHz): δ 19.53, 25.82, 27.04, 49.45, 66.19, 127.97, 130.01, 133.60, 135.80, 208.05. MS (FAB): expected for $C_{13}H_{16}O_3$ (M+H)$^+$ 221.26. Found 221.11719. MS (FAB): expected for $C_{21}H_{26}O_2Si$ (M+H)$^+$ 339.52. Found 339.17770. IR (neat) $v_{max}$ 2958, 2931, 2894, 2857, 1784, 1472, 1428, 1389, 1112, 741, 702.

Example 25 cis-2-Fluoro-cis-3-(benzyloxymethyl)cyclobutanol

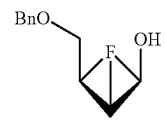

$^1$H NMR (CDCl$_3$, 400 MHz): δ 1.86 (m, 1H), 2.36-2.54 (m, 2H), 3.00 (d, J=10, 1H), 3.55-3.59 (m, 1H), 3.64-3.68 (m, 1H), 4.19 (m, 1H), 4.56 (s, 2H), 5.07-5.21 (m, J=56, 1H), 7.27-7.38 (m, 5H). MS (FAB): expected for C$_{12}$H$_{15}$FO$_2$ (M+H)$^+$ 211.24. Found 211.11286.

Example 26

Benzyl-(3-benzyloxymethyl-2-fluoro-cyclobutyl)-amine

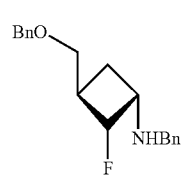

In a 25 mL flask with trans-2-fluoro-3-(benzyloxymethyl) cyclobutanone (0.20 g, 0.96 mmol) inside, dry 1,2-DCE 3.4 mL was added under argon to give a colorless solution. To this, benzylamine (0.11 mL, 1.01 mmol) was added to give still a colorless solution. After stirring for 5 min, sodium triacetoxyborohydride (0.29 g, 1.37 mmol) was added all at once to give a white emulsion. Then AcOH (0.06 mL, 1.05 mmol) was added drop by drop. After 5 min, it gave a yellow solution and this was left stirring for 2 hr and then the reaction was quenched by sat. NaHCO$_3$. The organic phase was separated and the aqueous phase was extracted with EtOAc twice. The combined organic phase was dried over MgSO$_4$ and the crude product was purified by silica gel flash chromatography (Hexane: EtOAc=3:1) to give 0.19 g (65%, Rf=0.18) of the product. $^1$H NMR (CDCl$_3$, 600 MHz): δ 1.81-1.95 (m, 3H), 2.80-2.89 (m, 1H), 3.46-3.56 (m, 3H), 3.76-3.84 (m, 3H), 4.51-4.55 (m, 2H), 4.89-5.00 (td, 1H, J=54.6, 4.8), 7.25-7.37 (m, 10H).

Example 27

3-Benzyloxymethyl-2-fluoro-cyclobutylamine

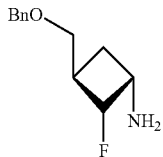

Benzyl-(3-benzyloxymethyl-2-fluoro-cyclobutyl)-amine (0.34 g, 1.21 mmol) was dissolved in 10 mL MeOH and this was treated with 20% Pd(OH)$_2$ on carbon (0.07 g, 0.11 mmol). This was subjected to the hydrogenolysis conditions (50 psi). After 22 hr, the reaction mixture was filtered through celite and the filtrated was concentrated and was purified by silica gel flash chromatography (Hexane: EtOAc=1:1) to give 0.16 g (63%, Rf=0.30 (CH$_2$Cl$_2$: MeOH=15:1)). $^1$H NMR (CDCl$_3$, 400 MHz): δ 2.08-2.16 (m, 2H), 2.96-3.12 (m, 1H), 3.52-3.64 (m, 2H), 3.88-3.94 (m, 1H), 4.55 (s, 2H), 5.03-5.19 (td, 1H, J=52.8, 6.0), 7.25-7.38 (m, 5H). $^{13}$C NMR (CDCl$_3$, 100 MHz): δ 23.12-23.21 (d, J=9.0), 42.13-42.34 (d, J=21), 48.30, 70.07, 74.39, 87.46-89.63 (d, J=217), 128.98, 129.05, 129.61, 139.63. MS (FAB): expected for C$_{12}$H$_{16}$FNO (M+H)$^+$ 210.26. Found 210.12885.

Example 28

1-Benzyl-3-(3-benzyloxymethyl-2-fluoro-cyclobutyl)-urea

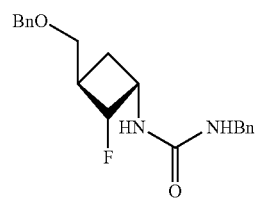

In a 25 mL flask with benzyl-(3-benzyloxymethyl-2-fluoro-cyclobutyl)-amine (25.8 mg, 0.12 mmol) inside, dry CH$_2$Cl$_2$ 2 mL was added under argon at room temperature to give a colorless solution, followed by the addition of Et$_3$N (0.02 mL, 0.14 mmol). After stirring for 5 min, 4-nitrophenyl-N-benzylcarbamate (32.1 mg, 0.12 mmol) was added to give a yellow solution. This was left stirring at room temperature for 10 hr and the reaction was quenched by adding 10 mL CH$_2$Cl$_2$. The organic phase was washed with 1 M NaOH 10 mL, H$_2$O 10 mL and brine 10 mL and was dried over MgSO$_4$. Solvent evaporation gave the crude product 42 mg that is pure enough and crystallization gave the pure product 38 mg (90%) as a white solid.

$^1$H NMR (CDCl$_3$, 400 MHz): δ 1.96-2.01 (m, 2H), 2.65-2.80 (m, 1H), 3.48-3.58 (m, 2H), 4.31-4.36 (m, 3H), 4.52 (s, 2H), 4.82-4.99 (td, 1H, J=54.8, 5.2), 7.19-7.39 (m, 10H). $^{13}$C NMR (CDCl$_3$, 100 MHz): δ 27.11-27.19 (d, J=7.6), 41.75-41.96 (d, J=21), 47.92, 48.44-48.51 (d, J=7.0), 71.12-71.16 (d, J=4.0), 74.26, 90.34-92.48 (d, J=214), 128.14, 128.30, 128.84, 128.96, 129.56, 129.62, 139.81, 141.35, 160.85. MS (FAB): expected for C$_{20}$H$_{23}$FN$_2$O$_2$ (M+H)$^+$ 343.41. Found 343.18178. IR (neat) ν$_{max}$ 2923, 2851, 1558, 1458, 1378, 1265, 895, 740, 704. The absolute stereochemistry was established by X-ray crystallographic analyses.

Example 29

N4-Acetyl-2-[trans-2-fluoro-cis-3-(benzyloxymethyl)-cyclobutyl]cytosine

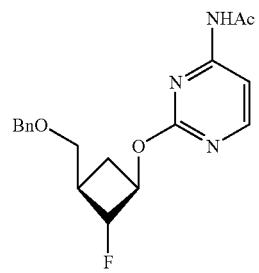

In a 25 mL flask with cis-2-fluoro-trans-3-(benzyloxymethyl)cyclobutanol 144 (0.2 g, 0.95 mmol), N4-acetyl cytosine (0.22 g, 1.44 mmol) and Ph$_3$P (0.62 g, 2.36 mmol) inside, dry THF 10 mL was added. This was cooled to 0° C. and was treated with DEAD (40% in toluene, 1 mL, 2.38 mmol) slowly. The reaction mixture was allowed to warm up to room temperature gradually and was left stirring for 24 hr. Then the products were concentrated under reduced pressure and the residue was fractionated by short-column silica gel flash chromatography (Hexane: EtOAc=3:1 to Hexane: EtOAc=1:1) and the appropriate fractions were purified again by silica gel flash chromatography (Hexane: EtOAc=1:1) to give the undesired O2-coupled byproduct (40 mg, 14%, Rf=0.36 (Hexane: EtOAc=1:1)).

Example 30

N3-Benzoyl-5-Fluoro-1-[trans-2-fluoro-cis-3-(benzyloxymethyl)cyclobutyl]-uracil

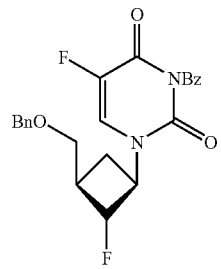

In a 250 mL flask with cis-2-fluoro-trans-3-(benzyloxymethyl)cyclobutanol (0.7 g, 3.33 mmol), Ph$_3$P (2.19 g, 8.35 mmol) and N3 benzoyl protected 5-fluorouracil (1.17 g, 5 mmol) inside, dry THF 50 mL was added to give a colorless solution. This was cooled to 0° C. and 10 min later, DIAD (1.64 mL, 8.33 mmol) was added drop by drop to give a yellow solution. This was left stirring and allowed to warm up to room temperature gradually. After 12 hr, the products were concentrated under reduced pressure and the residue was fractionated by short-column silica gel flash chromatography (Hexane: EtOAc=3:1 to Hexane: EtOAc=1:1) and the appropriate fractions were purified again by silica gel flash chromatography to give an oily Ni-coupled desired product (0.14 g, 10%, Rf=0.54 (Hexane: EtOAc=2:1)) with some O$_2$-coupled byproduct (0.11 g, 8%, Rf=0.31 (Hexane: EtOAc=2:1)). IR (neat) $\nu_{max}$ 2925, 2854, 1754, 1716, 1667, 1450, 1373, 1286, 1248, 1107, 1057.

Example 31 cis-2-Fluoro-trans-3-(benzyloxymethyl)cyclobutyl-triflate

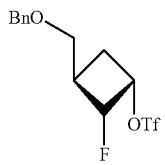

In a 25 mL flask with cis-2-fluoro-trans-3-(benzyloxymethyl)cyclobutanol (0.1 g, 0.48 mmol) inside, dry CH$_2$Cl$_2$ 10 mL was added under argon to give a colorless solution. Then DMAP (0.06 g, 0.49 mmol) was added all at once. The reaction mixture was cooled to 0° C. and Tf$_2$O (0.56 mL, 3.33 mmol) was added drop by drop. After stirring for 1 hr, the solvent was evaporated and the crude mixture was used directly in the next step. $^1$H NMR (CDCl$_3$, 600 MHz): δ 2.22-2.26 (m, 1H), 2.38-2.44 (m, 1H), 2.99-3.04 (m, 1H), 3.45-3.47 (m, 1H), 3.60-3.62 (m, 1H), 4.51-4.56 (m, 2H), 4.97-5.06 (td, J=54, 1H), 5.30-5.32 (m, 1H), 7.29-7.37 (m, 5H). IR (neat) $\nu_{max}$ 2956, 2862, 1725, 1454, 1435, 1361, 1206, 1129, 870, 749, 699.

Example 32

5-Fluoro-2-[trans-2-fluoro-cis-3-(benzyloxymethyl)-cyclobutyl]cytosine

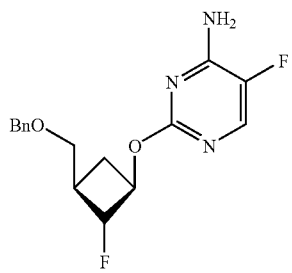

To a 25 mL three-neck flask with cis-2-fluoro-trans-3-(benzyloxymethyl)-cyclobutyl-mesylate (0.46 g, 1.6 mmol), 5-fluorocytosine (0.41 g, 3.18 mmol), K$_2$CO$_3$ (0.44 g, 3.19 mmol) and 18-crown-6 (0.84 g, 3.18 mmol) inside, dry DMF 8 mL was added under argon at room temperature. This was heated to 120° C. for 24 hr and then DMF was removed in vacuo. The crude mixture was purified by silica gel flash chromatography (CH$_2$Cl$_2$: MeOH=40:1) to give the O$_2$-coupled product (0.3 g, Rf=0.26 (CH$_2$Cl$_2$: MeOH=40:1)) in 60% yield with the Ni-coupled product (0.04 g, Rf=0.12 (CH$_2$Cl$_2$: MeOH=40:1)) in 7.5% yield. $^1$H NMR (CDCl$_3$, 600 MHz): δ 1.48 (m, 1H), 1.65 (broad s, 1H), 2.31 (m, 1H), 2.43 (m, 1H), 3.56 (m, 1H), 3.59 (m, 1H), 4.54 (m, 2H), 4.82-4.91 (td, J=54.6, 6.6, J=1H), 5.12 (m, 2H), 7.28-7.36 (m, 5H), 7.90 (d, J=3.0, 1H). $^{13}$C NMR (CDCl$_3$, 100 MHz): δ 22.05-22.28 (d, J=23), 34.92-35.12 (d, J=20), 69.70, 72.67-72.90 (d, J=23), 73.03, 90.50-92.73 (d, J=223), 127.58, 127.67, 128.43, 138.22, 140.65-140.85 (d, J=20), 141.44-143.90 (d, J=246), 154.74-154.87 (d, J=13), 159.39. MS (FAB): expected for C$_{16}$H$_{17}$F$_2$N$_3$O$_2$ (M+Li)$^+$ 328.32. Found 328.28. IR (neat) $\nu_{max}$ 3332, 2953, 1638, 1508, 1420, 1389, 1333, 1045.

Example 33

5-Fluoro-1-[trans-2-fluoro-cis-3-(benzyloxymethyl)cyclobutyl]cytosine

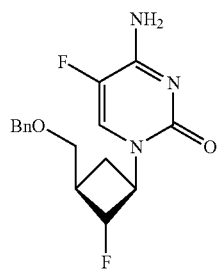

¹H NMR (CDCl₃, 600 MHz): δ 1.73-1.78 (q, J=10.2, 1H), 2.34-2.50 (m, 2H), 3.52-3.54 (m, 1H), 3.65-3.68 (m, 1H), 4.54-4.60 (m, 2H), 4.83-4.90 (m, 1H), 4.98-5.09 (td, J=54, 7.2, 1H), 7.29-7.38 (7H). ¹³C NMR (CDCl₃, 100 MHz): δ 20.10-20.31 (d, J=21), 36.74-36.94 (d, J=20), 54.34-54.57 (d, J=23), 68.15, 73.55, 88.35-90.61 (d, J=226), 124.82-125.16 (d, J=34), 127.83, 128.13, 128.75, 137.96, 139.94-142.32 (d, J=238), 150.37, 158.01-158.26 (d, J=25). MS (FAB): expected for $C_{16}H_{17}F_2N_3O_2$ (M+H)⁺ 321.32. Found 322.13622. IR (neat) $v_{max}$ 3053, 2925, 2854, 1687, 1613, 1513, 1454, 1265, 1116, 739, 705.

Example 34

5-Fluoro-2-[trans-2-fluoro-cis-3-(hydroxymethyl)-cyclobutyl]cytosine

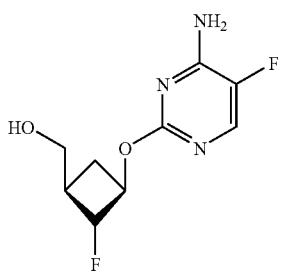

In a 25 mL flask with 5-fluoro-2-[trans-2-fluoro-cis-3-(benzyloxymethyl)-cyclobutyl] cytosine (0.43 g, 1.34 mmol) inside, dry CH₂Cl₂ 4 mL was added under argon to give a colorless solution. This was cooled to −78° C., BCl₃ (1.0 M in CH₂Cl₂, 4 mL, 4.02 mmol) was added drop by drop. After 8 hr, the reaction was quenched by adding 7 N NH₃ in MeOH (4.7 mL, 32.9 mmol) slowly. The products were then concentrated under reduced pressure and the residue was purified by silica gel flash chromatography (CH₂Cl₂ only to CH₂Cl₂: MeOH=10:1) to give the desired product (0.15 g) in 48% yield. The trace impurities were further removed by reverse phase preparative HPLC (H₂O and CH₃CN gradient) to give a white solid. ¹H NMR (CD₃OD, 400 MHz): δ 1.29-1.37 (m, 1H), 2.12-2.25 (m, 1H), 2.36-2.47 (m, 1H), 3.61-3.72 (m, 2H), 4.69-4.86 (td, J=55.2, 6.8, 1H), 4.98-5.08 (m, 1H), 7.80-7.81 (d, J=4.0). ¹³C NMR (CD₃OD, 100 MHz): δ 22.57-22.80 (d, J=23), 38.10-38.29 (d, J=19), 62.48, 74.10-74.32 (d, J=22), 91.12-93.34 (d, J=222), 140.81-141.03 (d, J=22), 142.58-145.02 (d, J=244), 157.04-157.18 (d, J=14), 160.88. MS (FAB): expected for $C_9H_{11}F_2N_3O_2$ (M+H)⁺ 232.20. Found 232.08927. IR (neat) $v_{max}$ 3386, 2958, 1642, 1502, 1420, 1337, 1212, 1042, 949, 779.

Example 35

1-[trans-2-Fluoro-cis-3-(benzyloxymethyl)cyclobutyl]uracil

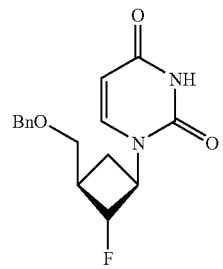

In a 25 mL three-neck flask with tetrabutylammonium uracil salt (0.88 g, 3 mmol) inside, dry DMF 7 mL was added under argon to give a light yellow solution. After stirring for 5 min, a DMF solution of cis-2-fluoro-trans-3-(benzyloxymethyl)cyclobutyl-mesylate (0.6 g, 2.5 mmol) was added with the color changing from light yellow to orange yellow. The solution was heated for 24 hours at 120° C., then stirred overnight at ambient temperature. AcOH 0.2 mL was added, after stirring for 10 min, DMF was removed and EtOAc was added, which was washed with H₂O three times and brine once. The organic phase was dried over MgSO₄ and solvent evaporation gave the crude product, which was purified by silica gel flash chromatography (Hexane: EtOAc=3:1 to Hexane: EtOAc=1:1) to give the desired N1-coupled product 0.18 g (29%) with double alkylation products (7.3%). ¹H NMR (CDCl₃, 400 MHz): δ 1.75 (m, 1H), 2.26-2.49 (m, 2H), 3.51-3.54 (m, 1H), 3.63-3.66 (m, 1H), 4.54 (m, 2H), 4.79 (m, 1H), 5.00-5.13 (td, J=54.8, 6.4, 1H), 5.68 (d, J=8.0, 1H), 7.22-7.24 (d, J=8.0, 1H), 7.25-7.36 (m, 5H), 10.09 (s, 1H). ¹³C NMR (CDCl₃, 100 MHz): δ 20.33 (d, J=20.7), 36.97 (d, J=19.7), 54.58 (d, J=23.4), 68.34, 73.52, 89.48 (d, J=226.3), 102.96, 127.87, 128.11, 128.72, 138.03, 141.15, 150.90, 163.53. MS (FAB): expected for $C_{16}H_{17}FN_2O_3$ (M+Li) 311.32. Found 311.2. IR (neat) $v_{max}$ 2924, 2853, 1690, 1461, 1382, 1276, 1071, 713.

Example 36

1,3-Bis-(3-benzyloxymethyl-2-fluoro-cyclobutyl)-1H-pyrimidine-2,4-dione

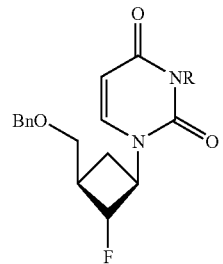

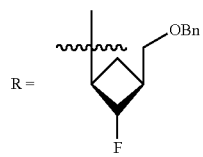

R =

¹H NMR (CDCl₃, 400 MHz): δ 1.73-1.80 (m, 1H), 2.12-2.29 (m, 2H), 2.32-2.56 (m, 3H), 3.53-3.72 (m, 4H), 4.53-4.60 (m, 4H), 4.74-4.86 (m, 1H), 4.97-5.14 (td, J=53.6, 7.6), 5.30-5.41 (m, 1H), 5.59-5.77 (m, 1H), 5.68-5.70 (dd, 1H, J=8.0, 1.6), 7.16-7.18 (dd, 1H, J=8.0, 0.8), 7.28-7.39 (m, 10H). ¹³C NMR (CDCl₃, 75 MHz): δ 19.55-19.82 (d, J=20.2), 20.16-20.44 (d, J=21), 36.89-37.15 (d, J=19.5), 37.55-37.81 (d, J=19.5), 51.35-51.74 (d, 29.3), 55.07-55.38 (d, J=23.3), 68.25, 71.62, 73.25, 73.56, 87.94-90.86 (d, J=219), 89.04-91.94 (d, J=217.5), 102.63, 127.82, 127.89, 128.15, 128.58, 128.76, 138.05-138.51 (d, J=34.5), 139.11, 151.50, 163.03, 174.57.

MS (FAB): expected for $C_{28}H_{30}F_2N_2O_4$ (M+Li)⁺ 503.55. Found 503.4. IR (neat) $v_{max}$ 2926, 2857, 1718, 1663, 1454, 1374, 1287, 1099, 739, 699.

Example 37

N3-Butyl-1-[trans-2-fluoro-cis-3-(benzyloxymethyl)cyclobutyl]uracil

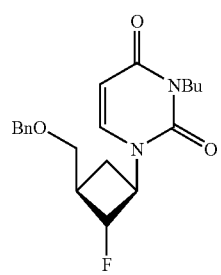

In a 10 mL flask with tetrabutylammonium uracil salt (0.26 g, 0.74 mmol) inside, dry DMF 2 mL was added under argon to give a light yellow solution. After stirring for 5 min, a DMF solution of cis-2-fluoro-trans-3-(benzyloxymethyl)cyclobutyl-mesylate (0.07 g, 0.24 mmol) was added. The solution was heated for 24 hours at 120° C., then stirred overnight at ambient temperature. AcOH 0.05 mL was added, stirred for 10 min, then DMF was removed and EtOAc was added, which was washed with H₂O three times and brine once. The organic phase was dried over MgSO₄ and solvent evaporation gave the crude product, which was purified by silica gel flash chromatography (Hexane: EtOAc=3:1 to Hexane: EtOAc=1:1) to give the desired 1-[trans-2-fluoro-cis-3-(benzyloxymethyl)cyclobutyl]uracil 14.8 mg (20%), N3-butyl-1-[trans-2-fluoro-cis-3-(benzyloxymethyl)cyclobutyl]uracil 13.1 mg (15%) and butylation products of uracil.

Example 38

5-Fluoro-1-[trans-2-fluoro-cis-3-(benzyloxymethyl)cyclobutyl]uracil

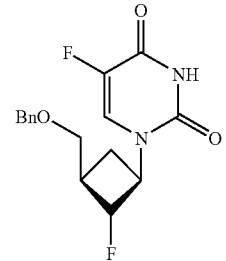

In a 10 mL flask with tetrabutylammonium 5-fluorouracil (0.13 g, 0.35 mmol) inside, dry DMF 2 mL was added under argon. In another flask with cis-2-fluoro-trans-3-(benzyloxymethyl)cyclobutyl-mesylate (0.10 g, 0.35 mmol) inside, dry DMF 1 mL was added and this was added to the previous flask. The mixture was allowed to heat to 120° C. for 24 hr and then the solvent was removed and the crude material was purified by silica gel flash chromatography (Hexane: EtOAc=3:1 to Hexane: EtOAc=1:3) to give the desired 5-fluoro-1-[trans-2-fluoro-cis-3-(benzyloxymethyl)cyclobutyl]uracil (0.02 g, 20%, Rf=0.24, Hexane: EtOAc=1:1) and 5-fluoro-3-[trans-2-fluoro-cis-3-(benzyloxymethyl)cyclobutyl]uracil (2.8 mg, 2.8%) and 1,3-bis-(3-benzyloxymethyl-2-fluoro-cyclobutyl)-5-fluoro-1H-pyrimidine-2,4-dione (8.1 mg, 4.5%). ¹H NMR (CDCl₃, 600 MHz): δ 1.75-1.80 (m, 1H), 2.35-2.48 (m, 2H), 3.53-3.55 (m, 1H), 3.66-3.69 (m, 1H), 4.55-4.60 (m, 2H), 4.82-4.89 (m, 1H), 5.00-5.11 (td, J=54, 6.6, 1H), 7.30-7.38 (m, 5H). ¹³C NMR (CDCl₃, 100 MHz): δ 20.04-20.25 (d, J=20.5), 36.76-36.96 (d, J=19.7), 54.41-54.64 (d, J=23.5), 68.00, 73.63, 88.19-90.45 (d, J=225.3), 125.23-125.56 (d, J=32.6), 127.87, 128.21, 128.67, 128.81, 137.92, 139.71-142.08 (d, J=237.5), 149.34, 156.72-156.98 (d, J=26.5). MS (FAB): expected for $C_{16}H_{16}F_2N_2O_3$ (M+Li)⁺ 329.31. Found 329.1. IR (neat) $v_{max}$ 3072, 2959, 2925, 2854, 1701, 1655, 1452, 1379, 1274, 1071, 893, 763, 715.

Example 39

5-Fluoro-3-[trans-2-fluoro-cis-3-(benzyloxymethyl)cyclobutyl]uracil

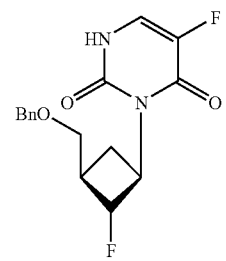

$^{1}$H NMR (CDCl$_3$, 600 MHz): δ 2.14-2.22 (m, 1H), 2.27-2.34 (m, 1H), 2.44-2.56 (m, 1H), 3.65-3.70 (m, 2H), 4.57 (s, 2H), 5.26-5.34 (m, 1H), 5.65-5.76 (td, J=56.4, 6.6), 6.98-7.00 (m, J=6.0), 7.27-7.39 (m, 5H), 9.20-9.21 (d, J=4.8). $^{13}$C NMR (CDCl$_3$, 100 MHz): δ 19.17-19.37 (d, J=20), 37.61-37.81 (d, J=20), 51.75-51.99 (d, J=24), 70.99, 73.31, 88.66-90.84 (d, J=218), 122.48-122.80 (d, J=32), 127.82, 127.95, 128.67, 128.84, 138.44, 139.38-142.00 (d, J=262), 151.37, 158.12. MS (FAB): expected for C$_{16}$H$_{16}$F$_2$N$_2$O$_3$ (M+Li)$^+$ 329.31. Found 329.1.

Example 40

N3-Benzyl-5-fluoro-1-[trans-2-fluoro-cis-3-(benzyloxymethyl)cyclobutyl]-uracil

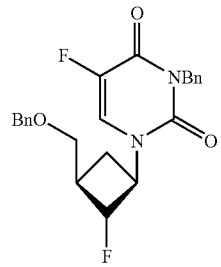

In a sealed tube with N3-benzyl protected 5-fluorouracil (0.03 g, 0.14 mmol) inside, dry chlorobenzene 1 mL was added. Then DBU (0.02 mL, 0.13 mmol) was added to give a colorless solution. This was treated with a chlorobenzene solution of cis-2-fluoro-trans-3-(benzyloxymethyl)cyclobutyl-mesylate (35 mg, 0.12 mmol) and the reaction mixture was heated to 120° C. for 24 hr. After cooling to room temperature, the mixture was washed with citric acid once, H$_2$O once and brine once. The organic phase was dried over MgSO$_4$ and solvent evaporation gave the crude product that was purified by silica gel flash chromatography (Hexane: EtOAc=3:1) to give the desired N1-coupled product (22.4 mg, 44.7%, Rf=0.26 (Hexane: EtOAc=3:1)) and O2-coupled byproduct (3.2 mg, 6.4%, Rf=0.32 (Hexane: EtOAc=3:1)). IR (neat) v$_{max}$ 3054, 2927, 2855, 1718, 1684, 1664, 1455, 1380, 1265, 1078, 896, 738, 704.

Example 41

N3-Benzyl-5-fluoro-1-[trans-2-fluoro-cis-3-(hydroxylmethyl)cyclobutyl]-uracil

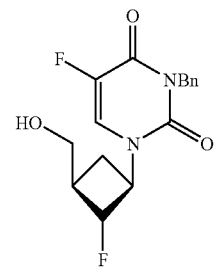

In a three-neck flask with N3-benzyl-5-fluoro-1-[trans-2-fluoro-cis-3-(benzyloxymethyl)-cyclobutyl]uracil (32 mg, 0.08 mmol) inside, 4 mL o-xylene was added under argon to give a light yellow solution. BBr$_3$ (1.0 M in hexane, 0.4 mL, 0.4 mmol) was added drop by drop at room temperature. After refluxing for 22 hr, the reaction mixture was cooled to room temperature and treated with 2 mL MeOH. After stirring for 1 hr, the solvent was evaporated and the crude mixture was subjected to silica gel flash chromatography (CH$_2$Cl$_2$: MeOH=80:1 to CH$_2$Cl$_2$: MeOH=10:1) to give the O-debenzylation product (12.5 mg, 50%, Rf=0.1, Hexane: EtOAc=1:1).

Example 42

N3-Benzyl-1-[trans-2-fluoro-cis-3-(hydroxylmethyl)cyclobutyl]uracil

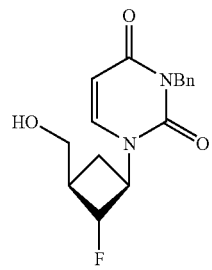

In a 50 mL flask charged with argon and a condenser, 10% Pd/C (1.33 g, 0.01 mol) was added. Then N3-benzyl-5-fluoro-1-[trans-2-fluoro-cis-3-(benzyloxymethyl)cyclobutyl]-uracil (0.44 g, 1.07 mmol) and ammonium formate (0.34 g, 5.39 mmol) dissolved in dry MeOH was added to it under argon at room temperature. An empty balloon was then put on the top of the condenser. After refluxing for 24 hr, the crude mixture was filtered through celite and the solvent was evaporated and the residue was purified by silica gel flash chromatography (CH$_2$Cl$_2$: MeOH=10:1) to give 35.75 mg (11%, Rf=0.54 (Hexane: EtOAc=1:3)) of N3-benzyl-1-[trans-2-fluoro-cis-3-(hydroxylmethyl)cyclobutyl]uracil and 16 mg (7%, Rf=0.14 (Hexane: EtOAc=1:3)) of 1-[trans-2-fluoro-cis-3-(hydroxylmethyl)cyclobutyl]uracil.

Example 43

N3-PMB-5-Fluoro-2-[trans-2-fluoro-cis-3-(benzyloxymethyl)cyclobutyl]-uracil

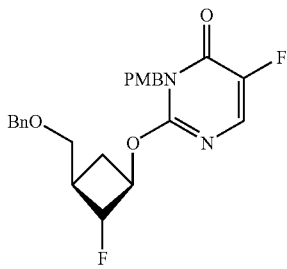

$^{1}$H NMR (CDCl$_3$, 400 MHz): δ 1.48 (m, 1H), 2.32 (m, 1H), 2.4 (m, 1H), 3.54 (m, 1H), 3.63 (m, 1H), 3.74 (s, 3H), 4.58 (m, 2H), 4.85-4.99 (td, J=54.8, 6.4, 1H), 5.12 (m, 2H), 5.18 (m, 1H), 6.78 (m, 4H), 7.29-7.40 (m, 5H), 7.55 (d, J=1.6, 1H). $^{13}$C

NMR (CDCl₃, 100 MHz): δ 21.58-21.79 (d, J=21), 35.01-35.21 (d, J=20), 45.07, 55.41, 68.60, 73.31, 74.17-74.39 (d, J=22), 89.10-91.34 (d, J=224), 114.10, 127.70, 127.78, 127.96, 128.66, 130.72, 133.90-134.13 (d, J=23), 138.25, 145.61-148.06 (d, J=245), 151.20, 156.39-156.64 (d, J=25), 159.64. MS (FAB): expected for $C_{24}H_{24}F_2N_2O_4$ (M+H)⁺ 443.46. Found 443.17813. IR (neat) $v_{max}$ 2957, 2859, 1694, 1622, 1584, 1556, 1513, 1452, 1422, 1241, 1178, 1087, 1028, 821, 790, 777, 738, 699.

Example 44

Procedure for Removing the PMB Group with CAN

CAN (0.98 g, 1.79 mmol) was added to a solution of N3-PMB-5-fluoro-1-[trans-2-fluoro-cis-3-(benzyloxymethyl)cyclobutyl]uracil (0.20 g, 0.45 mmol) in CH₃CN 5.4 mL and H₂O 1.8 mL. The reaction mixture was allowed to stir at room temperature. After 22 hr, the solvent was removed by rotary evaporator and the crude material was applied on the silica gel directly to give the desired 5-fluoro-1-[trans-2-fluoro-cis-3-(benzyloxymethyl)cyclobutyl]-uracil 67.4 mg in 47% yield.

Example 45

5-Fluoro-1-[trans-2-fluoro-cis-3-(acetoxymethyl)cyclobutyl]uracil

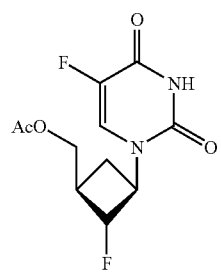

In a 25 mL flask with 5-fluoro-1-[trans-2-fluoro-cis-3-(hydroxylmethyl)cyclobutyl]-uracil (0.07 g, 0.3 mmol) and DMAP (2.3 mg, 0.02 mmol) inside, Ac₂O was added under Argon to give a yellow solution. After reacting for 6 hr, the solvents were co-evaporated with absolute EtOH and the crude product was purified by silica gel flash chromatography (CH₂Cl₂: MeOH=20:1) to give the desired oily product 65.8 mg (80%, Rf=0.36 (CH₂Cl₂: MeOH=20:1)). ¹H NMR (CDCl₃, 600 MHz): δ 1.70-1.75 (m, 1H), 2.11 (s, 3H), 2.42-2.59 (m, 2H), 4.23-4.24 (d, J=6.0, 2H), 4.56-4.63 (m, 1H), 4.97-5.08 (td, J=54.6, 6.6, 1H), 7.31-7.32 (d, J=6.0, 1H). ¹³C NMR (CDCl₃, 150 MHz): δ 20.48-20.60 (d, J=18), 21.01, 36.05-36.18 (d, J=19.5), 56.49-56.64 (d, J=22.5), 63.31, 88.55-90.06 (d, J=226.5), 125.82-126.04 (d, J=33), 140.02-141.62 (d, J=240), 149.23, 156.81, 171.06. MS (FAB): expected for $C_{11}H_{12}F_2N_2O_4$ (M+H)⁺ 275.22. Found 275.08371. IR (neat) $v_{max}$ 3072, 2918, 1708, 1466, 1378, 1243, 1074.

Example 46

4-[1,2,4]-Trizole-5-fluoro-1-[trans-2-fluoro-cis-3-(acetoxymethyl)cyclobutyl]-uracil

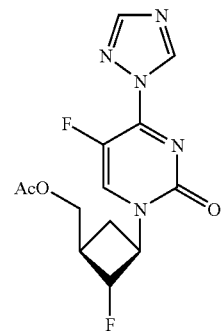

POCl₃ (0.09 mL, 0.98 mmol) was added to a solution of 1,2,4-triazole (0.22 g, 3.19 mmol) in 5 mL dry CH₃CN containing Et₃N (0.45 mL, 3.23 mmol) at 0° C. under argon. The mixture was stirred for 1 hr at room temperature and then the solid was filtered and the filtrate was mixed together with 5-fluoro-1-[trans-2-fluoro-cis-3-(acetoxymethyl)cyclobutyl]uracil (0.08 g, 0.3 mmol). After stirring at room temperature for 21 hr, the solvent was evaporated and the crude mixture was purified by silica gel flash chromatography (CH₂Cl₂ to CH₂Cl₂: MeOH=20:1) to give the desired product 0.01 g (15%, Rf=0.16 (CH₂Cl₂: MeOH=30:1)). ¹H NMR (CDCl₃, 600 MHz): δ 1.78-1.82 (m, 1H), 2.12 (s, 3H), 2.52-2.60 (m, 2H), 4.25-4.26 (d, J=6.0, 2H), 4.67-4.73 (m, 1H), 5.12-5.23 (td, J=54.6, 6.6, 1H), 8.01-8.02 (d, J=5.4, 1H), 8.16 (s, 1H), 9.17 (s, 1H). IR (neat) $v_{max}$ 3053, 2926, 2854, 1684, 1458, 1265, 738, 705.

Example 47

4-Triisopropylsiloxy-5-fluoro-1-[trans-2-fluoro-cis-3-(acetoxymethyl)cyclobutyl]uracil

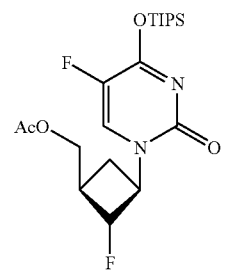

In a 25 mL flask with 5-fluoro-1-[trans-2-fluoro-cis-3-(acetoxymethyl)cyclobutyl]uracil (0.11 g, 0.40 mmol) and DMAP (0.1 g, 0.82 mmol) inside, dry CH₃CN 12 mL was added under argon, followed by the addition of Et₃N (0.1 mL, 0.82 mmol). This was cooled to 0° C. and TIPSCl (0.18 mL, 0.82 mmol) was added drop by drop. This was allowed to warm up to room temperature and left stirring for 12 hr, after which time the solvent was removed to give the crude product.

Example 48

4-tert-Butyl-diphenylsiloxy-5-fluoro-1-[trans-2-fluoro-cis-3-(acetoxymethyl)-cyclobutyl]uracil (193)

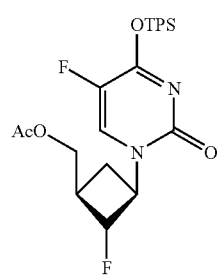

In a 25 mL flask with 5-fluoro-1-[trans-2-fluoro-cis-3-(acetoxymethyl)cyclobutyl]uracil 190 (0.08 g, 0.30 mmol) inside, dry CH$_3$CN 6 mL was added under argon, followed by the addition of Et$_3$N (0.08 mL, 0.57 mmol) and TPSCl (0.18 g, 0.59 mmol). This was allowed to stir for 14.5 hr, after which time the solvent was removed to give the crude product.

Example 49

4-[1,2,4]-Trizole-5-fluoro-1-[trans-2-fluoro-cis-3-(benzyloxymethyl)-cyclobutyl]-uracil

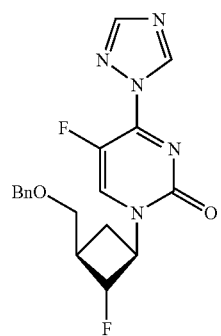

To a solution of 5-fluoro-1-[trans-2-fluoro-cis-3-(benzyloxymethyl)cyclobutyl]uracil (0.048 g, 0.15 mmol) in 1 mL pyridine, 4-chlorophenylphosphoro-dichloridate (0.12 mL, 0.74 mmol) was added at 0° C. and the mixture was stirred for 5 min at 0° C. To this mixture was added 1,2,4-triazole (0.15 g, 2.17 mmol) and this mixture was stirred at 30° C. for 24 hr. The solution was cooled to room temperature and the solvent was removed. To this residue, EtOAc and H$_2$O were added and the organic phase was separated and the aqueous phase was extracted with EtOAc once. The combined organic phase was dried over MgSO$_4$ and the solvent was evaporated to dryness. The crude reaction mixture was purified by silica gel flash chromatography (Hexane: EtOAc=1:1 to Hexane: EtOAc=1:3) to give the pure product 0.01 g (18%). $^1$H NMR (CDCl$_3$, 300 MHz): δ 1.77-1.86 (m, 1H), 2.54-2.62 (m, 2H), 3.52-3.59 (m, 1H), 3.70-3.74 (m, 1H), 4.54-4.63 (m, 2H), 4.91-5.27 (m, J=54.3, 6.6, 2H), 7.31-7.40 (m, 5H), 7.92-7.94 (d, J=6.0, 1H), 8.22 (s, 1H), 9.23 (s, 1H).

Example 50

9-[trans-2-Fluoro-cis-3-(benzyloxymethyl)cyclobutyl]adenine

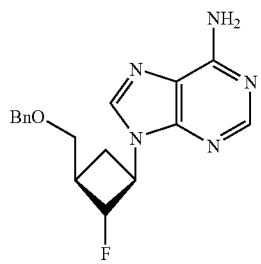

In a 25 mL three-neck flask with adenine (0.18 g, 1.33 mmol), dry K$_2$CO$_3$ (0.18 g, 1.33 mmol), 18-crown-6 (0.18 g, 0.67 mmol) and cis-2-fluoro-trans-3-(benzyloxy-methyl)cyclobutyl-mesylate (0.19 g, 0.67 mmol) inside, dry DMF 7 mL was added under argon. After addition, the mixture was heated to 120° C. for 24 hr, after which time most of the DMF was removed and the residue was purified by silica gel flash chromatography (CH$_2$Cl$_2$: MeOH=10:1) to give the N9-coupled product (0.13 g, 60.8%, Rf=0.49 (CH$_2$Cl$_2$: MeOH=10:1)) and N7-coupled product (5.26 mg, 2.4%, Rf=0.40 (CH$_2$Cl$_2$: MeOH=10:1)). $^1$H NMR (CDCl$_3$, 300 MHz): δ 2.06-2.18 (m, 2H), 2.33-2.56 (m, 3H), 3.52-3.64 (m, 2H), 4.48 (s, 2H), 4.71-4.87 (m, 1H), 5.22-5.45 (td, J=54.6, 6.6, 1H), 7.15-7.28 (m, 5H), 7.76 (s, 1H), 8.26 (s, 1H). $^{13}$C NMR (CDCl$_3$, 75 MHz): δ 20.80-21.08 (d, J=21), 37.12-37.38 (d, J=19.5), 52.71-53.02 (d, J=23.3), 68.80, 72.92, 88.97-91.98 (d, J=226), 119.61, 127.26, 127.44, 128.18, 137.81, 138.39, 149.78, 152.77, 156.08. MS (FAB): expected for C$_{17}$H$_{18}$FN$_5$O (M+H)$^+$ 328.36. Found 328.15691. IR (neat) ν$_{max}$ 3323, 3169, 2917, 2850, 1647, 1598, 1575, 1475, 1454, 1418, 1363, 1329, 1303, 1259, 1075, 798, 737, 699, 649.

Example 51

7-[trans-2-Fluoro-cis-3-(benzyloxymethyl)cyclobutyl]adenine

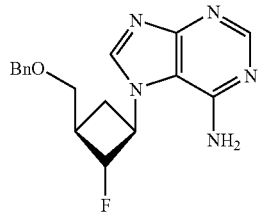

$^1$H NMR (CDCl$_3$, 400 MHz): δ 2.19-2.27 (m, 2H), 2.48-2.70 (m, 3H), 3.56-3.59 (m, 1H), 3.68-3.71 (m, 1H), 4.51-4.59 (m, 2H), 4.87-4.95 (m, 1H), 4.98-5.15 (td, J=54, 6.8, 1H), 3.73-3.74 (d, J=4.0, 2H), 7.28-7.37 (m, 5H), 7.96 (s, 1H), 8.44 (s, 1H). $^{13}$C NMR (CDCl$_3$, 100 MHz): δ 19.22-19.43 (d, J=21), 37.02-37.23 (d, J=21), 55.15-55.37 (d, J=22), 67.21, 73.57, 90.22-92.44 (d, J=222), 111.60, 127.95, 128.24, 128.75, 137.58, 143.07, 151.20, 153.49, 161.26. MS (FAB): expected for $C_{17}H_{18}FN_5O$ (M+H)$^+$ 328.36. Found 328.15679. IR (neat) $v_{max}$ 3328, 3189, 2867, 1638, 1601, 1555, 1472, 1454, 1400, 1353, 1309, 1249, 1110, 958, 840, 799, 737, 700.

Example 52

9-[trans-2-Fluoro-cis-3-(hydroxymethyl)cyclobutyl]adenine

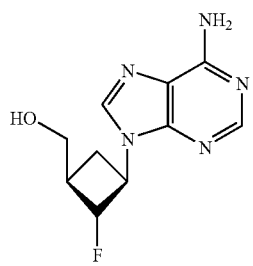

In a 25 mL flask with 1-[trans-2-fluoro-cis-3-(benzyloxymethyl)cyclobutyl]adenine (81.3 mg, 0.25 mmol) inside, dry $CH_2Cl_2$ was added under argon. This was cooled to −78° C. and $BCl_3$ (1.0 M in $CH_2Cl_2$, 0.75 mL, 0.75 mmol) was added drop by drop. After 6 hr, add ammonium in MeOH (7 N) drop by drop to quench the reaction and then evaporate the solvents. The crude material was purified by silica gel flash chromatography ($CH_2Cl_2$: MeOH=10:1 to 5:1) to give the desired product 30.8 mg in 52% yield. $^1$H NMR (CD$_3$OD, 400 MHz): δ 2.10 (m, 1H), 2.52 (m, 2H), 3.78 (m, 2H), 5.00 (m, 1H), 5.29-5.42 (td, J=54.8, 6.4, 1H), 8.25 (s, 1H), 8.29 (s, 1H). MS (FAB): expected for $C_{10}H_{12}FN_5O$ (M+H)$^+$ 237.23. Found 238.10994.

Example 53

6-Chloro-9-[trans-2-fluoro-cis-3-(benzyloxymethyl)cyclobutyl]adenine

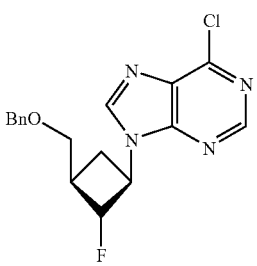

In a 25 mL three-neck flask with 6-chloropurine (0.13 g, 0.84 mmol), dry $K_2CO_3$ (0.12 g, 0.84 mmol), 18-crown-6 (0.11 g, 0.42 mmol) and cis-2-fluoro-trans-3-(benzyloxy-methyl)cyclobutyl-mesylate (0.12 g, 0.42 mmol) inside, dry DMF 7 mL was added under argon. After addition, the mixture was heated to 120° C. for 24 hr, after which time most of the DMF was removed and the residue was purified by silica gel flash chromatography ($CH_2Cl_2$: MeOH=10:1) to give 51 mg N9-coupled product in 35% yield and 14.6 mg N7-coupled product in 10% yield. $^1$H NMR (CDCl$_3$, 600 MHz): δ 1.70-1.75 (m, 1H), 2.41-2.49 (m, 1H), 2.55-2.62 (m, 1H), 3.59-3.61 (m, 1H), 3.65-3.67 (m, 1H), 4.55-4.60 (m, 2H), 5.06-5.17 (td, J=54.6, 6.6, 1H), 5.60-5.66 (m, 1H), 7.28-7.40 (m, 5H), 8.76 (s, 1H), 9.02 (s, 1H).

Example 54

6-Benzyloxy-9-[trans-2-fluoro-cis-3-(benzyloxymethyl)cyclobutyl]adenine

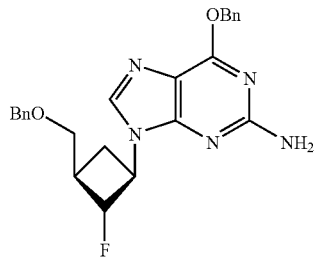

In a 100 mL three-neck flask with 2-amino-6-benzyloxypurine (0.56 g, 2.33 mmol), dry $K_2CO_3$ (0.34 g, 2.44 mmol), 18-crown-6 (0.68 g, 2.56 mmol) and cis-2-fluoro-trans-3-(benzyloxy-methyl)cyclobutyl-mesylate (0.67 g, 2.33 mmol) inside, dry DMF 25 mL was added under argon. After addition, the mixture was heated to 120° C. for 24 hr, after which time most of the DMF was removed and the residue was purified by silica gel flash chromatography ($CH_2Cl_2$: MeOH=10:1) to give 0.67 g N9-coupled product in 66% yield. $^1$H NMR (CDCl$_3$, 400 MHz): δ 2.12-2.20 (m, 1H), 2.38-2.60 (m, 2H), 3.61-3.72 (m, 2H), 4.576-4.584 (d, J=3.2, 2H), 4.68-4.77 (m, 3H), 5.28-5.45 (td, J=54.8, 6.8, 1H), 5.54 (s, 2H), 7.22-7.51 (m, 10H), 7.61 (s, 1H). $^{13}$C NMR (CDCl$_3$, 100 MHz): δ 20.98-21.19 (d, J=21), 37.44-37.64 (d, J=20), 52.91-53.13 (d, J=22), 68.19, 69.01, 73.41, 89.57-91.84 (d, J=227), 116.17, 127.81, 127.99, 128.17, 128.43, 128.58, 128.72, 136.64, 138.05, 138.30, 159.25, 161.26, 162.75. MS (FAB): expected for $C_{24}H_{24}FN_5O_2$ (M+H) 434.48. Found 434.19900. IR (neat) $v_{max}$ 3384, 2949, 2837, 1697, 1536, 1453, 1415, 1263, 1024.

Example 55

9-[trans-2-Fluoro-cis-3-(hydroxylmethyl)cyclobutyl]guanine

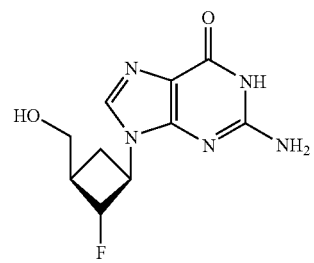

In a three-neck 100 mL flask with a stir bar, liquid ammonia about 30 mL was condensed while the flask was cooled to −78° C. Then the sodium metal was added by pieces until the dark blue color persists. In another flask with 6-benzyloxy-9-[trans-2-fluoro-cis-3-(benzyloxymethyl)cyclobutyl]adenine (0.33 g, 0.76 mmol) inside, dry THF 3 mL was added to give a light yellow colorless solution and this was added drop by drop to the above flask with sodium and ammonia. This was allowed to stir at −78° C. for 1 hr and during this time, the blue color remained. After 1 hr stirring, solid NH₄Cl was added by portions at −78° C. until the blue color disappeared to give a white emulsion. Then the dry-ice acetone bath was replaced by ice-water bath to facilitate the evaporation of the ammonia. The crude material thus obtained was directly applied to the silica gel flash chromatography (CH₂Cl₂ to CH₂Cl₂: MeOH=5:1) to give 0.1 g desired product (50%, Rf=0.26 (CH₂Cl₂: MeOH=5:1)). ¹H NMR (CD₃OD, 400 MHz): δ 2.00-2.08 (m, 1H), 2.36-2.45 (m, 2H), 3.72-3.81 (m, 2H), 4.75-4.89 (m, 1H), 5.22-5.40 (td, J=55.2, 6.4, 1H), 7.82 (s, 1H). ¹³C NMR (CD₃OD, 100 MHz): δ 21.67-21.88 (d, J=21), 40.52-40.71 (d, J=19), 54.17-54.40 (d, J=23), 90.84-93.09 (d, J=225), 118.10, 138.39, 153.48, 155.33, 159.61. MS (FAB): expected for C₁₀H₁₂FN₅O₂ (M+H)⁺ 254.23. Found 254.10489. IR (neat) ν$_{max}$ 3332, 1688, 1612, 1529, 1460, 1411, 1370, 1261, 1067.

Example 56 trans-2-Fluoro-trans-3-(benzyloxymethyl)cyclobutanol

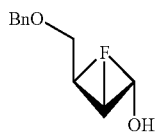

In a 100 mL flask with cis-2-fluoro-cis-3-(benzyloxymethyl)cyclobutanol (1.82 g, 9.47 mmol), 4-nitrobenzoic acid (3.16 g, 18.9 mmol) and Ph₃P (5.21 g, 19.9 mmol) inside, dry THF 25 mL was added under argon. Then the reaction mixture was cooled to 0° C. and DIAD (3.9 mL, 19.8 mmol) was added drop by drop to give a yellow solution. This was allowed to warm up to room temperature gradually and was left stirring for 77 hr, after which time the solvent was removed and applied directly to the silica gel flash chromatography (Hexane: EtOAc=20:1) to give the desired product with a little impurity and this was redissolved in 1,4-dioxane 6.6 mL. This was treated with aqueous NaOH (0.4 mol/l, 4.3 mL, 1.72 mmol) at room temperature. After 30 min, AcOH (0.07 mL, 1.22 mmol) was added and the products were concentrated to small volume under reduced pressure. The residue was partitioned between EtOAc and saturated NaHCO₃. The organic phase was dried over MgSO₄ and solvent evaporation gave the crude product that was purified by silica gel flash chromatography (Hexane: EtOAc=3:1) to give 1.04 g (52%, Rf=0.17 (Hexane: EtOAc=3:1)) desired product. ¹H NMR (CDCl₃, 600 MHz): δ 1.51-1.57 (m, 1H), 2.11-2.17 (m, 1H), 2.61-2.69 (m, 2H), 3.52-3.68 (m, 2H), 4.46-4.53 (m, 1H), 4.54 (s, 2H), 4.77-4.89 (ddd, J=54.6, 9.0, 8.4, 1H), 7.28-7.37 (m, 5H). ¹³C NMR (CDCl₃, 150 MHz): 24.74-24.88 (d, J=21), 32.46-32.59 (d, J=19.5), 68.63-68.67 (d, J=6.0), 72.21-72.35 (d, J=21), 73.43, 92.68-94.18 (d, J=225), 127.85, 128.59, 138.40.

Example 57 trans-2-Fluoro-trans-3-(benzyloxymethyl)cyclobutyl-mesylate

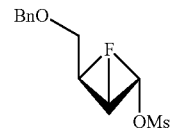

In a 50 mL flask with trans-2-fluoro-trans-3-(benzyloxymethyl)cyclobutanol (78.7 mg, 0.37 mmol) inside, dry CH₂Cl₂ was added to give a clear solution under argon. Then Et₃N (0.26 mL, 1.87 mmol) was added to the above solution. After 10 min, cool this to 0° C., MsCl (0.04 mL, 0.45 mmol) was added drop by drop and this was left stirring with the temperature going up to room temperature gradually. After 3 hr, quench the reaction by adding H₂O. Then the organic phase was separated, washed with brine once and dried over MgSO₄. Solvent evaporation gave the crude product (Rf=0.25, (Hexane: EtOAc=3:1) that was directly used in the next step. ¹H NMR (CDCl₃, 400 MHz): δ 1.85-1.93 (m, 1H), 2.30-2.40 (m, 1H), 2.71-2.79 (m, 1H), 3.01 (s, 3H), 3.56-3.65 (m, 2H), 4.50-4.58 (m, 2H), 4.99-5.16 (m, 1H), 5.17-5.27 (m, 1H), 7.25-7.36 (m, 5H). ¹³C NMR (CDCl₃, 100 MHz): δ 23.12-23.29 (d, J=17), 33.40-33.61 (d, J=21), 38.13, 66.94-66.99 (d, J=5.0), 73.48, 77.73, 88.63-90.91 (d, J=228), 127.73, 127.84, 128.57, 138.11. IR (neat) ν$_{max}$ 2937, 2865, 1719, 1454, 1359, 1175, 1110, 1012, 969, 904, 856, 805, 750, 700.

Example 58

9-[cis-2-Fluoro-cis-3-(benzyloxymethyl)cyclobutyl]adenine

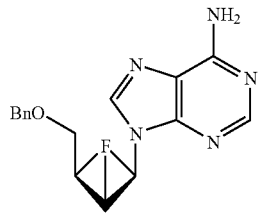

In a 25 mL three-neck flask with adenine 198 (0.11 g, 0.81 mmol), dry K₂CO₃ (0.11 g, 0.80 mmol), 18-crown-6 (0.12 g, 0.45 mmol) and trans-2-fluoro-trans-3-(benzyloxy-methyl)cyclobutyl-mesylate (0.11 g, 0.38 mmol) inside, dry DMF 5 mL was added under argon. After addition, the mixture was heated to 120° C. for 24 hr, after which time most of the DMF was removed and the residue was purified by silica gel flash chromatography (CH₂Cl₂: MeOH=10:1) to give 0.02 g N9-coupled product (20%, Rf=0.21 (CH$_2$Cl$_2$: MeOH=10:1)). IR (neat) $v_{max}$ 2924, 2851, 1644, 1600, 1473, 1265, 1087, 737, 701.

Example 59 cis-2-Fluoro-3-(tert-butyl-diphenyl-siloxymethyl) cyclobutanone

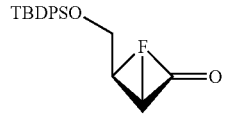

In a 25 mL flask with cis-2-fluoro-3-(hydroxylmethyl)-cyclobutanone (0.23 g, 1.9 mmol) inside, dry CH$_2$Cl$_2$ 10 mL was added, followed by the addition of imidazole (0.2 g, 2.94 mmol). Then TBDPSCl (0.61 mL, 2.34 mmol) was added dropwisely. After reacting for 5.5 hr, the reaction mixture was diluted with 20 mL CH$_2$Cl$_2$, which was washed with 10 mL H$_2$O twice, 10 mL saturated NaHCO$_3$ once and 10 mL brine once. The organic phase was dried over MgSO$_4$ and solvent evaporation gave the crude product, which was purified by silica gel flash chromatography (Hexane: EtOAc=9:1) to give 0.61 g (88%, Rf=0.32 (Hexane: EtOAc=9:1)) the desired product. IR (neat) $v_{max}$ 2931, 2858, 1798, 1634, 1567, 1472, 1428, 1113, 741, 702.

Example 60

Benzyl-(3-tert-butyl-diphenyl-siloxymethyl-2-fluoro-cyclobutyl)-amine

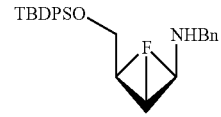

In a 50 mL flask with cis-2-fluoro-3-(tert-butyl-diphenyl-siloxymethyl)cyclobutanone (0.35 g, 0.98 mmol) inside, dry 1,2-DCE 3.4 mL was added under Argon to give a colorless solution. To this, benzylamine (0.13 mL, 1.19 mmol) was added to give still a colorless solution. After stirring for 5 min, sodium triacetoxyborohydride (0.29 g, 1.37 mmol) was added all at once to give a white emulsion. After another 30 min, AcOH (0.06 mL, 1.05 mmol) was added drop by drop. After 5 min, it gave a yellow solution and this was left stirring for 2 hr and then the reaction was quenched by sat. NaHCO$_3$. The organic phase was separated and the aqueous phase was extracted with CH$_2$Cl$_2$ twice. The combined organic phase was dried over MgSO$_4$ and the crude product was purified by silica gel flash chromatography (Hexane: EtOAc=9:1) to give 0.27 g (61%, Rf=0.22 (Hexane: EtOAc=9:1)) the desired product. $^1$H NMR (CDCl$_3$, 400 MHz): δ 1.0 (s, 9H), 1.59-1.68 (m, 1H), 2.23-2.46 (m, 2H), 3.19-3.30 (m, 1H), 3.6-3.87 (m, 4H), 5.14-5.32 (m, 1H), 7.3-7.7 (m, 15H).

Example 61

3-tert-Butyl-diphenyl-siloxymethyl-2-fluoro-cyclobutylamine

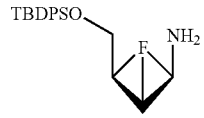

The benzyl-(3-tert-butyl-diphenyl-siloxymethyl-2-fluoro-cyclobutyl)-amine 212 (0.27 g, 0.6 mmol) was dissolved in 6 mL MeOH and this was treated with 10% Pd/C 0.13 g. This was subjected to the hydrogenolysis conditions (50 psi). After 12 hr, the reaction mixture was filtered through celite and the filtrated was concentrated and was purified by silica gel flash chromatography (Hexane: EtOAc=3:1) to give 0.16 g (68%, Rf=0.30 (CH$_2$Cl$_2$: MeOH=15:1)) the desired product. $^1$H NMR (CDCl$_3$, 400 MHz): δ 1.0 (s, 9H), 1.58-1.68 (m, 1H), 2.24-2.34 (m, 1H), 2.37-2.53 (m, 1H), 3.30-3.44 (m, 1H), 3.60-3.65 (m, 1H), 3.81-3.85 (m, 1H), 4.98-5.15 (m, 1H), 7.38-7.70 (m, 10H). $^{13}$C NMR (CDCl$_3$, 100 MHz): δ 20.16, 27.43, 33.37, 37.85-38.05 (d, J=20), 63.02-63.13 (d, J=11), 94.17-96.14 (d, J=197), 128.91, 131.00, 135.01, 136.81. MS (FAB): expected for C$_{21}$H$_{28}$FNOSi (M+H)$^+$ 358.54. Found 358.19963.

Example 62

1-Benzyl-3-(3-tert-butyl-diphenyl-siloxymethyl-2-fluoro-cyclobutyl)-urea

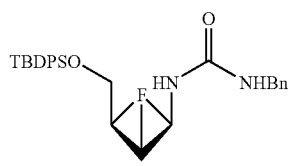

In a 25 mL flask with benzyl-(3-benzyloxymethyl-2-fluoro-cyclobutyl)-amine (0.16 g, 0.45 mmol) inside, dry CH$_2$Cl$_2$ 15 mL was added under argon at room temperature to give a colorless solution, followed by the addition of Et$_3$N (0.06 mL, 0.43 mmol). After stirring for 10 min, 4-nitrophenyl-N-benzylcarbamate 150 (0.11 g, 0.42 mmol) was added all at once to give a yellow solution. This was left stirring at room temperature for 28 hr and the reaction was quenched by adding 20 mL CH$_2$Cl$_2$. The organic phase was washed with 1 M NaOH 10 mL, H$_2$O 10 mL and brine 10 mL and was dried over MgSO$_4$. Solvent evaporation gave the crude product that is purified by silica gel flash chromatography (Hexane: EtOAc=3:1) to give 0.2 g (90%, Rf=0.62 (Hexane: EtOAc=1:

1)) the desired product as a white solid. IR (neat) $\nu_{max}$ 3337, 2930, 2857, 1632, 1571, 1428, 1263, 1112, 740, 702.

Example 63

3-(3-tert-butyl-diphenyl-siloxymethyl-2-fluoro-cyclobutyl)-urea

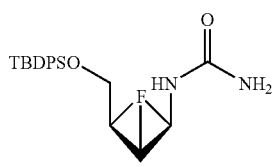

In the Parr Hydrogenator flask with 1 mL AcOH and 10% Pd/C 0.15 g inside, 1-benzyl-3-(3-tert-butyl-diphenyl-siloxymethyl-2-fluoro-cyclobutyl)-urea in 5 mL AcOH was added. This was hydrogenolysed at 50 psi for 4 d, after which the crude mixture was filtered through celite and was purified by silica gel flash chromatography ($CH_2Cl_2$: MeOH=40:1) to give 0.15 g (63.3%, Rf=0.44 ($CH_2Cl_2$: MeOH=20:1) the desired product. IR (neat) $\nu_{max}$ 3425, 3339, 2931, 2858, 1656, 1608, 1560, 1111, 701.

Example 64

1-[cis-2-fluoro-cis-3-(tert-butyl-diphenyl-siloxymethyl)cyclobutyl]cytosine

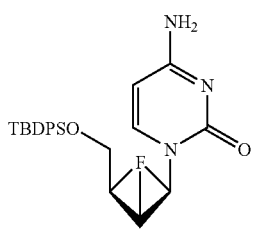

In a three-neck 25 mL flask with dry EtOH 0.6 mL inside, Na (18 mg, 0.78 mmol) was added. $H_2$ gas was produced immediately. When all the $H_2$ evolution finished, an EtOH solution of 3-(3-tert-butyl-diphenyl-siloxymethyl-2-fluoro-cyclobutyl)-urea (0.15 g, 0.38 mmol) was added to give a kind of green solution. Then ethoxyacrylonitrile 114 (0.04 mL, 0.39 mmol) was added and this left stirring at room temperature. After 42 hr, the reaction mixture was concentrated under reduced pressure and was directly applied to the silica gel flash chromatography to give 1-[cis-2-fluoro-cis-3-(tert-butyl-diphenyl-siloxymethyl)cyclobutyl]cytosine 16.9 mg (10%, Rf=0.41 ($CH_2Cl_2$: MeOH=10:1)) and 3-[cis-2-fluoro-cis-3-(tert-butyl-diphenyl-siloxymethyl)cyclobutyl]cytosine 16.9 mg (10%, Rf=0.30 ($CH_2Cl_2$: MeOH=10:1)).

Example 65 cis-3-(Benzyloxymethyl)cyclobutyl-tosylate

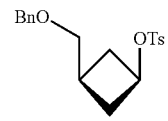

In a 250 mL flask with cis-3-(benzyloxymethyl)cyclobutanol (9.14 g, 47.5 mmol), DMAP (0.58 g, 4.75 mmol) and TsCl (10.88 g, 57 mmol) inside, dry $Et_3N$ (16.6 mL, 118.8 mmol) was added at 0° C. under argon. After addition, remove the ice-water bath and let the reaction stir at room temperature for 3 hr, after which time $CH_2Cl_2$ and $H_2O$ were added. The organic phase was separated, washed with $H_2O$ once and brine once, dried over $MgSO_4$ and concentrated to dryness. The crude product thus obtained was purified by silica gel flash chromatography (Hexane: EtOAc=3:1) to give a light yellow oil 13.2 g (80%, Rf=0.36 (Hexane: EtOAc=3:1)). $^1$H NMR ($CDCl_3$, 400 MHz): δ 1.91-1.99 (m, 2H), 2.05-2.10 (m, 1H), 2.28-2.36 (m, 2H), 2.44 (s, 3H), 3.37-3.38 (d, J=6.0, 2H), 4.46 (s, 2H), 4.66-4.74 (m, 1H), 7.27-7.36 (m, 7H), 7.76-7.78 (d, J=8.4, 2H). $^{13}$C NMR ($CDCl_3$, 75 MHz): δ 26.83, 34.13, 71.52, 73.17, 73.69, 76.81, 77.22, 77.65, 127.67, 127.75, 127.93, 128.51, 129.90, 134.10, 138.32, 144.78. MS (FAB): expected for $C_{19}H_{22}O_4S$ $(M-H)^+$ 345.44. Found 345.11585. IR (neat) $\nu_{max}$ 3052, 2926, 1366, 1265, 1189, 1177, 1010, 921, 855, 815, 739, 704.

Example 66-3-Benzyloxymethyl-1-cyclobutene

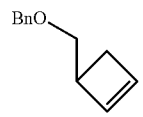

In a 250 mL flask with t-BuOK (11.95 g, 0.11 mol) inside, dry DMSO 50 mL was added under argon to give a colorless solution. Then at room temperature, cis-3-(benzyloxymethyl) cyclobutyl-tosylate (12.3 g, 35.5 mmol) was added very slowly to the previous flask. The reaction mixture was left stirring at room temperature for 4 hr, after which time quench the reaction by adding $H_2O$ 200 mL slowly, followed by the addition of 100 mL $Et_2O$. The separated water phase was re-extracted with $Et_2O$ three times and the combined organic phase was washed with $H_2O$ four times. The organic phase was dried over $MgSO_4$ and concentrated to dryness to give a light yellow oil which was purified by silica gel flash chromatography (Hexane: EtOAc=9:1) to give 4.45 g (71.9%, Rf=0.59 ((Hexane: EtOAc=9:1)) the desired product. $^1$H NMR ($CDCl_3$, 600 MHz): δ 2.19-2.21 (d, J=12, 1H), 2.66-2.69 (dd, J=13.2, 4.2, 1H), 3.11-3.14 (m, 1H), 3.50-3.56 (m, 2H), 4.54 (s, 2H), 6.09-6.11 (m, 2H), 7.27-7.35 (m, 5H). $^{13}$C NMR ($CDCl_3$, 150 MHz): δ 34.40, 43.72, 73.32, 74.07,

Example 67

Exo-2-benzyloxy-5-oxabicyclo[2.1.0]pentane

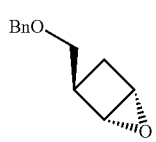

Under argon, to a mixture of PhCN (0.8 mL, 7.89 mmol) and KHCO$_3$ (0.17 g, 1.7 mmol) in 12 mL MeOH was added a solution of 3-benzyloxymethyl-1-cyclobutene (0.52 g, 3 mmol) in 12 mL CHCl$_3$, followed by the addition of 1 mL of 30% H$_2$O$_2$. This was left stirring at room temperature vigorously. After 4 d, the reaction mixture was poured into 75 mL 5% sodium thiosulfate and the aqueous phase was re-extracted with 200 mL Et$_2$O. The organic phase was washed with 200 mL H$_2$O, 200 mL saturated NaHCO$_3$ and 200 mL brine. The ether extract was dried over MgSO$_4$ and solvent evaporation gave the crude product (trans:cis=4.8:1) which was purified by silica gel flash chromatography (Hexane only to Hexane: EtOAc=10:1) to give trans-diastereomer as a colorless oil (0.22 g, 38%) and cis-diastereomer 0.22 g (37%). $^1$H NMR (CDCl$_3$, 400 MHz): δ 1.65-1.70 (m, 1H), 1.89-1.94 (m, 1H), 2.37-2.43 (m, 1H), 3.51-3.56 (m, 1H), 3.64-3.67 (m, 1H), 3.82-3.83 (m, 1H), 3.88-3.89 (t, J=2.8, 1H), 4.51-4.58 (m, 2H), 7.28-7.38 (m, 5H). $^{13}$C NMR (CDCl$_3$, 75 MHz): δ 32.25, 41.61, 54.45, 57.41, 70.69, 73.41, 127.79, 127.84, 128.52, 138.28. IR (neat) ν$_{max}$ 3062, 3030, 2980, 2938, 2854, 2795, 1496, 1454, 1364, 1332, 1205, 1109, 1091, 1028, 957, 846, 823, 738, 698.

Example 68

Endo-2-benzyloxy-5-oxa-bicyclo [2.1.0]pentane

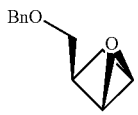

$^1$H NMR (CDCl$_3$, 600 MHz): δ 1.45-1.48 (m, 1H), 2.18-2.21 (m, 1H), 2.68-2.73 (m, 1H), 3.28-3.31 (m, 1H), 3.59-3.62 (t, J=9.0, 1H), 3.82 (s, 1H), 3.88 (s, 1H), 4.47-4.55 (m, 2H), 7.27-7.36 (m, 5H). $^{13}$C NMR (CDCl$_3$, 150 MHz): δ 30.78, 40.08, 52.39, 54.80, 69.72, 73.39, 127.81, 127.89, 128.58, 138.58. IR (neat) ν$_{max}$ 3062, 3030, 2982, 2938, 2855, 2796, 1496, 1454, 1365, 1333, 1256, 1206, 1185, 1160, 1091, 1028, 956, 915, 846, 824, 738, 698.

Example 69

3-Benzyloxymethyl-cyclobutane-1,2-diol

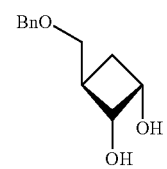

In a 10 mL flask with 3-benzyloxymethyl-1-cyclobutene (0.1 g, 0.57 mmol) inside, 0.72 mL tBuOMe, 1.54 mL tBuOH and 0.54 mL H$_2$O were added to give two layers. Then NMO (50% wt sol. in H$_2$O, 0.36 mL, 1.71 mmol) and OSO$_4$ (0.07 mL, 0.06 mmol) were added drop by drop successively to give a light brown solution. This was left stirring at room temperature. After 3 hr, the solution was diluted with H$_2$O and extracted with EtOAc three times. The organic layer was washed with brine once, dried over MgSO$_4$ and concentrated. The crude product was purified by silica gel flash chromatography (Hexane: EtOAc=3:1 to Hexane: EtOAc=1:1) to give 27.4 mg (23%) the desired product. $^1$H NMR (CDCl$_3$, 300 MHz): δ 1.70-1.92 (m, 2H), 2.46-2.75 (m, 1H), 3.02-3.2 (m, 1H), 3.2-3.34 (m, 1H), 3.4-3.6 (m, 2H), 3.90-4.10 (m, 1H), 4.2-4.4 (m, 1H), 4.4-4.6 (s, 2H), 7.21-7.50 (m, 5H). $^{13}$C NMR (CDCl$_3$, 100 MHz): δ 28.08, 43.45, 68.32, 70.19, 71.41, 73.28, 127.83, 128.61, 138.56. IR (neat) ν$_{max}$ 3376, 2937, 2856, 1453, 1098, 738, 698.

Example 70

(2,3-Diiodo-cyclobutylmethoxymethyl)benzene

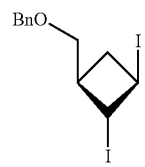

In a three-neck 25 mL flask with 12 (0.29 g, 1.14 mmol) inside, dry CH$_2$Cl$_2$ 2 mL was added under argon to give a dark brown solution. After stirring for 5 min, 3-benzyloxymethyl-1-cyclobutene (0.20 g, 1.14 mmol) in 8 mL CH$_2$Cl$_2$ was added drop by drop. After stirring for 10 min, silylated 5-fluorocytosine (0.39 g, 1.43 mmol) was added all at once. This was left stirring for 25 hr and the reaction was quenched by diluting it firstly with CH$_2$Cl$_2$, followed by the addition of sodium thiosulfate. The organic phase was separated, washed with H$_2$O once, dried over MgSO$_4$ and concentrated. The crude product was purified by silica gel flash chromatography (Hexane: EtOAc=20:1) to give 2,3-diiodo-cyclobutyl-methoxymethyl)benzene 0.15 g (30%, Rf=0.54 (Hexane: EtOAc=10:1)).

Example 71

1-[trans-2-Hydroxyl-cis-3-(benzyloxymethyl)cyclobutyl]adenine

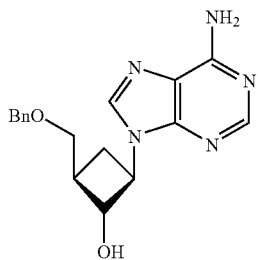

In a 25 mL three-neck flask with adenine (0.23 g, 1.68 mmol), dry NaH (0.04 g, 1.68 mmol), 18-crown-6 (0.45 g, 1.68 mmol) inside, a dry DMF solution of 2-benzyloxy-5-oxabicyclo[2.1.0]pentane (0.16 g, 0.84 mmol) was added under argon. After stirring at ambient temperature for 10 min, began to heat to 50° C. for 12 hr and then 120° C. for 12 hr, after which time the reaction was left to stir for overnight at ambient temperature. $H_2O$ and EtOAc were added The organic phase was dried over $MgSO_4$ and solvent evaporation gave the crude product, which was purified by silica gel flash chromatography ($CH_2Cl_2$: MeOH=20:1) to give the desired product 0.15 g (50%, Rf=0.68 ($CH_2Cl_2$: MeOH=5:1)). $^1$H NMR ($CDCl_3$, 600 MHz): δ 1.92-1.97 (m, 1H), 2.42-2.54 (m, 2H), 3.60-3.65 (m, 2H), 4.31-4.34 (t, J=7.2, 1H), 4.38-4.42 (m, 1H), 4.52-4.56 (m, 2H), 4.93 (bs, 1H), 6.01 (bs, 2H), 7.27-7.35 (m, 5H), 7.73 (s, 1H), 8.28 (s, 1H). $^{13}$C NMR ($CDCl_3$, 150 MHz): δ 21.71, 38.78, 55.37, 69.98, 70.82, 73.41, 119.60, 127.86, 127.92, 128.64, 138.29, 138.53, 150.14, 152.97, 155.72. MS (FAB): expected for $C_{17}H_{19}N_5O_2$ (M+H) 326.37. Found 326.16116. IR (neat) $ν_{max}$ 3358, 2921, 2850, 1734, 1646, 1601, 1455, 1373, 1239, 1101, 1024, 834, 745, 699, 647.

Example 72

1-[trans-2-Hydroxyl-cis-3-(hydroxymethyl)cyclobutyl]adenine

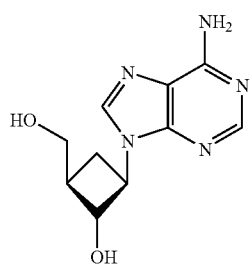

In a 25 mL flask with 1-[trans-2-hydroxyl-cis-3-(benzyloxymethyl)cyclobutyl] adenine (37.2 mg, 0.11 mmol) inside, dry $CH_2Cl_2$ 5 mL was added to give a white emulsion under argon. This was cooled to −78° C. and after 10 min, $BCl_3$ (1.0M in $CH_2Cl_2$, 0.33 mL, 0.33 mmol) was added drop by drop. This was allowed to stir at no higher than 0° C. and after 6 hr, the reaction mixture was quenched by adding 7N $NH_3$ in MeOH (0.4 mL, 2.75 mmol) drop by drop. The products were concentrated under reduced pressure and was purified by silica gel flash chromatography ($CH_2Cl_2$ to $CH_2Cl_2$: MeOH=5:1) and reverse phase preparative HPLC ($H_2O$ and $CH_3CN$ gradient) to give the desired product 13 mg (50%, Rf=0.11 ($CH_2Cl_2$: MeOH=5:1)).

Example 73

Procedure for the DAST Reaction with 1-[trans-2-hydroxyl-cis-3-(benzyloxymethyl)-cyclobutyl]adenine In a 5 mL flask with 1-[trans-2-hydroxyl-cis-3-(benzyloxymethyl)cyclobutyl] adenine (10 mg, 0.03 mmol) inside, dry $CH_2Cl_2$ was added under argon. After 5 min, DAST (0.02 mL, 0.15 mmol) was added and was left stirring at room temperature. After 1.5 hr, the solvent was removed and the crude product was purified by silica gel flash chromatography ($CH_2Cl_2$: MeOH=60:1 to $CH_2Cl_2$: MeOH=20:1) to give the desired compound 7.4 mg (73.6%, Rf=0.36 ($CH_2Cl_2$: MeOH=20:1)).

Example 74

5-Fluoro-2-[trans-2-hydroxyl-cis-3-(benzyloxymethyl)-cyclobutyl]cytosine

In a 25 mL flask with exo-2-benzyloxy-5-oxabicyclo[2.1.0]pentane (0.1 g, 0.53 mmol), 5-fluorocytosine (0.14 g, 1.08 mmol), $K_2CO_3$ (73 mg, 0.53 mmol) and 18-crown-6 (0.1 g, 0.38 mmol) inside, dry DMF 10 mL was added under argon to give an emulsion. The solution was heated at 120° C. for 24 hr. DMF was removed and the crude material was purified by silica gel flash chromatography ($CH_2Cl_2$: MeOH=20:1) to give a white solid (0.02 g, 12%). MS (FAB): expected for $C_{16}H_{18}FN_3O_3$ (M+H)$^+$ 320.33. Found 320.14064. IR (neat) $ν_{max}$ 3333, 3218, 2879, 1636, 1498, 1415, 1352, 1288, 1207, 1112, 1038, 958, 781, 736, 699. The absolute stereochemistry was established by X-ray crystallography analyses.

Example 75

N3-PMB-5-Fluoro-1-[trans-2-hydroxyl-cis-3-(benzyloxymethyl)cyclobutyl]-uracil

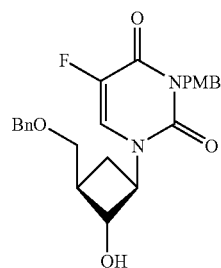

In a 25 mL three-neck flask with N3-PMB-5-fluoro-uracil (0.17 g, 0.68 mmol), dry K$_2$CO$_3$ (0.09 g, 0.68 mmol), 18-crown-6 (0.18 g, 0.68 mmol) and 2-benzyloxy-5-oxabicyclo[2.1.0]pentane (0.12 g, 0.62 mmol, trans/cis=1/1) inside, dry DMF 6 mL was added under argon. After addition, the mixture was heated to 120° C., after 2 d, DMF was removed and the crude material was purified by silica gel flash chromatography (CH$_2$Cl$_2$ to CH$_2$Cl$_2$: MeOH=80:1 to CH$_2$Cl$_2$: MeOH=60:1) to give an oil (0.14 g, 52.6%, Rf=0.41 (CH$_2$Cl$_2$: MeOH=20:1)). $^1$H NMR (CDCl$_3$, 600 MHz): δ 0.87-0.89 (m, 1H), 1.07-1.10 (m, 1H), 1.32-1.35 (m, 1H), 3.40-3.51 (m, 2H), 3.78 (s, 3H), 4.52 (s, 2H), 5.01-5.11 (m, 1H), 6.82-6.84 (dd, 2H), 7.27-7.38 (m, 5H), 7.45-7.47 (dd, 2H). MS (FAB): expected for C$_{24}$H$_{25}$FN$_2$O$_5$ (M+Li)$^+$ 447.46. Found 447.4. IR (neat) $v_{max}$ 3400, 2917, 2849, 1712, 1680, 1651, 1513, 1455, 1248, 1177, 1109, 1029, 773, 737, 701.

Example 76

5-Fluoro-1-[trans-2-hydroxyl-cis-3-(hydroxymethyl)cyclobutyl]uracil

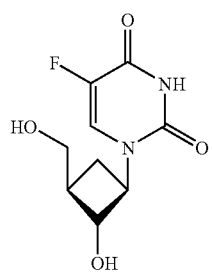

In a 10 mL flask with AlCl$_3$ (0.19 g, 1.43 mmol) inside, dry anisole 1 mL was added under argon to give a light yellow solution. In another flask with N3-PMB-5-fluoro-1-[trans-2-hydroxyl-cis-3-(benzyloxymethyl)cyclobutyl]uracil (64 mg, 0.14 mmol) inside, dry anisole 1 mL was added, after which AlCl$_3$ solution was added to it slowly at room temperature by syringe pump. After 1 hr, cooled the mixture to 0° C., dry MeOH was added slowly to give a colorless solution at the end. Then the solvents were removed and the product was purified by silica gel flash chromatography (CH$_2$Cl$_2$: MeOH=20:1) to give a white solid 32.2 mg (30%, Rf=0.21, (CH$_2$Cl$_2$: MeOH=20:1)).

Example 77

1-Methylene-3-benzyloxymethyl-cyclobutane

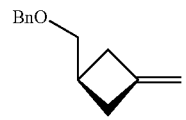

In a 50 mL three-neck flask with t-BuOK (0.54 g, 4.8 mmol) and methyltriphenylphosphonium bromide (1.72 g, 4.8 mmol) inside, dry 1,4-dioxane was added under argon to give a yellow emulsion. This was heated to 40° C. for 30 min, after which time the mixture was cooled to 10° C. and a 1,4-dioxane solution of 3-(benzyloxymethyl)cyclobutanone (0.76 g, 4 mmol) was added drop by drop. The mixture was left stirring at 10° C. for 3 hr. Then the solvent was removed by rotary evaporator and the residue was dissolved in Et$_2$O and H$_2$O. The organic phase was separated and the aqueous phase was extracted with Et$_2$O. The combined organic phase was dried over MgSO$_4$ and the solvent was evaporated to dryness to give an oily product, which was purified by silica gel flash chromatography (Hexane: EtOAc=20:1) to give a colorless oil (0.48 g, 63%, Rf=0.79 (Hexane: EtOAc=3:1)). $^1$H NMR (CDCl$_3$, 400 MHz): δ 2.36-2.48 (m, 2H), 2.52-2.64 (m, 1H), 2.72-2.84 (m, 2H), 3.48-3.50 (d, J=7.2, 2H), 4.53 (s, 1H), 4.74-4.77 (m, 2H), 7.2-7.4 (m, 5H). $^{13}$C NMR (CDCl$_3$, 100 MHz): δ 29.82, 35.06, 73.26, 74.60, 106.52, 127.77, 127.88, 128.60, 147.34. MS (FAB): expected for C$_{13}$H$_{16}$O (M+H)$^+$ 189.27. Found 189.12748. IR (neat) $v_{max}$ 2921, 2853, 1720, 1676, 1453, 1272, 1113, 1071, 1027, 875, 737, 713, 698.

Example 78

1-Hydroxymethyl-3-benzyloxymethyl-cyclobutane

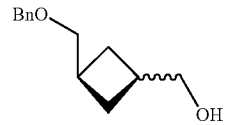

In a 10 mL flask with 1-methylene-3-benzyloxymethyl-cyclobutane (1.54 g, 8.19 mmol) inside, dry THF 11 mL was added under argon to give a colorless solution. Then cool this to 0° C., 9-BBN (0.5 M in THF, 27.4 mL, 13.7 mmol) was added drop by drop. This was allowed to warm up to ambient temperature and was left stirring for 22 hr, after which time the reaction mixture was cooled to 0° C. and H$_2$O (0.9 mL), 3 N NaOH (2.7 mL) and 30% H$_2$O$_2$ (2.8 mL) were added successively. After stirring for 1 hr, 2 N HCl and saturated NH$_4$Cl were added. The mixture was extracted with EtOAc and the separated organic phase was dried over MgSO$_4$ and solvent evaporation gave the crude oily product, which was purified by silica gel flash chromatography (Hexane: EtOAc=3:1) to give a colorless oil (cis/trans=2l1, 1.44 g, 85%, Rf=0.16 (Hexane: EtOAc=3:1)). $^1$H NMR (CDCl$_3$, 400

MHz): δ 1.52-1.60 (m), 1.86-1.90 (m), 2.12-2.19 (m), 2.36-2.64 (m), 3.39-3.41 (d, J=8), 3.49-3.51 (d, J=8), 3.54-3.56 (d, J=8), 3.64-3.66 (d, J=8), 4.51 (s), 4.53 (s), 7.2-7.4 (m). MS (FAB): expected for $C_{13}H_{18}O_2$ (M+H)$^+$ 207.28. Found 207.13807.

Example 79 cis-3-Benzyloxymethyl-cyclobutanecarbaldehyde

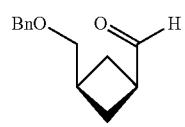

In a 25 mL flask, a solution of dry DMSO (0.2 mL, 2.76 mmol) in 7 mL dry $CH_2Cl_2$ was cooled to −78° C., after which oxalyl chloride (0.12 mL, 1.37 mmol) was added drop by drop under argon. After stirring at −78° C. for 30 min, a $CH_2Cl_2$ solution of 1-hydroxymethyl-3-benzyloxymethyl-cyclobutane (cis/trans=2:1, 0.2 g, 0.97 mmol) was added drop by drop. After stirring for 1 hr, Et$_3$N (0.7 mL, 4.9 mmol) was added dropwisely. After 15 min, the reaction was warmed to ambient temperature. After 4 hr, TLC showed no starting material. Then the reaction mixture was diluted with 30 mL $CH_2Cl_2$, washed with 30% aqueous NH$_4$Cl (2×10 mL), H$_2$O (1×10 mL) and brine (1×10 mL). The organic phase was dried over MgSO$_4$ and the solvents were removed to give an oily product, which was purified by silica gel chromatography ((Hexane: EtOAc=9:1) to give the cis-diastereomer (74 mg, 37.4%, Rf=0.43 (Hexane: EtOAc=12:1)) as a colorless oil. $^1$H NMR (CDCl$_3$, 400 MHz): δ 2.01-2.08 (m, 2H), 2.21-2.28 (m, 2H), 2.58-2.70 (m, 1H), 3.03-3.12 (m, 1H), 3.37-3.39 (d, J=8.0, 2H), 4.49 (s, 2H), 7.25-7.36 (m, 5H), 9.66-9.67 (d, J=4.0, 1H). MS (FAB): expected for $C_{13}H_{16}O_2$ (M−H)$^+$ 203.26. Found 203.10658. IR (neat) $v_{max}$ 3054, 2935, 2858, 1704, 1454, 1266, 1092, 738, 704.

Example 80 trans-3-Benzyloxymethyl-cyclobutanecarbaldehyde

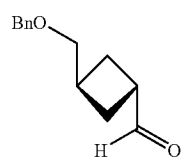

$^1$H NMR (CDCl$_3$, 400 MHz): δ 1.9-2.1 (m, 2H), 2.3-2.4 (m, 2H), 2.5-2.61 (m, 1H), 3.0-3.2 (m, 1H), 3.42-3.44 (d, J=8.0, 2H), 4.5 (s, 2H), 7.2-7.4 (m, 5H), 9.77-9.78 (d, J=4.0, 1H). IR (neat) $v_{max}$ 2917, 2849, 1704, 1456, 1265, 1094, 738, 701.

Example 81 cis-1-Hydroxymethyl-3-benzyloxymethyl-cyclobutane

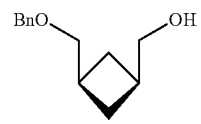

In a 50 mL flask with cis-3-benzyloxymethyl-cyclobutanecarbaldehyde (73 mg, 0.36 mmol) inside, dry $CH_2Cl_2$ 7 mL was added under argon to give a colorless solution. Then this was cooled to −78° C., DIBAL-H (1.0 M in hexane, 0.7 mL, 0.72 mmol) was added drop by drop. This was left stirring at −78° C. and after 3 hr, the reaction was quenched with dry MeOH 0.2 mL. The reaction mixture was allowed to warm up to RT gradually. After 1.5 hr, 2 mL Rochelle salt was added and the mixture was stirred vigorously for overnight. Then the organic phase was separated and washed with brine, dried over MgSO$_4$ and concentrated. Purification by silica gel flash chromatography (Hexane: EtOAc=3:1) yielded cis-1-hydroxymethyl-3-benzyloxymethyl-cyclobutane as a colorless oil (54 mg, 73.4%, Rf=0.17 (Hexane: EtOAc=3:1)). $^1$H NMR (CDCl$_3$, 300 MHz): δ 1.48-1.61 (m, 2H), 2.10-2.20 (m, 2H), 2.40-2.55 (m, 2H), 3.39-3.41 (d, J=8.0, 2H), 3.54-3.56 (d, J=8.0, 2H), 4.51 (s, 2H), 7.20-7.40 (m, 5H).

Example 82-cis-1-Hydroxylmethyl-3-(benzyloxymethyl)cyclobutyl-mesylate

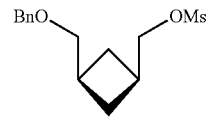

In a 25 mL flask with cis-1-hydroxymethyl-3-benzyloxymethyl-cyclobutane (43.9 mg, 0.21 mmol) inside, 5 mL dry $CH_2Cl_2$ was added under argon, followed by the addition of Et$_3$N (0.15 mL, 1.06 mmol). After 5 min, the reaction mixture was cooled to 0° C. and MsCl (0.02 mL, 0.25 mmol) was added drop by drop. After reacting for 1 hr at 0° C., the reaction was quenched by adding H$_2$O and the organic phase was separated, washed with brine once, dried over MgSO$_4$ and concentrated to give a light yellow crude product. Purification by silica gel flash chromatography (Hexane: EtOAc=3:1) gave the desired product as a colorless oil (48.1 mg, 80%, Rf=0.26 (Hexane: EtOAc=3:1)). $^1$H NMR (CDCl$_3$, 400 MHz): δ 1.59-1.69 (m, 2H), 2.15-2.24 (m, 2H), 2.46-2.76 (m, 2H), 2.95 (s, 3H), 3.38-3.40 (d, J=8.0, 2H), 4.12-4.14 (d, J=8.0, 2H), 4.50 (s, 2H), 7.20-7.40 (m, 5H). MS (FAB):

expected for $C_{14}H_{20}O_4S$ (M−H) 283.37. Found 283.09982. IR (neat) $v_{max}$ 3055, 2937, 2859, 1357, 1266, 1175, 1097, 972, 950, 738, 703.

Example 83

N3—PMB-5-Fluoro-1-[cis-4-(benzyloxymethyl) cyclobutyl]uracil

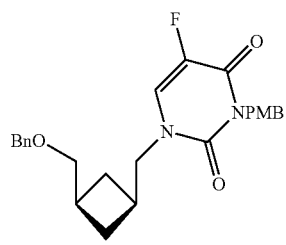

In a 50 mL three-neck flask with cis-1-hydroxylmethyl-3-(benzyloxymethyl)-cyclobutyl-mesylate (0.51 g, 1.79 mmol), N3-PMB-5-fluoro-uracil (0.49 g, 1.97 mmol) and $Cs_2CO_3$ (0.64 g, 1.97 mmol) inside, dry DMF 10 mL was added under argon to give a light yellow solution with some white solids at the bottom of the flask. After 5 min, start to heat to 80° C. After 24 hr, add 30 mL EtOAc and 20 mL $H_2O$. The organic phase was separated and washed with brine once. The organic phase was dried over $MgSO_4$ and the solvents were evaporated to give the crude product, which was purified by silica gel flash chromatography (Hexane: EtOAc=3:1) to give an off-white solid (0.66 g, 84%). MS (FAB): expected for $C_{25}H_{27}FN_2O_4$ $(M+H)^+$ 439.49. Found 439.20310. IR (neat) $v_{max}$ 3073, 2933, 2856, 1713, 1655, 1513, 1467, 1249, 1178, 1106, 1032, 993, 820, 773, 742, 699.

Example 84

5-Fluoro-1-[cis-4-(hydroxymethyl)-cyclobutyl]uracil

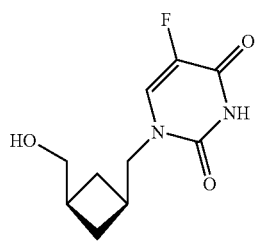

In a 25 mL flask with $AlCl_3$ (1.93 g, 14.4 mmol) inside, dry anisole 5 mL was added under argon to give a light yellow solution. In another flask with N3-PMB-5-fluoro-1-[cis-4-(benzyloxymethyl)cyclobutyl]uracil (0.66 g, 1.44 mmol) inside, dry anisole 5 mL was added, after which time $AlCl_3$ solution was added to it ver slowly at room temperature. After addition finishes, the mixture was cooled to 0° C. and dry MeOH was added slowly to give a colorless solution at the end. Then the solvents were removed and the product was purified by silica gel flash chromatography ($CH_2Cl_2$: MeOH=20:1 to $CH_2Cl_2$: MeOH=10:1) to give a white solid (0.26 g, 74%, Rf=0.11 ($CH_2Cl_2$: MeOH=20:1)). $^1H$ NMR ($CD_3OD$, 400 MHz): δ IR (neat) $v_{max}$ 3402, 3064, 2934, 1694, 1473, 1369, 1244, 1041, 1005, 913, 784, 706.

Example 85-5-Fluoro-1-[cis-4-(hydroxymethyl)-cyclobutyl]cytosine

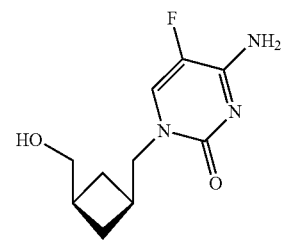

In a flask with 5-fluoro-1-[cis-4-(hydroxymethyl)cyclobutyl]cytosine (0.15 g, 0.66 mmol) inside, dry $CH_3CN$ 3.2 mL was added under argon, followed by the addition of 1-methylpyrrolidine (0.64 mL, 6.3 mmol) and chlorotrimethyl-silane (0.24 mL, 1.98 mmol) at room temperature. After 1 hr, the reactants were cooled to 0° C. and trifluoroacetic anhydride (0.44 mL, 3.3 mmol) was added dropwisely over 5 min. After 30 min at 0° C., a $CH_3CN$ solution of 4-nitrophenol (0.27 g, 1.98 mmol) was added drop by drop at 0° C. This was allowed to stir for 3 hr, after which time the mixture was poured into saturated $NaHCO_3$ and the resulting mixture was extracted with $CH_2Cl_2$ four times. The combined organic extracts were dried over $MgSO_4$ and evaporated under reduced pressure. The residue was dissolved in 1,4-dioxane 10 mL and concentrated ammonia hydroxide (28-30%) 2.5 mL was added. The mixture was heated in a sealed flask at 50-60° C. for 24 hr. The resulting solution was concentrated and the residue was co-evaporated with abs. EtOH. The crude product was purified by silica gel flash chromatography ($CH_2Cl_2$: MeOH=10:1) and then by reverse phase preparative HPLC($H_2O$ and $CH_3CN$ gradient) to give the desired product 0.06 g (40%, Rf=0.18 ($CH_2Cl_2$: MeOH=10:1)). $^1H$ NMR ($CDCl_3$, 400 MHz): δ 1.59-1.66 (m, 2H), 1.85-1.99 (m, 2H), 2.12-2.19 (m, 2H), 3.56-3.58 (d, J=8.0, 2H), 3.71-3.73 (d, J=8.0, 2H), 7.24-7.25 (d, J=4.0, 1H). $^{13}C$ NMR ($CDCl_3$, 100 MHz): δ 28.06, 30.49, 33.37, 53.92, 66.26, 128.71-129.03 (d, J=32), 139.41-141.78 (d, J=237), 149.89, 180.43. MS (FAB): expected for $C_{10}H_{14}FN_3O_2$ $(M+H)^+$ 228.24. Found: IR (neat) $v_{max}$ 3400, 3064, 2933, 1694, 1532, 1473, 1369, 1244, 1041, 1005, 910, 783, 752, 706.

Example 86-5-Fluoro-1-[trans-4-(hydroxymethyl)-cyclobutyl]cytosine

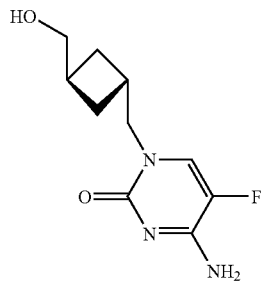

hu 1H NMR (CDCl₃, 400 MHz): δ 2.39-2.49 (m, 2H), 2.50-2.72 (m, 4H), 3.66-3.68 (d, J=4.0, 2H)), 3.79-3.81 (d, J=4.0, 2H), 7.23-7.24 (d, J=4.0, 1H). Example 87-9-[cis-4-(Benzyloxymethyl)-cyclobutyl]adenine

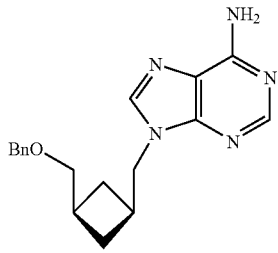

In a 25 mL three-neck flask with cis-1-hydroxylmethyl-3-(benzyloxymethyl)-cyclobutyl-mesylate (85.6 mg, 0.3 mmol), adenine (81 mg, 0.6 mmol), K₂CO₃ (83.2 mg, 0.6 mmol) and 18-crown-6 (159 mg, 0.6 mmol) inside, dry DMF 5 mL was added under argon. This was heated to 80° C. for 8 hr and then the volatile materials were removed by rotovap. The crude material was purified by silica gel flash chromatography (CH₂Cl₂: MeOH=20:1) to give the desired compound (63.2 mg, 65%). MS (FAB): expected for C₁₈H₂₁N₅O (M+H)⁺ 324.39. Found 324.18198. IR (neat) ν$_{max}$ 3276, 2922, 1675, 1606, 1570, 1458, 1414, 1308, 1214, 1071, 750. The absolute stereochemistry was established by X-ray crystallography analyses. Example 88-9-[cis-4-(Hydroxymethyl)-cyclobutyl] adenine

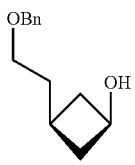

In a 50 mL flask with 9-[cis-4-(benzyloxymethyl)-cyclobutyl]adenine (63.2 mg, 0.2 mmol) inside, dry anisole 5 mL was added to give a light yellow solution under argon. In another 10 mL flask with AlCl₃ inside, dry anisole 2 mL was added under argon to give a totally clear red solution. This solution was added drop by drop to the first flask to give a red solution. After stirring at ambient temperature for 1 hr, TLC showed no starting material. The reaction mixture was cooled to 0° C. and dry MeOH was added drop by drop until the red color disappeared. The solvents were removed by rotovap to give an off-white solid and this was purified by silica gel flash chromatography (CH₂Cl₂: MeOH=15:1) to yield a white solid (33 mg, 72.4%, Rf=0.15 (CH₂Cl₂: MeOH=15:1)).

Example 89

3-(Benzyloxyethyl)cyclobutanone

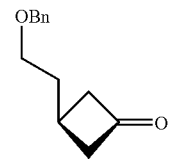

Zinc dust was added to a solution of 3-(benzyloxyethyl)-2,2-dichlorocyclobutanone in glacial acetic acid at room temperature. The reactants were heated at 60° C. for 1 hr, after which time dry diethyl ether was added to the cooled products, which were then filtered. The residue was washed with diethyl ether and the combined filtrate and washings were concentrated under reduced pressure. The residue was dissolved in CH₂Cl₂, which was washed with saturated NaHCO₃ twice and water once. The organic phase was dried over MgSO₄ and the solvent was evaporated to give an oily product, which was purified by silica gel flash chromatography (Hexane: EtOAc=6:1). ¹H NMR (CDCl₃, 400 MHz): δ 1.85-1.90 (q, J=6.0, 2H), 2.45-2.56 (m, 1H), 2.66-2.74 (m, 2H), 3.07-3.15 (m, 2H), 3.48-3.51 (t, J=6.0, 2H), 4.48 (s, 2H), 7.24-7.35 (m, 5H). ¹³C NMR (CDCl₃, 100 MHz): δ 21.29, 36.02, 52.56, 68.85, 72.99, 127.56, 127.62, 128.40, 138.33, 208.25. Rf=0.45 (Hexane: EtOAc=3:1). IR (neat) ν$_{max}$ 3054, 2927, 2856, 1779, 1266, 737, 704.

Example 90 cis-3-(Benzyloxyethyl)cyclobutanol

In a 100 mL flask with 3-(benzyloxyethyl)cyclobutanone (2.5 g, 12.2 mmol) inside, dry THF 30 mL was added under argon to give a light yellow solution. This was cooled to −78° C., after a while, L-selectride (1.0 M in THF, 14.7 mL, 14.6 mmol) was added drop by drop and this was allowed to warm up to room temperature, after which the reaction was quenched with saturated NaHCO₃. Then the mixture was cooled to 0° C. and 30% H₂O₂ was added drop by drop, followed by the addition of H₂O and EtOAc. The organic phase was separated, washed with H₂O twice and brine once, dried over MgSO₄ and solvent evaporation gave the crude product, which was purified by silica gel flash chromatography (Hexane: EtOAc=3:1) to give a colorless oil (2.0 g, 79.4%, Rf=0.2 (Hexane: EtOAc=3:1)). ¹H NMR (CDCl₃, 300 MHz): δ 1.40-1.60 (m, 2H), 1.60-1.90 (m, 3H), 2.05-2.21 (bs, 1H), 2.38-2.50 (m, 2H), 3.32-3.44 (t, J=, 2H), 4.52 (s, 2H), 7.20-7.40 (m, 5H). ¹³C NMR (CDCl₃, 75 MHz): δ 22.90, 37.08, 37.85, 39.91, 64.14, 68.78, 73.04, 127.62, 127.68, 128.45, 138.59. MS (FAB): expected for $C_{13}H_{18}O_2$ (M+H)$^+$ 207.28. Found 207.13801.

Example 91 trans-3-(Benzyloxyethyl)cyclobutyl 4-nitrobenzoate

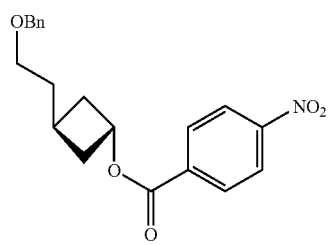

In a 100 mL flask with cis-3-(benzyloxyethyl)cyclobutanol (1.84 g, 8.9 mmol), 4-nitrobenzoic acid (2.97 g, 17.8 mmol) and $Ph_3P$ (4.9 g, 18.7 mmol) inside, dry THF 25 mL was added under argon to give a colorless solution. This was cooled to 0° C. and DIAD (3.7 mL, 18.7 mmol) was added drop by drop. After 15 hr, the volatile materials were evaporated and the crude mixture was purified by silica gel flash chromatography (Hexane: EtOAc=9:1) to give off-white oil contaminated with some DIAD (3.74 g). $^1$H NMR (CDCl$_3$, 400 MHz): δ 1.81-1.86 (m, 2H), 2.22-2.28 (m, 2H), 2.34-2.41 (m, 2H), 2.48-2.60 (m, 1H), 3.36-3.39 (t, J=6.4, 2H), 4.49 (s, 2H), 5.31-5.38 (m, 1H), 7.25-7.36 (m, 5H), 8.19-8.21 (dd, J=8.8, 2.0, 2H), 8.26-8.29 (dd, J=9.2, 2.0, 2H). $^{13}$C NMR (CDCl$_3$, 100 MHz): δ 26.35, 34.84, 35.96, 68.82, 70.74, 73.17, 123.70, 127.76, 128.59, 130.88, 135.97, 138.65, 150.68, 164.42. MS (FAB): expected for $C_{20}H_{21}NO_5$ (M−H)$^+$ 354.38. Found 354.13378. IR (neat) $v_{max}$ 2979, 2936, 2857, 1720, 1607, 1527, 1349, 1319, 1276, 1119, 1015, 874, 843, 738, 720, 698.

Example 92 trans-3-(Benzyloxyethyl)cyclobutanol

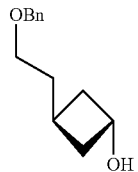

Aqueous NaOH (0.4 mol/L, 52 mL, 20.8 mmol) was added to a stirred solution of trans-3-(benzyloxyethyl)cyclobutyl 4-nitrobenzoate (3.7 g, 10.4 mmol) in 80 mL 1,4-dioxane at ambient temperature. After 40 min, AcOH (0.9 mL, 15.4 mmol) was added drop by drop. After 5 min, the reaction mixture was concentrated by rotovap. The residue was partitioned between EtOAc (50 mL) and saturated NaHCO$_3$ (2×50 mL). The organic phase was dried over MgSO$_4$ and solvent evaporation gave light yellow oil (2.09 g, 97.5%). $^1$H NMR (CDCl$_3$, 300 MHz): δ 1.71-1.78 (m, 2H), 1.94 (bs, 1H), 2.03-2.07 (m, 3H), 2.60-2.74 (m, 1H), 3.40-3.45 (t, J=6.9, 2H), 4.49 (s, 2H), 7.27-7.37 (m, 5H). $^{13}$C NMR (CDCl$_3$, 75 MHz): δ 24.58, 36.11, 37.90, 39.95, 66.63, 69.17, 73.10, 127.65, 127.69, 128.45, 138.60.

Example 93 trans-3-(Benzyloxyethyl)cyclobutyl-mesylate

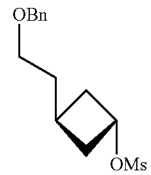

In a 500 mL flask with trans-3-(benzyloxyethyl)cyclobutanol (2.0 g, 9.7 mmol) inside, 200 mL dry CH$_2$Cl$_2$ was added under argon, followed by the addition of Et$_3$N (1.35 mL, 48.5 mmol). After 5 min, the reaction mixture was cooled to 0° C. and MsCl (0.9 mL, 11.6 mmol) was added drop by drop. After reacting for 1 hr at 0° C., the reaction was quenched by adding H$_2$O and the organic phase was separated, washed with brine once, dried over MgSO$_4$ and concentrated to give a light yellow crude product (2.5 g, 90.7%). $^1$H NMR (CDCl$_3$, 300 MHz): δ 1.74-1.81 (m, 2H), 2.17-2.24 (m, 2H), 2.40-2.53 (m, 3H), 2.96 (s, 3H), 3.42-3.46 (t, J=6.3, 2H), 4.48 (s, 2H), 5.06-5.14 (m, 1H), 7.25-7.37 (m, 5H). $^{13}$C NMR (CDCl$_3$, 75 MHz): δ 25.73, 35.39, 35.47, 38.46, 68.69, 73.13, 74.85, 127.65, 128.47, 138.43. MS (FAB): expected for $C_{14}H_{20}O_4S$ (M+H) 285.37. Found 285.11569. IR (neat) $v_{max}$ 3435, 3054, 2926, 2855, 1639, 1455, 1359, 1265, 1174, 1097, 971, 908, 738, 703.

Example 94

N3—PMB-5-Fluoro-1-[cis-3-(benzyloxyethyl)cyclobutyl]uracil

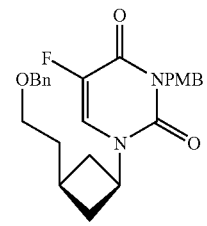

In a 50 mL three-neck flask with trans-3-(benzyloxyethyl)cyclobutyl-mesylate (0.34 g, 1.2 mmol), N3-PMB-5-fluorouracil (0.36 g, 1.44 mmol), K$_2$CO$_3$ (0.2 g, 1.44 mmol) and 18-crown-6 (0.38 g, 1.44 mmol) inside, dry DMF 10 mL was added under argon to give a light yellow solution with some white solids at the bottom of the flask. After 5 min, start to heat to 120° C. After 24 hr, add 30 mL EtOAc and 20 mL H$_2$O. The organic phase was separated and washed with brine once. The organic phase was dried over MgSO$_4$ and the solvents were evaporated to give the crude product, which was purified by silica gel flash chromatography (Hexane: EtOAc=3:1) to give an off-white solid (0.27 g, 50.9%) combined with some three-membered ring by-products. $^1$H NMR (CDCl$_3$, 300 MHz): δ 1.72-1.79 (m, 4H), 2.16-2.24 (m, 1H), 2.51-2.60 (m, 2H), 3.43-3.48 (m, 2H), 3.77 (s, 3H), 4.48 (s, 2H), 4.64-4.75 (m, 1H), 5.05 (s, 2H), 6.81-6.84 (d, J=9.0, 2H), 7.29-7.36 (m, 6H), 7.44-7.47 (d, J=9.0, 2H). MS (FAB): expected for $C_{25}H_{27}FN_2O_4$ (M+H)$^+$ 439.49. Found 439.20320. IR (neat) $v_{max}$ 2926, 2854, 1712, 1458, 1377, 1265, 895, 740, 705.

Example 95-5-Fluoro-1-[cis-3-(hydroxyethyl)cyclobutyl]uracil

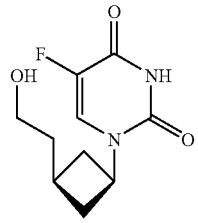

In a 10 mL flask with AlCl$_3$ (0.81 g, 6.2 mmol) inside, dry anisole 3 mL was added under argon to give a light yellow solution. In another flask with N3—PMB-5-fluoro-1-[cis-3-(benzyloxyethyl)cyclobutyl]uracil (0.27 g, 0.62 mmol) inside, dry anisole 2 mL was added, after which time AlCl$_3$ solution was added to it slowly at room temperature by syringe pump. After addition finishes, the mixture was cooled to 0° C. and dry MeOH was added slowly to give a colorless solution at the end. Then the solvents were removed and the product was purified by silica gel flash chromatography (CH$_2$Cl$_2$: MeOH=20:1) to give a white solid (73.7 mg, 53.4%) combined with some three-membered ring by-products. $^1$H NMR (CD$_3$OD, 300 MHz): δ 1.68-1.74 (m, 2H), 1.86-1.95 (m, 2H), 2.11-2.20 (m, 1H), 2.48-2.55 (m, 2H), 3.52-3.59 (m, 2H), 4.57-4.69 (m, 1H), 7.90-7.93 (d, J=6.9, 1H). $^{13}$C NMR (CDCl$_3$, 100 MHz): δ 10.02, 10.93, 15.94, 18.55, 26.78, 36.15, 37.49, 40.11, 47.47, 53.57, 61.10, 62.87, 127.81, 128.14, 131.01, 131.35, 140.70, 143.01, 151.84, 152.19, 160.41.

MS (FAB): expected for $C_{10}H_{13}FN_2O_3$ (M+H)$^+$ 229.22. Found 229.09835. IR (neat) $v_{max}$ 3411, 3187, 3063, 2934, 1697, 1473, 1357, 1272, 1243, 1043, 899, 807, 751, 704.

Example 96

9-[cis-3-(Benzyloxyethyl)cyclobutyl]adenine

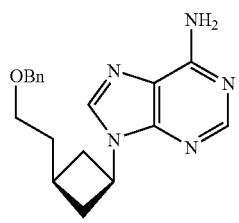

In a 25 mL three-neck flask with trans-3-(benzyloxyethyl)cyclobutyl-mesylate (0.50 g, 1.76 mmol), adenine (0.35 g, 2.59 mmol) and Cs$_2$CO$_3$ (0.86 g, 2.64 mmol) inside, dry DMF 8 mL was added under argon. Then began to heat to 120° C. and after 24 hr, the solvent was removed and directly applied to silica gel flash chromatography to give 0.24 g (43%) the desired product. $^1$H NMR (CDCl$_3$, 300 MHz): δ 1.84-1.92 (m, 2H), 2.16-2.46 (m, 3H), 2.68-2.80 (m, 2H), 3.48-3.52 (t, J=6.3, 2H), 4.51 (s, 2H), 4.80-4.92 (m, 1H), 7.88 (s, 1H), 8.35 (s, 1H). MS (FAB): expected for $C_{18}H_{21}N_5O$ (M+H)$^+$ 324.39. Found 324.18195. IR (neat) $v_{max}$ 3398, 2927, 2862, 1718, 1453, 1315, 1276, 1113, 1071, 1027, 738, 714, 698.

Example 97

9-[cis-3-(Hydroxyethyl)cyclobutyl]adenine

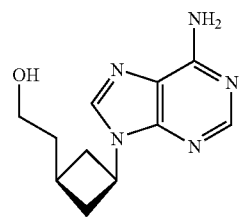

In a 10 mL flask with 9-[cis-3-(benzyloxyethyl)cyclobutyl]adenine (0.24 g, 0.74 mmol) inside, dry CH$_2$Cl$_2$ 5 mL was added. After cooling to −78° C., BCl$_3$ (1.0 M in CH$_2$Cl$_2$, 2.2 mL, 2.22 mmol) was added drop by drop. This was allowed to warm up to 0° C. and after 6 hr, the reaction was quenched by adding 7 N NH$_3$ in MeOH (2.6 mL, 18.3 mmol) and the solvent was removed by rotovap. The crude material was applied directly to silica gel flash chromatography to give the desired product 0.1 g (58%). $^1$H NMR (CD$_3$OD, 300 MHz): δ 1.75-1.84 (m, 2H), 2.27-2.44 (m, 3H), 2.71-2.80 (m, 2H), 3.56-3.62 (m, 2H), 4.82-4.95 (m, 1H), 8.22 (s, 1H), 8.30 (s, 1H). MS (FAB): expected for $C_{11}H_{15}N_5O$ (M+H) 234.27. Found 234.13489. IR (neat) $v_{max}$ 3327, 3184, 2929, 1648, 1600, 1574, 1477, 1416, 1333, 1305, 1248, 1045, 798, 720, 648.

Example 98

3-Butenyloxy-tert-butyl-diphenyl-silane

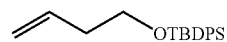

In a 500 mL flask with 3-butene-1-ol (5.9 mL, 67 mmol) and imidazole (5.19 g, 76.3 mmol) inside, dry CH$_2$Cl$_2$ 200 mL was added to give a colorless solution under argon. Then TBDPSCl (14.8 mL, 57.8 mmol) was added drop by drop. After stirring at ambient temperature for 10 min, DMAP (0.3 g, 2.3 mmol) was added all at once. The reaction mixture was left stirring at ambient temperature for 5 hr, after which time Et$_2$O and H$_2$O were added. The separated organic phase was washed with brine and dried over MgSO$_4$ and solvent evaporation gave a light yellow oil (17.4 g, 97%), which is pure enough for the next step. $^1$H NMR (CDCl$_3$, 300 MHz): δ 1.05

(s, 9H), 2.29-2.35 (m, 2H), 3.687-3.731 (t, J=6.6, 2H), 5.00-5.10 (m, 2H), 5.77-5.90 (m, 1H), 7.36-7.43 (m, 6H), 7.66-7.69 (m, 4H).

Example 99

3-(tert-Butyl-diphenyl-siloxyethyl)-2,2-dichlorocyclobutanone

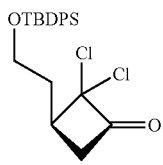

Trichloroacetyl chloride (9.7 mL, 86.8 mmol) was added slowly to a stirred suspension of freshly activated zinc-copper couple (6.4 g, 98.5 mmol), 3-butenyloxy-tert-butyl-diphenylsilane (10.1 g, 32.5 mmol), dry 1,2-DCE (16 mL) and dry diethyl ether (120 mL) in a 250 mL three-neck flask under argon. The reactants were heated under gentle reflux for 1d. The products were then filtered and the residue was washed with ether. The combined filtrate and washings were concentrated under reduced pressure. Light petroleum ether was added and the mixture was stirred vigorously. Then the supernatant was decanted and more light petroleum ether was added. After vigorous stirring the supernatant was again decanted and mixed with the original supernatant. The resulting solution was washed with saturated NaHCO$_3$ twice and brine once. The organic phase was dried over MgSO$_4$ and the solvent was evaporated to give light yellow oil, which was used directly in the next step. $^1$H NMR (CDCl$_3$, 300 MHz): δ 1.06 (s, 9H), 1.76-1.87 (m, 1H), 2.12-2.22 (m, 1H), 2.94-3.02 (m, 1H), 3.06-3.19 (m, 1H), 3.25-3.34 (m, 1H), 3.70-3.86 (m, 2H), 7.37-7.47 (m, 6H), 7.64-7.68 (m, 4H). $^{13}$C NMR (CDCl$_3$, 100 MHz): δ 19.37, 27.04, 34.26, 43.48, 48.17, 61.64, 89.17, 127.99, 130.05, 134.99, 135.75, 193.41. IR (neat) ν$_{max}$ 2956, 2930, 2857, 1810, 1767, 1472, 1428, 1391, 1112, 823, 739, 702.

Example 100

3-(tert-Butyl-diphenyl-siloxyethyl)-cyclobutanone

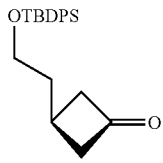

Zinc dust (15.7 g, 0.24 mol) was added to a solution of 3-(tert-butyl-diphenyl-siloxyethyl)-2,2-dichlorocyclobutanone (17 g, 0.04 mol) in glacial acetic acid (68 mL) at room temperature. The reactants were heated at 60° C. for 1 hr, after which time dry diethyl ether was added to the cooled products, which were then filtered. The residue was washed with diethyl ether and the combined filtrate and washings were concentrated under reduced pressure. The residue was dissolved in CH$_2$Cl$_2$, which was washed with saturated NaHCO$_3$ twice and water once. The organic phase was dried over MgSO$_4$ and the solvent was evaporated to give an oily product, which was purified by silica gel flash chromatography (Hexane: EtOAc=12:1) to give a colorless oil (6.2 g, 43.7%). $^1$H NMR (CDCl$_3$, 400 MHz): δ 1.06 (s, 9H), 1.82-1.87 (m, 2H), 2.48-2.60 (m, 1H), 2.65-2.71 (m, 2H), 3.07-3.14 (m, 2H), 3.69-3.73 (t, J=6.0, 6.4, 2H), 7.37-7.46 (m, 6H), 7.65-7.73 (m, 4H). $^{13}$C NMR (CDCl$_3$, 100 MHz): δ 19.37, 26.76, 27.06, 39.02, 52.87, 62.87, 127.91, 129.88, 129.92, 133.86, 208.89. IR (neat) ν$_{max}$ 2957, 2930, 2857, 1784, 1472, 1428, 1388, 1112, 822, 739, 702.

Example 101 cis-3-(tert-Butyl-diphenyl-siloxyethyl)cyclobutanol

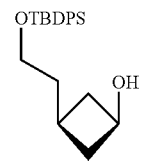

In a 50 mL flask with 3-(tert-butyl-diphenyl-siloxyethyl) cyclobutanone (0.48 g, 1.36 mmol) inside, dry THF 10 mL was added under argon to give a light yellow solution. This was cooled to −78° C., after a while, L-selectride (1.0 M in THF, 1.6 mL, 1.63 mmol) was added drop by drop and this was allowed to warm up to room temperature, after which the reaction was quenched with saturated NaHCO$_3$. Then cool the mixture to 0° C., add 30% H$_2$O$_2$ drop by drop, followed by the addition of H$_2$O and EtOAc. The organic phase was separated, washed with H$_2$O twice and brine once, dried over MgSO$_4$ and solvent evaporation gave the crude product, which was purified by silica gel flash chromatography (Hexane: EtOAc=9:1) to give a colorless oil (0.3 g, 61.8%). $^1$H NMR (CDCl$_3$, 300 MHz): δ 1.04 (s, 9H), 1.40-2.10 (m, 5H), 2.38-2.47 (m, 2H), 3.58-3.62 (t, J=6.3, 2H), 4.04-4.14 (m, 1H), 7.34-7.45 (m, 6H), 7.64-7.67 (m, 4H).

Example 102 cis-3-(tert-Butyl-diphenyl-siloxyethyl)cyclobutyl-mesylate

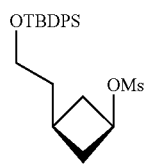

In a 100 mL flask with cis-3-(tert-butyl-diphenyl-siloxyethyl)cyclobutanol (0.3 g, 0.85 mmol) inside, 17 mL dry CH$_2$Cl$_2$ was added under argon, followed by the addition of Et$_3$N (0.6 mL, 4.25 mmol). After 5 min, the reaction mixture was cooled to 0° C. and MsCl (0.08 mL, 1.02 mmol) was added drop by drop. After reacting for 1 hr at 0° C., the reaction was quenched by H$_2$O and the organic phase was separated, washed with brine once, dried (MgSO$_4$) and concentrated to give a light yellow crude product (0.22 g, 60.1%). $^1$H NMR (CDCl$_3$, 300 MHz): δ 1.67-1.74 (m, 2H), 1.84-2.18 (m, 3H), 2.50-2.60 (m, 2H), 2.96 (s, 3H), 3.59-3.63 (t, J=6.0, 6.3, 2H), 4.79-4.89 (m, 1H), 7.34-7.45 (m, 6H), 7.64-7.67 (m, 4H). $^{13}$C NMR (CDCl$_3$, 100 MHz): δ 19.37, 24.21, 27.04, 37.45, 38.51, 39.62, 62.21, 71.52, 127.88, 129.87, 133.95, 135.75.

Example 103-3-Butenyloxy-triisopropyl-silane

In a 250 mL flask with 3-butene-1-ol (5.9 mL, 69 mmol) and imidazole (11.79 g, 172.5 mmol) inside, dry DMF 100 mL was added to give a colorless solution under argon. Then TIPSCl (17.8 mL, 82.8 mmol) was added drop by drop. The reaction mixture was left stirring at ambient temperature for 13.5 hr, after which time adding 2 N HCl, H$_2$O and EtOAc. The organic phase was separated, washed with H$_2$O once, brine once and dried over MgSO$_4$ and solvent evaporation gave a light yellow oil (14.95 g, 94.4%), which is pure enough for the next step. $^1$H NMR (CDCl$_3$, 400 MHz): δ 1.00-1.12 (m, 21H), 2.28-2.34 (m, 2H), 3.72-3.75 (t, J=6.8, 2H), 5.00-5.10 (m, 2H), 5.80-5.91 (m, 1H). $^{13}$C NMR (CDCl$_3$, 100 MHz): δ 12.23, 18.21, 37.89, 63.31, 116.38, 135.75.

Example 104

3-(Triisopropyl-siloxyethyl)-2,2-dichlorocyclobutanone

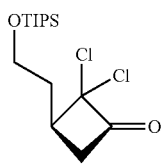

Trichloroacetyl chloride (19.5 mL, 174.7 mmol) was added slowly to a stirred suspension of freshly activated zinc-copper couple (12.9 g, 198.2 mmol), 3-butenyloxy-triisopropyl-silane (14.95 g, 65.4 mmol), dry 1,2-DCE (32 mL) and dry diethyl ether (200 mL) in a 500 mL three-neck flask under argon. The reactants were heated under gentle reflux for 1d. The products were then filtered and the residue was washed with diethyl ether. The combined filtrate and washings were concentrated under reduced pressure. Light petroleum ether was added and the mixture was stirred vigorously. Then the supernatant was decanted and more light petroleum ether was added. After vigorous stirring the supernatant was again decanted and mixed with the original supernatant. The resulting solution was washed with saturated NaHCO$_3$ twice and brine once. The organic phase was dried over MgSO$_4$ and the solvent was evaporated to give light yellow oil, which was used directly in the next step. $^1$H NMR (CDCl$_3$, 300 MHz): δ 1.06-1.15 (m, 21H), 1.77-1.89 (m, 1H), 2.13-2.23 (m, 1H), 3.03-3.20 (m, 1H), 3.22-3.58 (m, 2H), 3.72-3.90 (m, 2H).

Example 105

3-(Triisopropyl-siloxyethyl)-cyclobutanone

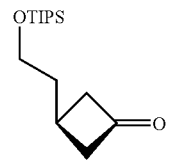

Zinc dust (25.5 g, 0.39 mol) was added to a solution of 3-(triisopropyl-siloxyethyl)-2,2-dichlorocyclobutanone (22.21 g, 65.4 mmol) in glacial acetic acid (110 mL) at room temperature. The reactants were heated at 60° C. for 1 hr, after which time dry diethyl ether was added to the cooled products, which were then filtered. The residue was washed with diethyl ether and the combined filtrate and washings were concentrated under reduced pressure. The residue was dissolved in dichloromethane, which was washed with saturated NaHCO$_3$ twice and water once. The organic phase was dried over MgSO$_4$ and the solvent was evaporated to give an oily product, which was purified by silica gel flash chromatography (Hexane: EtOAc=12:1) to give a colorless oil. $^1$H NMR (CDCl$_3$, 400 MHz): δ 1.03-1.08 (m, 21H), 1.80-1.85 (m, 2H), 2.49-2.60 (m, 1H), 2.71-2.80 (m, 2H), 3.12-3.21 (m, 2H), 3.74-3.77 (t, J=6.0, 2H). $^{13}$C NMR (CDCl$_3$, 100 MHz): δ 12.12, 18.22, 21.38, 39.36, 52.92, 62.37, 209.00. MS (FAB): expected for C$_{15}$H$_{30}$O$_2$Si (M+H)$^+$ 271.48. Found 271.20887. IR (neat) ν$_{max}$ 3053, 2925, 2866, 1778, 1462, 1265, 1103, 1013, 883, 740, 705.

Example 106 cis-3-(Triisopropyl-siloxyethyl)cyclobutanol

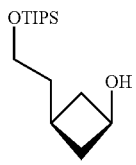

In a 50 mL flask with cis-3-(triisopropyl-siloxyethyl)cyclobutanone (0.78 g, 2.89 mmol) inside, dry THF 20 mL was added under argon to give a light yellow solution. This was cooled to −78° C., after a while, L-selectride (1.0 M in THF, 3.5 mL, 3.47 mmol) was added drop by drop and this was allowed to warm up to room temperature, after which the reaction was quenched with saturated NaHCO$_3$. Then cool the mixture to 0° C., add 30% H$_2$O$_2$ drop by drop, followed by the addition of H$_2$O and EtOAc. The organic phase was separated, washed with H$_2$O twice and brine once, dried over MgSO$_4$ and solvent evaporation gave the crude product, which was purified by silica gel flash chromatography (Hexane: EtOAc=9:1) to give a colorless oil (0.57 g, 72%). $^1$H NMR (CDCl$_3$, 400 MHz): δ 1.00-1.04 (m, 21H), 1.45-1.54 (m, 2H), 1.59-1.67 (m, 2H), 1.73-1.83 (m, 1H), 2.39-2.46 (m, 2H), 2.71 (bs, 1H), 3.58-3.61 (t, J=6.4, J=6.8, 2H), 4.02-4.10

(m, 1H). $^{13}$C NMR (CDCl$_3$, 100 MHz): δ 12.11, 18.16, 22.70, 39.92, 40.43, 61.94, 64.15. MS (FAB): expected for C$_{15}$H$_{32}$O$_2$Si (M+H)$^+$ 273.50. Found 273.22476.

Example 107 trans-3-(triisopropyl-siloxyethyl)cyclobutyl 4-nitrobenzoate

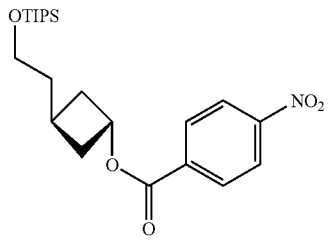

In a 100 mL flask with cis-3-(triisopropyl-siloxyethyl)cyclobutanol (0.64 g, 2.3 mmol), 4-nitrobenzoic acid (0.79 g, 4.6 mmol) and Ph$_3$P (1.29 g, 4.83 mmol) inside, dry THF 10 mL was added under argon to give a colorless solution. This was cooled to 0° C. and DIAD (1.0 mL, 4.83 mmol) was added drop by drop. After 15 hr, the volatile materials were evaporated and the crude mixture was purified by silica gel flash chromatography (Hexane: EtOAc=20:1 to Hexane: EtOAc=12:1) to give yellow oil contaminated with some DIAD (0.96 g, 97.4%, Rf=0.48 (Hexane: EtOAc=12:1)). $^1$H NMR (CDCl$_3$, 400 MHz): δ 1.02-1.07 (m, 21H), 1.74-1.79 (m, 2H), 2.24-2.33 (m, 2H), 2.35-2.42 (m, 2H), 2.48-2.60 (m, 1H), 3.67-3.71 (t, J=6.4, 2H), 5.30-5.38 (m, 1H), 8.19-8.28 (m, 4H). $^{13}$C NMR (CDCl$_3$, 100 MHz): δ 12.13, 18.19, 25.97, 34.87, 39.08, 61.95, 70.81, 123.66, 130.85, 136.01, 150.65, 164.39. MS (FAB): expected for C$_{22}$H$_{35}$NO$_5$Si (M+H)$^+$ 422.60. Found 422.23608. IR (neat) v$_{max}$ 2942, 2865, 1725, 1608, 1530, 1463, 1349, 1276, 1103, 882, 720, 681.

Example 108 trans-3-(Triisopropyl-siloxyethyl)cyclobutanol

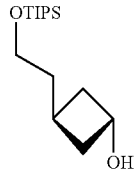

Aqueous NaOH (0.4 mol/L, 12 mL, 4.56 mmol) was added to a stirred solution of trans-3-(triisopropyl-siloxyethyl)cyclobutyl-4-nitrobenzoate (0.96 g, 2.28 mmol) in 18 mL 1,4-dioxane at ambient temperature. After 1 hr, AcOH was added drop by drop. After 5 min, the reaction mixture was concentrated by rotovap. The residue was partitioned between EtOAc (10 mL) and saturated NaHCO$_3$ (2×10 mL). The organic phase was dried over MgSO$_4$ and solvent evaporation gave light yellow oil (0.57 g, 92.3%, Rf=0.23 (Hexane: EtOAc=9:1)). $^1$H NMR (CDCl$_3$, 300 MHz): δ 1.00-1.07 (m, 21H), 1.63-1.70 (m, 2H), 1.78 (bs, 1H), 1.99-2.10 (m, 4H), 2.24-2.38 (m, 1H), 3.61-3.65 (t, J=6.6, 2H), 4.35-4.44 (m, 1H). $^{13}$C NMR (CDCl$_3$, 75 MHz): δ 12.23, 18.29, 24.24, 38.05, 39.37, 62.27, 66.82. MS (FAB): expected for C$_{15}$H$_{32}$O$_2$Si (M+H)$^+$ 273.50. Found 273.22456.

Example 109 trans-3-(Triisopropyl-siloxyethyl)cyclobutyl-mesylate

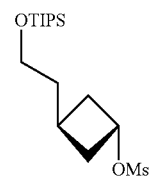

In a 100 mL flask with trans-3-(triisopropyl-siloxyethyl) cyclobutanol (0.53 g, 1.94 mmol) inside, 40 mL dry CH$_2$Cl$_2$ was added under argon, followed by the addition of Et$_3$N (1.36 mL, 9.7 mmol). After 5 min, the reaction mixture was cooled to 0° C. and MsCl (0.18 mL, 2.33 mmol) was added drop by drop. After reacting for 1 hr at 0° C., the reaction was quenched by adding H$_2$O and the organic phase was separated, washed with brine once, dried over MgSO$_4$ and concentrated to give a light yellow crude product (0.53 g, 77%, Rf=0.14 (Hexane: EtOAc=9:1)). $^1$H NMR (CDCl$_3$, 400 MHz): δ 1.01-1.06 (m, 21H), 1.66-1.71 (m, 2H), 2.19-2.24 (m, 2H), 2.41-2.51 (m, 3H), 2.97 (s, 3H), 3.64-3.67 (t, J=6.0, 2H), 5.07-5.14 (m, 1H). $^{13}$C NMR (CDCl$_3$, 100 MHz): δ 12.10, 18.19, 25.39, 35.45, 38.49, 38.58, 61.87, 75.03. MS (FAB): expected for C$_{16}$H$_{34}$O$_4$SSi (M+H)$^+$ 350.59. Found 351.20221. IR (neat) v$_{max}$ 2943, 2866, 1463, 1359, 1265, 1173, 1108, 909, 735.

Example 110

9-[cis-3-(Triisopropyl-siloxyethyl)cyclobutyl]adenine

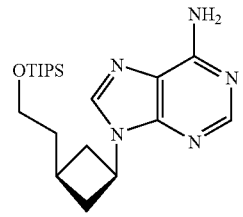

In a 25 mL three-neck flask with trans-3-(triisopropyl-siloxyethyl)cyclobutyl-mesylate (0.27 g, 7.7 mmol), adenine (0.16 g, 1.18 mmol) and Cs$_2$CO$_3$ (0.38 g, 1.17 mmol) inside, dry DMF 5 mL was added under argon. Then began to heat to 120° C. and after 24 hr, the solvent was removed and directly applied to silica gel flash chromatography to give 0.14 g (47%) the desired product. $^1$H NMR (CDCl$_3$, 400 MHz): δ 0.99-1.05 (m, 21H), 1.72-1.78 (m, 2H), 2.15-2.23 (m, 2H), 2.60-2.79 (m, 3H), 3.67-3.70 (t, J=6.0, 2H), 4.81-4.90 (m, 1H), 6.37-6.39 (bs, 2H), 7.88 (s, 1H), 8.31 (s, 1H). $^{13}$C NMR (CDCl$_3$, 100 MHz): δ 12.08, 18.17, 26.60, 37.03, 39.84, 45.86, 61.64, 138.76, 140.09, 150.07, 152.91, 155.93. MS (FAB): expected for C$_{20}$H$_{35}$N$_5$OSi (M+H)$^+$ 390.61. Found 390.26828. IR (neat) $v_{max}$ 2942, 2865, 1670, 1604, 1571, 1463, 1415, 1308, 1246, 1108, 882, 681, 658.

Example 111-9-[cis-3-(Hydroxylethyl)cyclobutyl]adenine

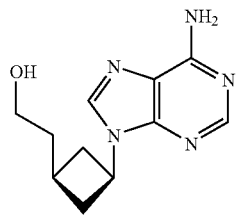

In a 25 mL flask with 9-[cis-3-(triisopropyl-siloxyethyl)cyclobutyl]adenine (0.07 g, 0.18 mmol) inside, dry THF 1.5 mL was added to give a totally clear light-yellow solution. This was treated with TBAF (1.0 M in THF, 0.36 mL, 0.36 mmol) at room temperature. After 1 hr, the solvent was removed and the crude product was directly applied to the silica gel flash chromatography ($CH_2Cl_2$ to $CH_2Cl_2$: MeOH=5:1) to give 0.04 g (90%) the desired product. MS (FAB): expected for $C_{11}H_{15}N_5O$ (M+H) 234.27. Found 234.13482.

Example 112

2-(6-Amino-purin-9-yl)-4-benzyloxymethyl-cyclobutanone

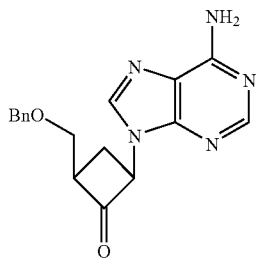

In a 25 mL flask with $CrO_3$ (94 mg, 0.94 mmol) inside, dry $CH_2Cl_2$ 2.2 mL was added under argon. This was cooled to 0° C. and then pyridine (0.15 mL, 1.88 mmol) and $Ac_2O$ (0.09 mL, 0.94 mmol) were added successively. The reaction mixture was allowed to warm up to room temperature and stirring was continued until a homogeneous solution was obtained. A solution of 1-[trans-2-hydroxyl-cis-3-(benzyloxymethyl)cyclobutyl]adenine (101.9 mg, 0.31 mmol) was added drop by drop. After reacting for 2 hr 40 min, the crude product was directly applied to the silica gel flash chromatography ($CH_2Cl_2$ to $CH_2Cl_2$: MeOH=10:1) to give 52.6 mg the desired product (55.5%, Rf=0.21 ($CH_2Cl_2$: MeOH=20:1). $^1$H NMR ($CDCl_3$, 600 MHz): δ 2.59-2.63 (m, 1H), 2.87-2.93 (m, 1H), 3.60-3.66 (m, 1H), 3.73-3.76 (m, 1H), 3.95-3.97 (m, 1H), 4.54-4.60 (m, 2H), 5.79-5.82 (t, J=9.0, 1H), 6.53 (bs, 2H), 7.27-7.37 (m, 5H), 7.81 (s, 1H), 8.25 (s, 1H). $^{13}$C NMR ($CDCl_3$, 150 MHz): δ 24.29, 56.10, 63.31, 66.85, 73.71, 118.76, 127.89, 128.11, 128.69, 137.70, 139.01, 149.45, 153.01, 155.88, 203.11. MS (FAB): expected for $C_{17}H_{17}N_5O_2$ (M+H)$^+$ 324.35. Found 324.14557. IR (neat) $v_{max}$ 3335, 3196, 1790, 1648, 1601, 1477, 1420, 1365, 1331, 1302, 1253, 1114, 1027, 910, 732, 698.

Example 113

9-[2-α,β-Fluoro-cis-3-(benzyloxymethyl)cyclobutyl]adenine

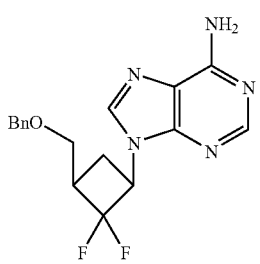

In a 25 mL flask with 2-(6-amino-purin-9-yl)-4-benzyloxymethyl-cyclobutanone (47.2 mg, 0.15 mmol) inside, dry $CH_2Cl_2$ 5 mL was added to give a light yellow solution under argon. After stirring for 5 min, DAST (0.11 mL, 0.9 mmol) was added drop by drop to give a little dark yellow solution. This was left stirring at temperature for 48 hr, after which the reaction was quenched by adding sat. $NaHCO_3$ 1 mL and diluted with more $CH_2Cl_2$. The organic phase was separated, dried over $MgSO_4$ and solvent evaporation gave the crude product that was purified by silica gel flash chromatography ($CH_2Cl_2$: MeOH=20:1) to give the desired product 3.5 mg (7%, Rf=0.28 ($CH_2Cl_2$: MeOH=20:1)). $^1$H NMR ($CDCl_3$, 400 MHz): δ 2.18-2.26 (m, 1H), 2.61-2.71 (m, 1H), 3.03-3.12 (m, 1H), 3.70-3.83 (m, 2H), 4.55-4.62 (m, 2H), 5.35-5.45 (m, 1H), 5.72 (bs, 2H), 7.30-7.40 (m, 5H), 7.93-7.94 (d, J=4.0, 1H), 8.37 (s, 1H). $^{13}$C NMR ($CDCl_3$, 100 MHz): δ 23.44-23.63 (d, J=19), 41.80-42.21 (t, J=21), 53.02-53.48 (dd, J=26), 66.08-66.15 (d, J=7.0), 73.62, 118, 119.39, 120.90, 123.66, 137.87, 139.37-139.41 (d, J=4.0), 150.43, 153.45, 155.59. $^{19}$F NMR ($CDCl_3$, 376 MHz): δ-131.70-(−131.11) (td, J=194.2, 14.3, 1F), −86.80-(−86.22) (qd, J=194.5, 8.2, 1F). MS (FAB): expected for $C_{17}H_{17}F_2N_5O$ (M+H)$^+$ 346.35. Found 346.14743.

IR (neat) $v_{max}$ 3330, 3179, 1648, 1599, 1474, 1454, 1422, 1366, 1334, 1294, 1249, 909, 734.

Example 114

Anti-HIV Activity

The following cyclobutyl nucleoside compounds were evaluated for their anti-HIV activity and cytotoxicity in PBM cells, according to standard procedures.

DLS-194
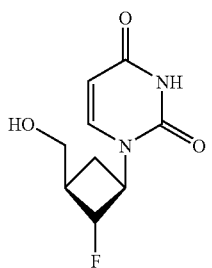
DLS-195
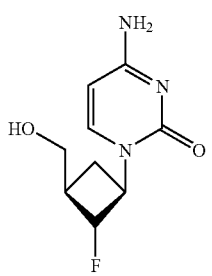
DLS-196
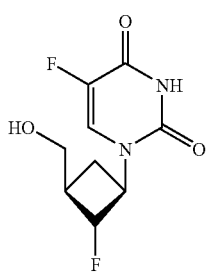
DLS-222
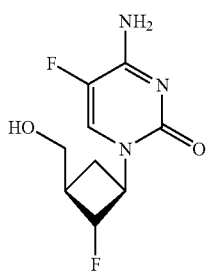
DLS-221
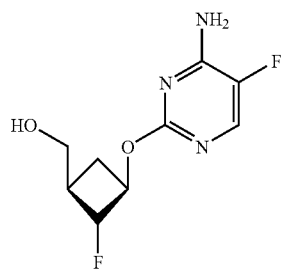
DLS-206
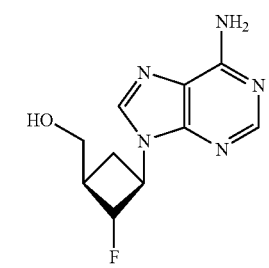
DLS-223
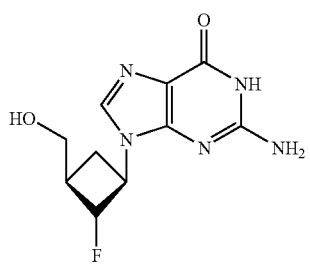
DLS-197
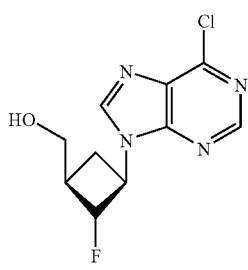
DLS-207
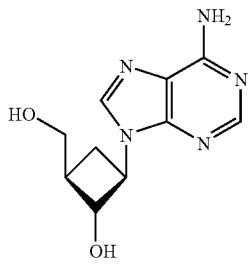
DLS-210
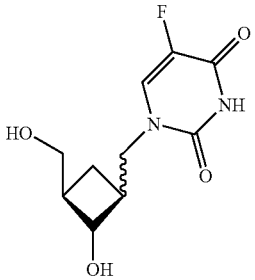
DLS-212
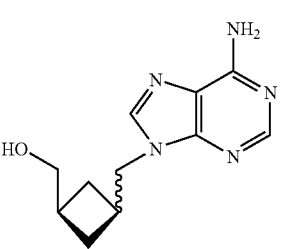
DLS-211
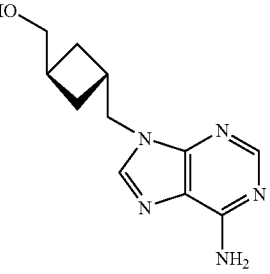

-continued

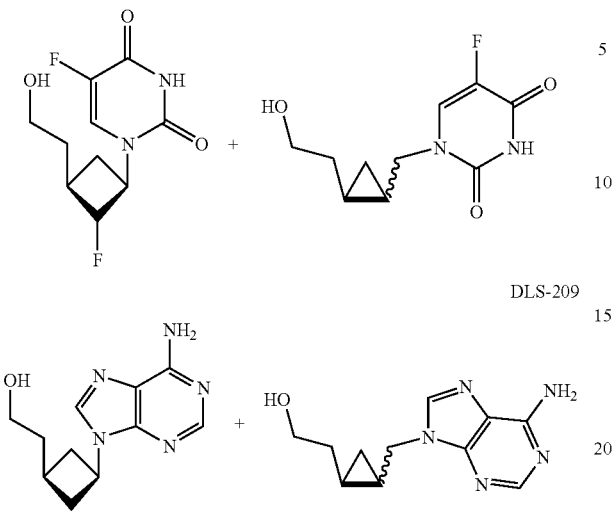

DLS-206, DLS-207 and DLS-223 exhibited significant inhibition of HIV-RT. (Table 6.) DLS-194, DLS-195, DLS-196, DLS-197, DLS-208, DLS-209, DLS-210, DLS-211, DLS-212, DLS-221, and DLS-222 were not active for HIV RT inhibition (EC50>100 μM) in this assay.

TABLE 6

Anti-HIV activity and toxicity of cyclobutyl nucleosides

| Compound | Activity (PBM) | | Toxicity (IC50 μM) | | |
|---|---|---|---|---|---|
| | EC50 (μM) | EC90 (μM) | PBM | CEM | Vero |
| DLS-206 | 50.4 | >100 | >100 | >100 | >100 |
| DLS-223 | 27.7 | >100 | >100 | >100 | >100 |
| DLS-207 | 33.7 | 60.1 | 13.8 | >100 | 97.8 |

This invention has been described with reference to its preferred embodiments. Variations and modifications of the invention, will be obvious to those skilled in the art from the foregoing detailed description of the invention. It is intended that all of these variations and modifications be included within the scope of this invention.

What is claimed is:

1. A nucleoside:

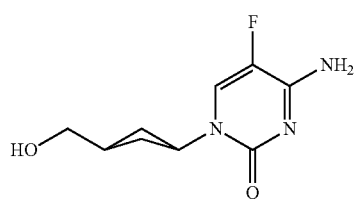

or a salt, acyl ester, salt of an acyl ester, enantiomer, diastereomer, or tautomer thereof.

2. A nucleoside selected from the group consisting of

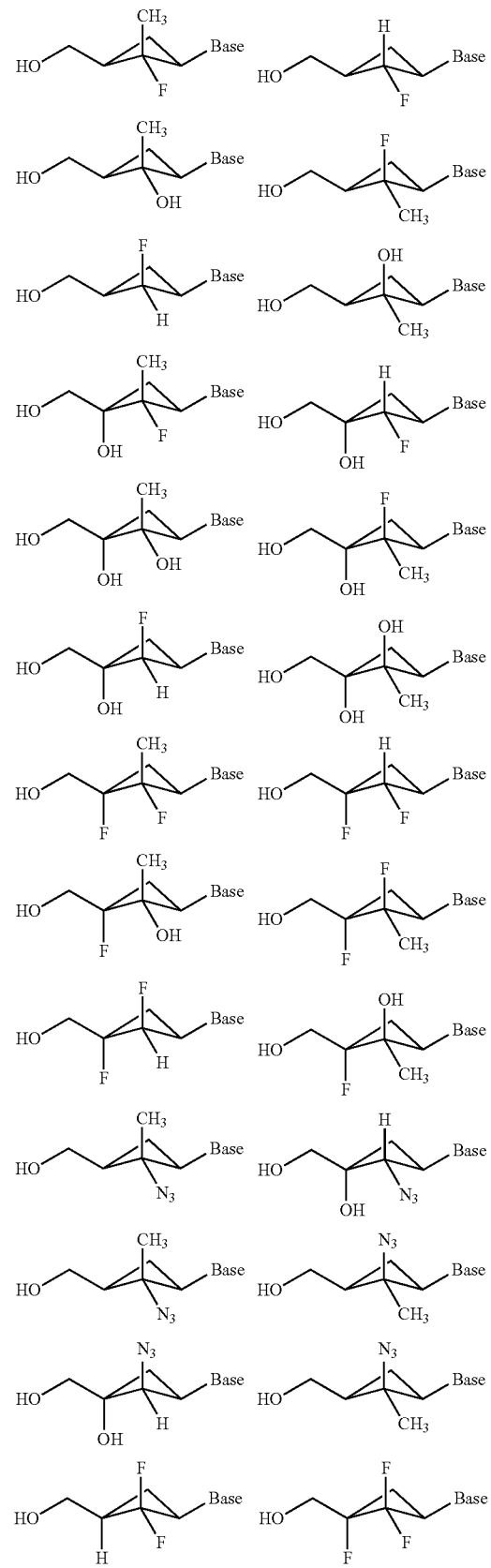

-continued

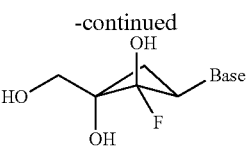

wherein, Base is a purine or pyrimidine base or a pharmaceutically acceptable salt, acyl ester, salt of an acyl ester, enantiomer, diastereomer, or tautomer thereof.

3. The nucleoside of claim 2, wherein the base is a pyrimidine.

4. The nucleoside of claim 3, wherein the pyrimidine is a 5-fluorocytidine.

5. The nucleoside of claim 2, wherein the base is a purine.

6. The nucleoside of claim 5, wherein the purine is guanine or adenine.

7. A nucleoside selected from the group consisting of:

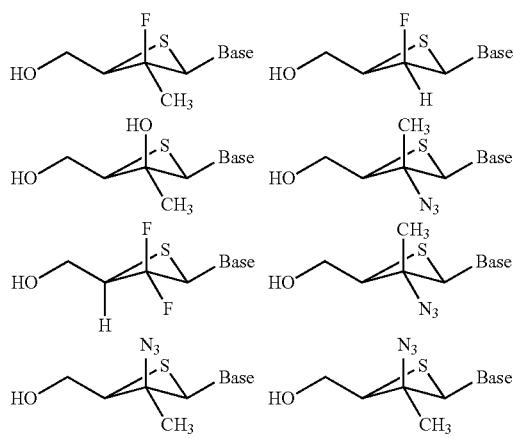

wherein, Base is a purine or pyrimidine base or a pharmaceutically acceptable salt, acyl ester, salt of an acyl ester, enantiomer, diastereomer, or tautomer thereof.

8. The nucleoside of claim 7, wherein the base is a pyrimidine.

9. The nucleoside of claim 8, wherein the pyrimidine is a 5-fluorocytidine.

10. The nucleoside of claim 7, wherein the base is purine.

11. The nucleoside of claim 10, wherein the purine is guanine or adenine.

12. A nucleoside selected from the group consisting of:

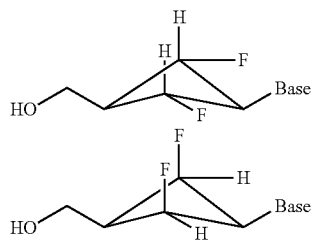

wherein, Base is a purine or pyrimidine base or a pharmaceutically acceptable salt, acyl ester, salt of an acyl ester, enantiomer, diastereomer, or tautomer thereof.

13. The nucleoside of claim 12, wherein the pyrimidine.

14. The nucleoside of claim 13, wherein the pyrimidine is a 5-fluorocytidine.

15. The nucleoside of claim 12, wherein the base is a purine.

16. The nucleoside of claim 15, wherein the purine is guanine or adenine.

17. A nucleoside selected from the group consisting of:

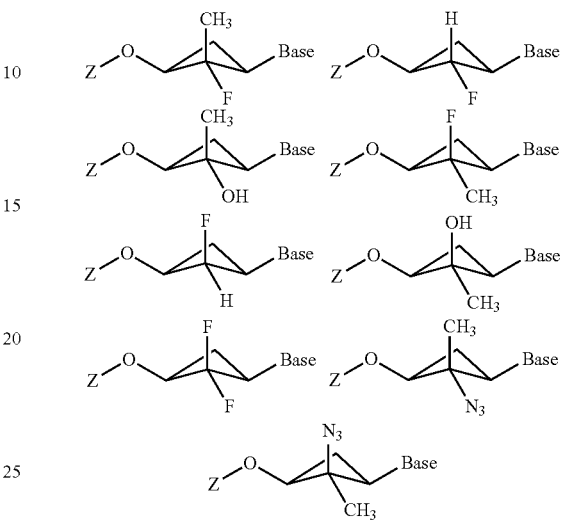

wherein, Base is a purine or pyrimidine base and Z is hydrogen or a pharmaceutically acceptable salt, acyl ester, salt of an acyl ester, enantiomer, diastereomer, or tautomer thereof.

18. The nucleoside of claim 17, wherein the base is a pyrimidine.

19. The nucleoside of claim 18, wherein the pyrimidine is a 5-fluorocytidine.

20. The nucleoside of claim 17, wherein the base is a purine.

21. The nucleoside of claim 20, wherein the purine is guanine or adenine.

22. A pharmaceutical composition comprising an effective amount of the nucleoside of claim 1, or a pharmaceutically acceptable salt thereof together with a pharmaceutically acceptable carrier or diluent.

23. A pharmaceutical composition comprising an effective amount of the nucleoside of claim 1, or a pharmaceutically acceptable salt thereof together with a pharmaceutically acceptable carrier or diluent and in combination with one or more other antivirally effective agents.

24. A pharmaceutical composition comprising an effective amount of the nucleoside of claim 2, or a pharmaceutically acceptable salt thereof together with a pharmaceutically acceptable carrier or diluent.

25. A pharmaceutical composition comprising an effective amount of the nucleoside of claim 2, or a pharmaceutically acceptable salt thereof together with a pharmaceutically acceptable carrier or diluent and in combination with one or more other antivirally effective agents.

26. A pharmaceutical composition comprising an effective amount of the nucleoside of claim 7, or a pharmaceutically acceptable salt thereof together with a pharmaceutically acceptable carrier or diluent.

27. A pharmaceutical composition comprising an effective amount of the nucleoside of claim 7, or a pharmaceutically acceptable salt thereof together with a pharmaceutically acceptable carrier or diluent and in combination with one or more other antivirally effective agents.

28. A pharmaceutical composition comprising an effective amount of the nucleoside of claim 12, or a pharmaceutically acceptable salt thereof together with a pharmaceutically acceptable carrier or diluent.

29. A pharmaceutical composition comprising an effective amount of the nucleoside of claim 12, or a pharmaceutically acceptable salt thereof together with a pharmaceutically acceptable carrier or diluent and in combination with one or more other antivirally effective agents.

30. A pharmaceutical composition comprising an effective amount of the nucleoside of claim 17, or a pharmaceutically acceptable salt thereof together with a pharmaceutically acceptable carrier or diluent.

31. A pharmaceutical composition comprising an effective amount of the nucleoside of claim 17, or a pharmaceutically acceptable salt thereof together with a pharmaceutically acceptable carrier or diluent and in combination with one or more other antivirally effective agents.

32. A nucleoside:

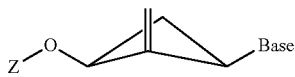

wherein, Base is a pyrimidine base and Z is hydrogen or a pharmaceutically acceptable salt, acyl ester, salt of an acyl ester, enantiomer, diastereomer, or tautomer thereof.

33. The nucleoside of claim 32, Wherein the pyrimidine is a 5-fluorocytidine.

34. A pharmaceutical composition comprising an effective amount of the nucleoside of claim 32, or a pharmaceutically acceptable salt thereof together with a pharmaceutically acceptable carrier or diluent.

35. A pharmaceutical composition comprising an effective amount of the nucleoside of claim 32, or a pharmaceutically acceptable salt thereof together with a pharmaceutically acceptable carrier or diluent and in combination with one or more other antivirally effective agents.

* * * * *

UNITED STATES PATENT AND TRADEMARK OFFICE
CERTIFICATE OF CORRECTION

| | | |
|---|---|---|
| PATENT NO. | : 8,114,994 B2 | |
| APPLICATION NO. | : 12/368876 | |
| DATED | : February 14, 2012 | |
| INVENTOR(S) | : Dennis C. Liotta et al. | |

It is certified that error appears in the above-identified patent and that said Letters Patent is hereby corrected as shown below:

Column 1, lines 5-6

On the first page of the specification, immediately below the Title, please insert the following:

--ACKNOWLEDGEMENT

This invention was made with government support under Grant Nos. AI028731 and AI041890 awarded by the National Institutes of Health. The government has certain rights in the invention--

Signed and Sealed this
Thirtieth Day of April, 2013

Teresa Stanek Rea
*Acting Director of the United States Patent and Trademark Office*